(12) United States Patent
Greve et al.

(10) Patent No.: US 10,472,405 B2
(45) Date of Patent: Nov. 12, 2019

(54) MULTIVALENT REGULATORY T CELL MODULATORS

(71) Applicant: Delinia, Inc., Emeryville, CA (US)

(72) Inventors: Jeffrey Greve, Berkeley, CA (US);
Jungmin Kim, Berkeley, CA (US);
Niranjana Nagarajan, Oakland, CA (US); John Cho, Stoneham, MA (US)

(73) Assignee: Delinia, Inc., Emeryville, CA (US)

( * ) Notice: Subject to any disclaimer, the term of this patent is extended or adjusted under 35 U.S.C. 154(b) by 44 days.

(21) Appl. No.: 15/840,721

(22) Filed: Dec. 13, 2017

(65) Prior Publication Data

US 2018/0162919 A1    Jun. 14, 2018

Related U.S. Application Data

(60) Provisional application No. 62/433,533, filed on Dec. 13, 2016.

(51) Int. Cl.

| | | |
|---|---|---|
| *C07K 14/55* | (2006.01) | |
| *C07K 14/54* | (2006.01) | |
| *C07K 16/28* | (2006.01) | |
| *A61P 29/00* | (2006.01) | |
| *A61P 21/00* | (2006.01) | |
| *A61P 37/06* | (2006.01) | |
| *A61P 1/00* | (2006.01) | |
| *A61P 17/06* | (2006.01) | |
| *A61P 3/10* | (2006.01) | |
| *A61P 25/28* | (2006.01) | |
| *A61P 17/14* | (2006.01) | |
| *A61P 17/00* | (2006.01) | |
| *C07K 19/00* | (2006.01) | |
| *C12N 15/09* | (2006.01) | |
| *A61K 38/00* | (2006.01) | |

(52) U.S. Cl.
CPC ............ *C07K 14/55* (2013.01); *A61P 1/00* (2018.01); *A61P 3/10* (2018.01); *A61P 17/00* (2018.01); *A61P 17/06* (2018.01); *A61P 17/14* (2018.01); *A61P 21/00* (2018.01); *A61P 25/28* (2018.01); *A61P 29/00* (2018.01); *A61P 37/06* (2018.01); *C07K 14/54* (2013.01); *C07K 16/2866* (2013.01); *C07K 19/00* (2013.01); *C12N 15/09* (2013.01); *A61K 38/00* (2013.01); *C07K 2317/52* (2013.01); *C07K 2317/55* (2013.01); *C07K 2317/71* (2013.01); *C07K 2317/92* (2013.01); *C07K 2319/30* (2013.01); *C07K 2319/74* (2013.01); *C07K 2319/75* (2013.01)

(58) Field of Classification Search
CPC ..................................................... C07K 14/55
See application file for complete search history.

(56) References Cited

U.S. PATENT DOCUMENTS

| | | |
|---|---|---|
| 9,382,318 B2 | 7/2016 | Smith et al. |
| 2010/0285014 A1 | 11/2010 | Cox, III et al. |
| 2014/0004107 A1 | 1/2014 | Smith et al. |
| 2016/0304574 A1 | 10/2016 | Sharma et al. |

FOREIGN PATENT DOCUMENTS

| | | |
|---|---|---|
| WO | 2005/030252 | 4/2005 |
| WO | 2016/014428 | 1/2016 |

OTHER PUBLICATIONS

Written Opinion dated Apr. 13, 2018 in co-pending International Application No. PCT/US2017/066163, 6 Pages.
International Search Report dated Apr. 13, 2018 in co-pending International Application No. PCT/US2017/066163, 6 Pages.
Villata, S. Armando, et al., "Regulatory T Cells Suppress Muscle Inflammation and Injury in Muscular Dystrophy", Science Translational Medicine, Oct. 15, 2014, vol. 6, No. 258, pp. 1-22.
Schiering, Chris, et al., "The Alarmin IL-33 Promotes Regulatory T Cell Function in the Intestine", Nature, Sep. 25, 2014, vol. 513, pp. 1-18.

*Primary Examiner* — Prema M Mertz
(74) *Attorney, Agent, or Firm* — McCarter & English, LLP

(57) ABSTRACT

This disclosure provides compounds that contain an IL-2 receptor-binding moiety and an ST2-binding moiety. The methods described in the present disclosure provide for a method for treating a condition by administering to a subject in need thereof a therapeutically-effective amount of a compound containing an IL-2 receptor-binding moiety and an ST2-binding moiety.

13 Claims, 23 Drawing Sheets

Specification includes a Sequence Listing.

IL2vNM-IL-33vCM

IL2vNM-IL33vNM

IL33vNM-IL2vCM

IL33vNB-IL2vCM

IL2vNB-IL33vCM

IL33vNB-IL2vCB

IL2vNB-IL33vCB

IL33vNM

IL33vCM

IL33vNB

Ab2-IL2vCB & Ab4-IL2vCB

Ab2-IL2vCM & Ab4-IL2vCM

Ab2M-IL2vCM & Ab4M-IL2vCM

Ab2M-IL2vNM & Ab4M-IL2vNM

Ab2M-IL2vCB & Ab4M-IL2vCB

SEQUENCE LISTING

<160> NUMBER OF SEQ ID NOS: 31

<210> SEQ ID NO 1
<211> LENGTH: 133
<212> TYPE: PRT
<213> ORGANISM: Artificial Sequence
<220> FEATURE:
<223> OTHER INFORMATION: IL2 N88R C125S mutant

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 3
<211> LENGTH: 133
<212> TYPE: PRT
<213> ORGANISM: Artificial Sequence

```
<220> FEATURE:
<223> OTHER INFORMATION: IL2 T3A, N88R, C125S mutant

<400> SEQUENCE: 3

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 4
<211> LENGTH: 226
<212> TYPE: PRT
<213> ORGANISM: Artificial Sequence
<220> FEATURE:
<223> OTHER INFORMATION: IgG1 Fc N297A, T350V, L351Y, F405A, Y407V
      mutant

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Val Tyr Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Ala Leu Val Ser Leu Thr Val
            180                 185                 190
```

```
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
    210                 215                 220
Pro Gly
225

<210> SEQ ID NO 5
<211> LENGTH: 226
<212> TYPE: PRT
<213> ORGANISM: Artificial Sequence
<220> FEATURE:
<223> OTHER INFORMATION: IgG1 Fc N297A, T350V, T366L, K392L, T394W
      mutant

<400> SEQUENCE: 5

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Ala Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Val Leu Pro Pro Ser Arg Asp Glu Leu Thr Lys Asn Gln Val Ser
    130                 135                 140
Leu Leu Cys Leu Val Lys Gly Phe Tyr Pro Ser Asp Ile Ala Val Glu
145                 150                 155                 160
Trp Glu Ser Asn Gly Gln Pro Glu Asn Asn Tyr Leu Thr Trp Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly
225

<210> SEQ ID NO 6
<211> LENGTH: 15
<212> TYPE: PRT
<213> ORGANISM: Artificial Sequence
<220> FEATURE:
<223> OTHER INFORMATION: Peptide linker

<400> SEQUENCE: 6

Gly Gly Gly Gly Ser Gly Gly Gly Gly Ser Gly Gly Gly Gly Ser
1               5                   10                  15
```

```
<210> SEQ ID NO 7
<211> LENGTH: 226
<212> TYPE: PRT
<213> ORGANISM: Artificial Sequence
<220> FEATURE:
<223> OTHER INFORMATION: IgG1 Fc 297A mutant

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 8
<211> LENGTH: 226
<212> TYPE: PRT
<213> ORGANISM: Artificial Sequence
<220> FEATURE:
<223> OTHER INFORMATION: IgG1 Fc T366Y mutant

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80
```

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Tyr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly
225

<210> SEQ ID NO 9
<211> LENGTH: 226
<212> TYPE: PRT
<213> ORGANISM: Artificial Sequence
<220> FEATURE:
<223> OTHER INFORMATION: IgG1 Fc Y407T mutant

<400> SEQUENCE: 9

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Ala Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Thr Ser Lys Leu Thr Val
            180                 185                 190
Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
    210                 215                 220

Pro Gly
225

<210> SEQ ID NO 10
<211> LENGTH: 159
<212> TYPE: PRT
<213> ORGANISM: Homo sapiens

<400> SEQUENCE: 10

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
            100                 105                 110

His Ser Asn Cys Val Ser Phe Glu Cys Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr
145                 150                 155

<210> SEQ ID NO 11
<211> LENGTH: 159
<212> TYPE: PRT
<213> ORGANISM: Artificial Sequence
<220> FEATURE:
<223> OTHER INFORMATION: IL33 C208S, C227S, C232S, C259S mutant

<400> SEQUENCE: 11

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Ser Glu Lys Pro Leu Pro Asp Gln Ala Phe Phe Val Leu His Asn Met
            100                 105                 110

His Ser Asn Ser Val Ser Phe Glu Ser Lys Thr Asp Pro Gly Val Phe
        115                 120                 125

Ile Gly Val Lys Asp Asn His Leu Ala Leu Ile Lys Val Asp Ser Ser

```
            130                 135                 140
Glu Asn Leu Ser Thr Glu Asn Ile Leu Phe Lys Leu Ser Glu Thr
145                 150                 155

<210> SEQ ID NO 12
<211> LENGTH: 374
<212> TYPE: PRT
<213> ORGANISM: Artificial Sequence
<220> FEATURE:
<223> OTHER INFORMATION: IL2vN Fc chain

<400> SEQUENCE: 12

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Ser Gly Gly Gly Gly Ser Gly
    130                 135                 140

Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Val Tyr Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Ala Leu Val Ser
                325                 330                 335

Lys Leu Thr Val Asp Lys Ser Arg Trp Gln Gln Gly Asn Val Phe Ser
```

```
                      340                 345                 350
Cys Ser Val Met His Glu Ala Leu His Asn His Tyr Thr Gln Lys Ser
            355                 360                 365

Leu Ser Leu Ser Pro Gly
        370

<210> SEQ ID NO 13
<211> LENGTH: 400
<212> TYPE: PRT
<213> ORGANISM: Artificial Sequence
<220> FEATURE:
<223> OTHER INFORMATION: IL-33 Fc fusion protein

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Val Leu Pro Pro Ser Arg Asp Glu Leu Thr Lys Asn Gln Val Ser
130                 135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Gly Ser Gly Gly Gly Gly
225                 230                 235                 240

Ser Ser Ile Thr Gly Ile Ser Pro Ile Thr Glu Tyr Leu Ala Ser Leu
                245                 250                 255

Ser Thr Tyr Asn Asp Gln Ser Ile Thr Phe Ala Leu Glu Asp Glu Ser
            260                 265                 270

Tyr Glu Ile Tyr Val Glu Asp Leu Lys Lys Asp Glu Lys Lys Asp Lys
        275                 280                 285

Val Leu Leu Ser Tyr Tyr Glu Ser Gln His Pro Ser Asn Glu Ser Gly
290                 295                 300

Asp Gly Val Asp Gly Lys Met Leu Met Val Thr Leu Ser Pro Thr Lys
305                 310                 315                 320

Asp Phe Trp Leu His Ala Asn Asn Lys Glu His Ser Val Glu Leu His
```

```
                325                 330                 335
Lys Ser Glu Lys Pro Leu Pro Asp Gln Ala Phe Phe Val Leu His Asn
            340                 345                 350

Met His Ser Asn Ser Val Ser Phe Glu Ser Lys Thr Asp Pro Gly Val
            355                 360                 365

Phe Ile Gly Val Lys Asp Asn His Leu Ala Leu Ile Lys Val Asp Ser
            370                 375                 380

Ser Glu Asn Leu Ser Thr Glu Asn Ile Leu Phe Lys Leu Ser Glu Thr
385                 390                 395                 400

<210> SEQ ID NO 14
<211> LENGTH: 374
<212> TYPE: PRT
<213> ORGANISM: Artificial Sequence
<220> FEATURE:
<223> OTHER INFORMATION: IL-2 Fc fusion protein

<400> SEQUENCE: 14

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Gly Ser Gly Gly Gly Gly Ser Gly
130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Val Leu Pro Pro Ser Arg Asp Glu Leu Thr Lys
        275                 280                 285

Asn Gln Val Ser Leu Leu Cys Leu Val Lys Gly Phe Tyr Pro Ser Asp
```

```
                 290                 295                 300

Ile Ala Val Glu Trp Glu Ser Asn Gly Gln Pro Glu Asn Asn Tyr Leu
305                 310                 315                 320

Thr Trp Pro Pro Val Leu Asp Ser Asp Gly Ser Phe Phe Leu Tyr Ser
                    325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly
    370

<210> SEQ ID NO 15
<211> LENGTH: 400
<212> TYPE: PRT
<213> ORGANISM: Artificial Sequence
<220> FEATURE:
<223> OTHER INFORMATION: IL33 Fc fusion protein

<400> SEQUENCE: 15

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
                20                  25                  30

Glu Ile Tyr Val Glu Asp Leu Lys Lys Asp Glu Lys Lys Asp Lys Val
            35                  40                  45

Leu Leu Ser Tyr Tyr Glu Ser Gln His Pro Ser Asn Glu Ser Gly Asp
50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Ser Glu Lys Pro Leu Pro Asp Gln Ala Phe Phe Val Leu His Asn Met
                100                 105                 110

His Ser Asn Ser Val Ser Phe Glu Ser Lys Thr Asp Pro Gly Val Phe
            115                 120                 125

Ile Gly Val Lys Asp Asn His Leu Ala Leu Ile Lys Val Asp Ser Ser
130                 135                 140

Glu Asn Leu Ser Thr Glu Asn Ile Leu Phe Lys Leu Ser Glu Thr Gly
145                 150                 155                 160

Gly Gly Gly Ser Gly Gly Gly Ser Gly Gly Gly Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Ala Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
```

```
                275                 280                 285
Thr Ile Ser Lys Ala Lys Gly Gln Pro Arg Glu Pro Gln Val Tyr Val
290                 295                 300

Tyr Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Ala Leu Val Ser Lys Leu Thr Val Asp Lys
        355                 360                 365

Ser Arg Trp Gln Gln Gly Asn Val Phe Ser Cys Ser Val Met His Glu
370                 375                 380

Ala Leu His Asn His Tyr Thr Gln Lys Ser Leu Ser Leu Ser Pro Gly
385                 390                 395                 400

<210> SEQ ID NO 16
<211> LENGTH: 374
<212> TYPE: PRT
<213> ORGANISM: Artificial Sequence
<220> FEATURE:
<223> OTHER INFORMATION: IL2 Fc fusion protein

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Val Leu Pro Pro Ser Arg Asp Glu Leu Thr Lys Asn Gln Val Ser
    130                 135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Ala Pro Thr Ser Ser Ser Thr Lys Lys Thr Gln Leu Gln Leu Glu
```

```
              245                 250                 255
His Leu Leu Asp Leu Gln Met Ile Leu Asn Gly Ile Asn Asn Tyr
        260                 265                 270

Lys Asn Pro Lys Leu Thr Arg Met Leu Thr Phe Lys Phe Tyr Met Pro
        275                 280                 285

Lys Lys Ala Thr Glu Leu Lys His Leu Gln Cys Leu Glu Glu Glu Leu
        290                 295                 300

Lys Pro Leu Glu Glu Val Leu Asn Leu Ala Gln Ser Lys Asn Phe His
305                 310                 315                 320

Leu Arg Pro Arg Asp Leu Ile Ser Arg Ile Asn Val Ile Val Leu Glu
                325                 330                 335

Leu Lys Gly Ser Glu Thr Thr Phe Met Cys Glu Tyr Ala Asp Glu Thr
                340                 345                 350

Ala Thr Ile Val Glu Phe Leu Asn Arg Trp Ile Thr Phe Ser Gln Ser
                355                 360                 365

Ile Ile Ser Thr Leu Thr
        370

<210> SEQ ID NO 17
<211> LENGTH: 548
<212> TYPE: PRT
<213> ORGANISM: Artificial Sequence
<220> FEATURE:
<223> OTHER INFORMATION: IL33 Fc IL2 fusion protein

<400> SEQUENCE: 17

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Ser Glu Lys Pro Leu Pro Asp Gln Ala Phe Phe Val Leu His Asn Met
            100                 105                 110

His Ser Asn Ser Val Ser Phe Glu Ser Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Ser Thr Glu Asn Ile Leu Phe Lys Leu Ser Glu Thr Gly
145                 150                 155                 160

Gly Gly Gly Ser Gly Gly Gly Gly Ser Gly Gly Gly Gly Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
```

```
                225                 230                 235                 240
    Ala Lys Thr Lys Pro Arg Glu Glu Gln Tyr Ala Ser Thr Tyr Arg Val
                        245                 250                 255

Val Ser Val Leu Thr Val Leu His Gln Asp Trp Leu Asn Gly Lys Glu
                        260                 265                 270

Tyr Lys Cys Lys Val Ser Asn Lys Ala Leu Pro Ala Pro Ile Glu Lys
                        275                 280                 285

Thr Ile Ser Lys Ala Lys Gly Gln Pro Arg Glu Pro Gln Val Tyr Val
                290                 295                 300

Leu Pro Pro Ser Arg Asp Glu Leu Thr Lys Asn Gln Val Ser Leu Leu
    305                 310                 315                 320

Cys Leu Val Lys Gly Phe Tyr Pro Ser Asp Ile Ala Val Glu Trp Glu
                        325                 330                 335

Ser Asn Gly Gln Pro Glu Asn Asn Tyr Leu Thr Trp Pro Pro Val Leu
                        340                 345                 350

Asp Ser Asp Gly Ser Phe Phe Leu Tyr Ser Lys Leu Thr Val Asp Lys
                        355                 360                 365

Ser Arg Trp Gln Gln Gly Asn Val Phe Ser Cys Ser Val Met His Glu
                370                 375                 380

Ala Leu His Asn His Tyr Thr Gln Lys Ser Leu Ser Leu Ser Pro Gly
    385                 390                 395                 400

Gly Gly Gly Gly Ser Gly Gly Gly Ser Gly Gly Gly Gly Ser Ala
                        405                 410                 415

Pro Thr Ser Ser Ser Thr Lys Lys Thr Gln Leu Gln Leu Glu His Leu
                        420                 425                 430

Leu Leu Asp Leu Gln Met Ile Leu Asn Gly Ile Asn Asn Tyr Lys Asn
                        435                 440                 445

Pro Lys Leu Thr Arg Met Leu Thr Phe Lys Phe Tyr Met Pro Lys Lys
                        450                 455                 460

Ala Thr Glu Leu Lys His Leu Gln Cys Leu Glu Glu Glu Leu Lys Pro
    465                 470                 475                 480

Leu Glu Glu Val Leu Asn Leu Ala Gln Ser Lys Asn Phe His Leu Arg
                        485                 490                 495

Pro Arg Asp Leu Ile Ser Arg Ile Asn Val Ile Val Leu Glu Leu Lys
                        500                 505                 510

Gly Ser Glu Thr Thr Phe Met Cys Glu Tyr Ala Asp Glu Thr Ala Thr
                        515                 520                 525

Ile Val Glu Phe Leu Asn Arg Trp Ile Thr Phe Ser Gln Ser Ile Ile
                530                 535                 540

Ser Thr Leu Thr
    545

<210> SEQ ID NO 18
<211> LENGTH: 548
<212> TYPE: PRT
<213> ORGANISM: Artificial Sequence
<220> FEATURE:
<223> OTHER INFORMATION: IL2 Fc IL33 fusion protein

<400> SEQUENCE: 18

Ala Pro Thr Ser Ser Ser Thr Lys Lys Thr Gln Leu Gln Leu Glu His
    1               5                   10                  15

Leu Leu Leu Asp Leu Gln Met Ile Leu Asn Gly Ile Asn Asn Tyr Lys
                    20                  25                  30

Asn Pro Lys Leu Thr Arg Met Leu Thr Phe Lys Phe Tyr Met Pro Lys
```

```
            35                  40                  45
Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
    130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Val Leu Pro Pro Ser Arg Asp Glu Leu Thr Lys
        275                 280                 285

Asn Gln Val Ser Leu Leu Cys Leu Val Lys Gly Phe Tyr Pro Ser Asp
290                 295                 300

Ile Ala Val Glu Trp Glu Ser Asn Gly Gln Pro Glu Asn Asn Tyr Leu
305                 310                 315                 320

Thr Trp Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Gly Gly Gly Ser Gly Gly Gly Gly Ser
370                 375                 380

Gly Gly Gly Gly Ser Ser Ile Thr Gly Ile Ser Pro Ile Thr Glu Tyr
385                 390                 395                 400

Leu Ala Ser Leu Ser Thr Tyr Asn Asp Gln Ser Ile Thr Phe Ala Leu
                405                 410                 415

Glu Asp Glu Ser Tyr Glu Ile Tyr Val Glu Asp Leu Lys Lys Asp Glu
            420                 425                 430

Lys Lys Asp Lys Val Leu Leu Ser Tyr Tyr Glu Ser Gln His Pro Ser
        435                 440                 445

Asn Glu Ser Gly Asp Gly Val Asp Gly Lys Met Leu Met Val Thr Leu
450                 455                 460
```

```
Ser Pro Thr Lys Asp Phe Trp Leu His Ala Asn Asn Lys Glu His Ser
465                 470                 475                 480

Val Glu Leu His Lys Ser Glu Lys Pro Leu Pro Asp Gln Ala Phe Phe
            485                 490                 495

Val Leu His Asn Met His Ser Asn Ser Val Ser Phe Glu Ser Lys Thr
        500                 505                 510

Asp Pro Gly Val Phe Ile Gly Val Lys Asp Asn His Leu Ala Leu Ile
            515                 520                 525

Lys Val Asp Ser Ser Glu Asn Leu Ser Thr Glu Asn Ile Leu Phe Lys
530                 535                 540

Leu Ser Glu Thr
545

<210> SEQ ID NO 19
<211> LENGTH: 548
<212> TYPE: PRT
<213> ORGANISM: Artificial Sequence
<220> FEATURE:
<223> OTHER INFORMATION: IL33 Fc IL2 fusion protein

<400> SEQUENCE: 19

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Ser Glu Lys Pro Leu Pro Asp Gln Ala Phe Phe Val Leu His Asn Met
            100                 105                 110

His Ser Asn Ser Val Ser Phe Glu Ser Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Ser Thr Glu Asn Ile Leu Phe Lys Leu Ser Glu Thr Gly
145                 150                 155                 160

Gly Gly Gly Ser Gly Gly Gly Ser Gly Gly Gly Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Ala Ser Thr Tyr Arg Val
                245                 250                 255

Val Ser Val Leu Thr Val Leu His Gln Asp Trp Leu Asn Gly Lys Glu
            260                 265                 270
```

```
Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
                355                 360                 365

Ser Arg Trp Gln Gln Gly Asn Val Phe Ser Cys Ser Val Met His Glu
370                 375                 380

Ala Leu His Asn His Tyr Thr Gln Lys Ser Leu Ser Leu Ser Pro Gly
385                 390                 395                 400

Gly Gly Gly Gly Ser Gly Gly Gly Ser Gly Gly Gly Gly Ser Gly Ala
                405                 410                 415

Pro Thr Ser Ser Ser Thr Lys Lys Thr Gln Leu Gln Leu Glu His Leu
                420                 425                 430

Leu Leu Asp Leu Gln Met Ile Leu Asn Gly Ile Asn Asn Tyr Lys Asn
            435                 440                 445

Pro Lys Leu Thr Arg Met Leu Thr Phe Lys Phe Tyr Met Pro Lys Lys
450                 455                 460

Ala Thr Glu Leu Lys His Leu Gln Cys Leu Glu Glu Leu Lys Pro
465                 470                 475                 480

Leu Glu Glu Val Leu Asn Leu Ala Gln Ser Lys Asn Phe His Leu Arg
                485                 490                 495

Pro Arg Asp Leu Ile Ser Arg Ile Asn Val Ile Val Leu Glu Leu Lys
                500                 505                 510

Gly Ser Glu Thr Thr Phe Met Cys Glu Tyr Ala Asp Glu Thr Ala Thr
            515                 520                 525

Ile Val Glu Phe Leu Asn Arg Trp Ile Thr Phe Ser Gln Ser Ile Ile
530                 535                 540

Ser Thr Leu Thr
545

<210> SEQ ID NO 20
<211> LENGTH: 548
<212> TYPE: PRT
<213> ORGANISM: Artificial Sequence
<220> FEATURE:
<223> OTHER INFORMATION: IL2 Fc IL33 fusion protein

<400> SEQUENCE: 20

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Arg Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr Gly Gly Gly Ser Gly Gly Gly Ser Gly
130                 135                 140
Gly Gly Gly Ser Asp Lys Thr His Thr Cys Pro Pro Cys Pro Ala Pro
145                 150                 155                 160
Glu Leu Leu Gly Gly Pro Ser Val Phe Leu Phe Pro Pro Lys Pro Lys
                165                 170                 175
Asp Thr Leu Met Ile Ser Arg Thr Pro Glu Val Thr Cys Val Val Val
            180                 185                 190
Asp Val Ser His Glu Asp Pro Glu Val Lys Phe Asn Trp Tyr Val Asp
        195                 200                 205
Gly Val Glu Val His Asn Ala Lys Thr Lys Pro Arg Glu Glu Gln Tyr
210                 215                 220
Ala Ser Thr Tyr Arg Val Val Ser Val Leu Thr Val Leu His Gln Asp
225                 230                 235                 240
Trp Leu Asn Gly Lys Glu Tyr Lys Cys Lys Val Ser Asn Lys Ala Leu
                245                 250                 255
Pro Ala Pro Ile Glu Lys Thr Ile Ser Lys Ala Lys Gly Gln Pro Arg
            260                 265                 270
Glu Pro Gln Val Tyr Thr Leu Pro Pro Ser Arg Asp Glu Leu Thr Lys
        275                 280                 285
Asn Gln Val Ser Leu Thr Cys Leu Val Lys Gly Phe Tyr Pro Ser Asp
290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Lys Leu Thr Val Asp Lys Ser Arg Trp Gln Gln Gly Asn Val Phe Ser
            340                 345                 350
Cys Ser Val Met His Glu Ala Leu His Asn His Tyr Thr Gln Lys Ser
        355                 360                 365
Leu Ser Leu Ser Pro Gly Gly Gly Gly Ser Gly Gly Gly Gly Ser
370                 375                 380
Gly Gly Gly Gly Ser Ser Ile Thr Gly Ile Ser Pro Ile Thr Glu Tyr
385                 390                 395                 400
Leu Ala Ser Leu Ser Thr Tyr Asn Asp Gln Ser Ile Thr Phe Ala Leu
                405                 410                 415
Glu Asp Glu Ser Tyr Glu Ile Tyr Val Glu Asp Leu Lys Lys Asp Glu
            420                 425                 430
Lys Lys Asp Lys Val Leu Leu Ser Tyr Tyr Glu Ser Gln His Pro Ser
        435                 440                 445
Asn Glu Ser Gly Asp Gly Val Asp Gly Lys Met Leu Met Val Thr Leu
450                 455                 460
Ser Pro Thr Lys Asp Phe Trp Leu His Ala Asn Asn Lys Glu His Ser
465                 470                 475                 480
Val Glu Leu His Lys Ser Glu Lys Pro Leu Pro Asp Gln Ala Phe Phe
                485                 490                 495
```

```
Val Leu His Asn Met His Ser Asn Ser Val Ser Phe Glu Ser Lys Thr
            500                 505                 510

Asp Pro Gly Val Phe Ile Gly Val Lys Asp Asn His Leu Ala Leu Ile
        515                 520                 525

Lys Val Asp Ser Ser Glu Asn Leu Ser Thr Glu Asn Ile Leu Phe Lys
530                 535                 540

Leu Ser Glu Thr
545

<210> SEQ ID NO 21
<211> LENGTH: 400
<212> TYPE: PRT
<213> ORGANISM: Artificial Sequence
<220> FEATURE:
<223> OTHER INFORMATION: IL33 Fc fusion protein

<400> SEQUENCE: 21

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Ser Glu Lys Pro Leu Pro Asp Gln Ala Phe Phe Val Leu His Asn Met
            100                 105                 110

His Ser Asn Ser Val Ser Phe Glu Ser Lys Thr Asp Pro Gly Val Phe
        115                 120                 125

Ile Gly Val Lys Asp Asn His Leu Ala Leu Ile Lys Val Asp Ser Ser
130                 135                 140

Glu Asn Leu Ser Thr Glu Asn Ile Leu Phe Lys Leu Ser Glu Thr Gly
145                 150                 155                 160

Gly Gly Gly Ser Gly Gly Gly Gly Ser Gly Gly Gly Gly Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Ala Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
290                 295                 300
```

```
Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
            325                 330                 335

Ser Asn Gly Gln Pro Glu Asn Asn Tyr Lys Thr Thr Pro Pro Val Leu
        340                 345                 350

Asp Ser Asp Gly Ser Phe Phe Leu Tyr Ser Lys Leu Thr Val Asp Lys
    355                 360                 365

Ser Arg Trp Gln Gln Gly Asn Val Phe Ser Cys Ser Val Met His Glu
370                 375                 380

Ala Leu His Asn His Tyr Thr Gln Lys Ser Leu Ser Leu Ser Pro Gly
385                 390                 395                 400

<210> SEQ ID NO 22
<211> LENGTH: 598
<212> TYPE: PRT
<213> ORGANISM: Artificial Sequence
<220> FEATURE:
<223> OTHER INFORMATION: Ab2HeavyIL2vC

<400> SEQUENCE: 22

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asn Ser Asp Thr Arg Phe Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Thr Ser Ser Asp Tyr Tyr Gly Leu Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

Glu Asp Pro Glu Val Lys Phe Asn Trp Tyr Val Asp Gly Val Glu Val
            275                 280                 285

His Asn Ala Lys Thr Lys Pro Arg Glu Gln Tyr Ala Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Ser Gly Gly Gly Gly
    450                 455                 460

Ser Ala Pro Thr Ser Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495

Lys Asn Pro Lys Leu Thr Arg Met Leu Thr Phe Lys Phe Tyr Met Pro
            500                 505                 510

Lys Lys Ala Thr Glu Leu Lys His Leu Gln Cys Leu Glu Glu Glu Leu
        515                 520                 525

Lys Pro Leu Glu Glu Val Leu Asn Leu Ala Gln Ser Lys Asn Phe His
    530                 535                 540

Leu Arg Pro Arg Asp Leu Ile Ser Arg Ile Asn Val Ile Val Leu Glu
545                 550                 555                 560

Leu Lys Gly Ser Glu Thr Thr Phe Met Cys Glu Tyr Ala Asp Glu Thr
                565                 570                 575

Ala Thr Ile Val Glu Phe Leu Asn Arg Trp Ile Thr Phe Ser Gln Ser
            580                 585                 590

Ile Ile Ser Thr Leu Thr
        595

<210> SEQ ID NO 23
<211> LENGTH: 594
<212> TYPE: PRT
<213> ORGANISM: Artificial Sequence
<220> FEATURE:
<223> OTHER INFORMATION: Ab4HeavyIL2vC

<400> SEQUENCE: 23

Gln Val Gln Leu Val Gln Ser Gly Ala Glu Val Lys Lys Pro Gly Ala
1               5                   10                  15

Ser Val Lys Val Ser Cys Glu Val Ser Gly Phe Ile Leu Thr Glu Leu
            20                  25                  30

```
Ser Val Asn Trp Val Arg Gln Ala Pro Gly Lys Gly Leu Glu Trp Met
         35                  40                  45

Gly Gly Phe Asp Pro Glu Asp Gly Lys Thr Ile Tyr Ala Gln Lys Phe
 50                  55                  60

Gln Gly Arg Val Thr Leu Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Trp Trp Asp Phe His Phe Asp Phe Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Ala Pro Thr
```

```
                    450              455              460
Ser Ser Ser Thr Lys Lys Thr Gln Leu Gln Leu Glu His Leu Leu Leu
465                 470              475              480

Asp Leu Gln Met Ile Leu Asn Gly Ile Asn Asn Tyr Lys Asn Pro Lys
                485              490              495

Leu Thr Arg Met Leu Thr Phe Lys Phe Tyr Met Pro Lys Lys Ala Thr
            500              505              510

Glu Leu Lys His Leu Gln Cys Leu Glu Glu Leu Lys Pro Leu Glu
            515              520              525

Glu Val Leu Asn Leu Ala Gln Ser Lys Asn Phe His Leu Arg Pro Arg
            530              535              540

Asp Leu Ile Ser Arg Ile Asn Val Ile Val Leu Glu Leu Lys Gly Ser
545             550              555              560

Glu Thr Thr Phe Met Cys Glu Tyr Ala Asp Glu Thr Ala Thr Ile Val
                565              570              575

Glu Phe Leu Asn Arg Trp Ile Thr Phe Ser Gln Ser Ile Ile Ser Thr
                580              585              590

Leu Thr

<210> SEQ ID NO 24
<211> LENGTH: 598
<212> TYPE: PRT
<213> ORGANISM: Artificial Sequence
<220> FEATURE:
<223> OTHER INFORMATION: Ab2HeavyIL2vC(W)

<400> SEQUENCE: 24

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asn Ser Asp Thr Arg Phe Ser Pro Ser Phe
50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Thr Ser Ser Asp Tyr Tyr Gly Leu Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220
```

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
            355                 360                 365

Leu Leu Cys Leu Val Lys Gly Phe Tyr Pro Ser Asp Ile Ala Val Glu
370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Gly Gly Gly Ser Gly Gly Gly Ser Gly Gly Gly Gly
450                 455                 460

Ser Ala Pro Thr Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
            485                 490                 495

Lys Asn Pro Lys Leu Thr Arg Met Leu Thr Phe Lys Phe Tyr Met Pro
            500                 505                 510

Lys Lys Ala Thr Glu Leu Lys His Leu Gln Cys Leu Glu Glu Glu Leu
            515                 520                 525

Lys Pro Leu Glu Glu Val Leu Asn Leu Ala Gln Ser Lys Asn Phe His
            530                 535                 540

Leu Arg Pro Arg Asp Leu Ile Ser Arg Ile Asn Val Ile Val Leu Glu
545                 550                 555                 560

Leu Lys Gly Ser Glu Thr Thr Phe Met Cys Glu Tyr Ala Asp Glu Thr
            565                 570                 575

Ala Thr Ile Val Glu Phe Leu Asn Arg Trp Ile Thr Phe Ser Gln Ser
            580                 585                 590

Ile Ile Ser Thr Leu Thr
        595

<210> SEQ ID NO 25
<211> LENGTH: 594
<212> TYPE: PRT
<213> ORGANISM: Artificial Sequence
<220> FEATURE:

<223> OTHER INFORMATION: Ab4HeavyIL2vC(W)

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Glu Val Ser Gly Phe Ile Leu Thr Glu Leu
            20                  25                  30

Ser Val Asn Trp Val Arg Gln Ala Pro Gly Lys Gly Leu Glu Trp Met
        35                  40                  45

Gly Gly Phe Asp Pro Glu Asp Gly Lys Thr Ile Tyr Ala Gln Lys Phe
    50                  55                  60

Gln Gly Arg Val Thr Leu Thr Glu Asp Thr Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Thr Trp Trp Asp Phe His Phe Asp Phe Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Val Leu Pro
            340                 345                 350

Pro Ser Arg Asp Glu Leu Thr Lys Asn Gln Val Ser Leu Leu Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Leu Thr Trp Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Gly Gly Gly Ser Ala Pro Thr
    450                 455                 460

Ser Ser Ser Thr Lys Lys Thr Gln Leu Gln Leu Glu His Leu Leu Leu
465                 470                 475                 480

Asp Leu Gln Met Ile Leu Asn Gly Ile Asn Asn Tyr Lys Asn Pro Lys
                485                 490                 495

Leu Thr Arg Met Leu Thr Phe Lys Phe Tyr Met Pro Lys Lys Ala Thr
            500                 505                 510

Glu Leu Lys His Leu Gln Cys Leu Glu Glu Leu Lys Pro Leu Glu
        515                 520                 525

Glu Val Leu Asn Leu Ala Gln Ser Lys Asn Phe His Leu Arg Pro Arg
    530                 535                 540

Asp Leu Ile Ser Arg Ile Asn Val Ile Val Leu Glu Leu Lys Gly Ser
545                 550                 555                 560

Glu Thr Thr Phe Met Cys Glu Tyr Ala Asp Glu Thr Ala Thr Ile Val
                565                 570                 575

Glu Phe Leu Asn Arg Trp Ile Thr Phe Ser Gln Ser Ile Ile Ser Thr
            580                 585                 590

Leu Thr

<210> SEQ ID NO 26
<211> LENGTH: 450
<212> TYPE: PRT
<213> ORGANISM: Artificial Sequence
<220> FEATURE:
<223> OTHER INFORMATION: Ab2Heavy(V)

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asn Ser Asp Thr Arg Phe Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Thr Ser Ser Asp Tyr Tyr Gly Leu Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
            165                 170                 175
Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 27
<211> LENGTH: 446
<212> TYPE: PRT
<213> ORGANISM: Artificial Sequence
<220> FEATURE:
<223> OTHER INFORMATION: Ab4Heavy(V)

<400> SEQUENCE: 27

Gln Val Gln Leu Val Gln Ser Gly Ala Glu Val Lys Lys Pro Gly Ala
1               5                   10                  15

Ser Val Lys Val Ser Cys Glu Val Ser Gly Phe Ile Leu Thr Glu Leu
            20                  25                  30

Ser Val Asn Trp Val Arg Gln Ala Pro Gly Lys Gly Leu Glu Trp Met
        35                  40                  45

Gly Gly Phe Asp Pro Glu Asp Gly Lys Thr Ile Tyr Ala Gln Lys Phe
    50                  55                  60

Gln Gly Arg Val Thr Leu Thr Glu Asp Thr Ser Thr Asp Thr Ala Tyr
```

```
            65                  70                  75                  80
        Met Glu Leu Ser Ser Leu Arg Ser Glu Asp Thr Ala Val Tyr Tyr Cys
                        85                  90                  95

Ala Thr Trp Trp Asp Phe His Phe Asp Phe Trp Gly Gln Gly Thr Leu
                    100                 105                 110

Val Thr Val Ser Ser Ala Ser Thr Lys Gly Pro Ser Val Phe Pro Leu
                    115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
        145                 150                 155                 160

Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                    180                 185                 190

Leu Gly Thr Gln Thr Tyr Ile Cys Asn Val Asn His Lys Pro Ser Asn
                    195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
        225                 230                 235                 240

Phe Leu Phe Pro Pro Lys Pro Lys Asp Thr Leu Met Ile Ser Arg Thr
                        245                 250                 255

Pro Glu Val Thr Cys Val Val Val Asp Val Ser His Glu Asp Pro Glu
                    260                 265                 270

Val Lys Phe Asn Trp Tyr Val Asp Gly Val Glu Val His Asn Ala Lys
                    275                 280                 285

Thr Lys Pro Arg Glu Glu Gln Tyr Ala Ser Thr Tyr Arg Val Val Ser
            290                 295                 300

Val Leu Thr Val Leu His Gln Asp Trp Leu Asn Gly Lys Glu Tyr Lys
        305                 310                 315                 320

Cys Lys Val Ser Asn Lys Ala Leu Pro Ala Pro Ile Glu Lys Thr Ile
                        325                 330                 335

Ser Lys Ala Lys Gly Gln Pro Arg Glu Pro Gln Val Tyr Val Tyr Pro
                    340                 345                 350

Pro Ser Arg Asp Glu Leu Thr Lys Asn Gln Val Ser Leu Thr Cys Leu
                    355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
        385                 390                 395                 400

Asp Gly Ser Phe Ala Leu Val Ser Lys Leu Thr Val Asp Lys Ser Arg
                        405                 410                 415

Trp Gln Gln Gly Asn Val Phe Ser Cys Ser Val Met His Glu Ala Leu
                    420                 425                 430

His Asn His Tyr Thr Gln Lys Ser Leu Ser Leu Ser Pro Gly
                    435                 440                 445

<210> SEQ ID NO 28
<211> LENGTH: 374
<212> TYPE: PRT
<213> ORGANISM: Artificial Sequence
<220> FEATURE:
<223> OTHER INFORMATION: IL2vCFc(V)
```

<400> SEQUENCE: 28

```
Asp Lys Thr His Thr Cys Pro Cys Pro Ala Pro Glu Leu Leu Gly
1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Val Tyr Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Ala Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Gly Gly Gly Gly
225                 230                 235                 240

Ser Ala Pro Thr Ser Ser Thr Lys Lys Thr Gln Leu Gln Leu Glu
            245                 250                 255

His Leu Leu Leu Asp Leu Gln Met Ile Leu Asn Gly Ile Asn Asn Tyr
                260                 265                 270

Lys Asn Pro Lys Leu Thr Arg Met Leu Thr Phe Lys Phe Tyr Met Pro
            275                 280                 285

Lys Lys Ala Thr Glu Leu Lys His Leu Gln Cys Leu Glu Glu Glu Leu
290                 295                 300

Lys Pro Leu Glu Glu Val Leu Asn Leu Ala Gln Ser Lys Asn Phe His
305                 310                 315                 320

Leu Arg Pro Arg Asp Leu Ile Ser Arg Ile Asn Val Ile Val Leu Glu
                325                 330                 335

Leu Lys Gly Ser Glu Thr Thr Phe Met Cys Glu Tyr Ala Asp Glu Thr
            340                 345                 350

Ala Thr Ile Val Glu Phe Leu Asn Arg Trp Ile Thr Phe Ser Gln Ser
        355                 360                 365

Ile Ile Ser Thr Leu Thr
        370
```

<210> SEQ ID NO 29
<211> LENGTH: 214
<212> TYPE: PRT
<213> ORGANISM: Artificial Sequence
<220> FEATURE:
<223> OTHER INFORMATION: Ab2Kappa

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Asn Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 219
<212> TYPE: PRT
<213> ORGANISM: Artificial Sequence
<220> FEATURE:
<223> OTHER INFORMATION: Ab4Kappa

<400> SEQUENCE: 30

Asp Phe Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asn Gly Lys Thr Tyr Leu Tyr Trp Phe Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu

```
                115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 31
<211> LENGTH: 5
<212> TYPE: PRT
<213> ORGANISM: Artificial Sequence
<220> FEATURE:
<223> OTHER INFORMATION: Peptide Linker

<400> SEQUENCE: 31

Gly Gly Gly Gly Ser
1               5
```

MULTIVALENT REGULATORY T CELL MODULATORS

RELATED APPLICATIONS

This application claims priority to U.S. Provisional Patent Application No. 62/433,533 filed on Dec. 13, 2016, the contents of which are incorporated herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 127754_00502_Revised_Sequence_Listing. The size of the text file is 91 KB, and the text file was created on Jan. 8, 2018.

BACKGROUND OF THE INVENTION

Inflammatory myopathies are conditions that are characterized by chronic muscle inflammation and muscle weakness. Muscular dystrophies are degenerative muscle diseases caused by a mutated dystrophin gene, but an underlying cause of the progressive degeneration is muscle inflammation. The inflammation associated with these diseases can damage muscle fibers, causing fatigue, pain, and progressive muscle degeneration. Regulatory T cells (Tregs) are a specialized subset of T cells. Tregs suppress activation of the immune system and thereby regulate the self-tolerance of the immune system. Subsets of Tregs expressing defined molecular markers, such as the receptor ST2, are found in inflamed tissues, such as injured skeletal muscle and inflamed lungs. Expansion and activation of ST2-expressing Tregs have been implicated in the resolution of acute muscle injury and of muscle inflammation associated with muscular dystrophy. Additionally, ST2+ Tregs are found in tissues such as visceral adipose, colon, and lung, and possess immunoregulatory and tissue repair functions in those tissues.

SUMMARY OF THE INVENTION

In some embodiments, the present disclosure provides a fusion protein comprising: a human IL-2 protein domain; an immunoglobulin Fc protein domain; and a protein domain that binds to Interleukin 1 receptor-like 1 (ST2). In certain embodiments, the protein domain that binds to ST2 is a human IL-33 protein domain. In certain embodiments, the protein domain that binds to ST2 is an antibody specific for ST2, or an antigen-binding fragment thereof. In certain embodiments, the fusion protein comprises at least one peptide linker domain. In certain embodiments, the human IL-2 protein domain comprises human IL-2 with a substitution selected from the group consisting of: T3A, N88R, N88G, D20H, C125S, Q126L, and Q126F, relative to the amino acid sequence of SEQ ID NO: 2. In certain embodiments, the immunoglobulin Fc protein domain comprises an amino acid sequence selected from the group consisting of the human IgG1 Fc variant of SEQ ID NO: 4, SEQ ID NO: 5, SEQ ID NO: 7, SEQ ID NO: 8 or SEQ ID NO: 9. In certain embodiments, the human IL-33 protein domain comprises human IL-33 with a substitution selected from the group consisting of C208S, C227S, C232S and C259S, relative to the amino acid sequence of SEQ ID NO: 10. In certain embodiments, the peptide linker domain comprises the amino acid sequence of SEQ ID NO: 6. In certain embodiments, the fusion protein further comprises a first peptide linker domain and a second peptide linker domain.

In certain embodiments of the fusion proteins described herein, each domain has an amino-terminus (N-terminus) and a carboxy terminus (C-terminus); and wherein the fusion protein is configured so that the C-terminus of the human IL-2 protein domain is fused through a peptide bond to the N-terminus of the first peptide linker domain; the N-terminus of the IgG Fc protein domain is fused through a peptide bond to the C-terminus of the first peptide linker domain; the N-terminus of the second peptide linker domain is fused through a peptide bond to the C-terminus of the IgG Fc protein domain; and the N-terminus of the protein domain that binds to ST2 is fused through a peptide bond to the C-terminus of the second peptide linker domain.

In certain embodiments of the fusion proteins described herein, each domain has an amino-terminus (N-terminus) and a carboxy terminus (C-terminus); and wherein the fusion protein is configured so that the C-terminus of the protein domain that binds to ST2 is fused through a peptide bond to the N-terminus of the first peptide linker domain; the N-terminus of the IgG Fc protein domain is fused through a peptide bond to the C-terminus of the first peptide linker domain; the N-terminus of the second peptide linker domain is fused through a peptide bond to the C-terminus of the IgG Fc protein domain; and the N-terminus of the human IL-2 protein domain is fused through a peptide bond to the C-terminus of the second peptide linker domain. In certain embodiments, the fusion protein comprises the amino acid sequence of SEQ ID NO: 17, SEQ ID NO: 18, SEQ ID NO: 19, SEQ ID NO: 20, SEQ ID NO: 22, SEQ ID NO: 23, SEQ ID NO: 24, or SEQ ID NO: 25.

In some embodiments, the present disclosure provides a nucleic acid encoding a fusion protein described herein. In some embodiments, the present disclosure provides a dimeric protein comprising a fusion protein described herein. In some embodiments, the present disclosure provides a dimeric protein comprising a first fusion protein and a second fusion protein, wherein: each fusion protein comprises an immunoglobulin (IgG) Fc protein domain and at least one additional protein domain selected from the group consisting of a human IL-2 protein domain; and a protein domain that binds to Interleukin 1 receptor-like 1 (ST2); and the dimeric protein comprises at least one human IL-2 protein domain and at least one protein domain that binds to ST2.

In certain embodiments, the first fusion protein comprises a human IL-2 protein domain, a first immunoglobulin Fc protein domain, and a first peptide linker; and the second fusion protein comprises a protein domain that binds to ST2, a second immunoglobulin Fc protein domain, and a second peptide linker domain. In certain embodiments, each domain has an amino-terminus (N-terminus) and a carboxy terminus (C-terminus); the first fusion protein is configured so that the C-terminus of the human IL-2 protein domain is fused through a peptide bond to the N-terminus of the first peptide linker domain; and the N-terminus of the first IgG Fc protein domain is fused through a peptide bond to the C-terminus of the first peptide linker domain; and the second fusion protein is configured so that the C-terminus of the second IgG Fc protein domain is fused through a peptide bond to the N-terminus of the second peptide linker domain; and the N-terminus of the protein domain that binds to ST2 is fused through a peptide bond to the C-terminus of the second peptide linker domain. In certain embodiments, the protein domain that binds to ST2 is a human IL-33 protein domain.

In certain embodiments, the protein domain that binds to ST2 is an antibody specific for ST2, or an antigen-binding fragment thereof. In certain embodiments, at least one of the fusion proteins of the dimeric protein further comprises at least one peptide linker domain. In certain embodiments, the human IL-2 protein domain comprises human IL-2 with a substitution selected from the group consisting of: T3A, N88R, N88G, D20H, C125S, Q126L, and Q126F, relative to the amino acid sequence of SEQ ID NO: 2. In certain embodiments, the immunoglobulin Fc protein domain comprises an amino acid sequence selected from the group consisting of the human IgG1 Fc variant of SEQ ID NO: 4, SEQ ID NO: 5, SEQ ID NO: 7. SEQ ID NO: 8 or SEQ ID NO: 9. In certain embodiments, the human IL-33 protein domain comprises human IL-33 with a substitution selected from the group consisting of C208S, C227S, C232S and C259S, relative to the amino acid sequence of SEQ ID NO: 10. In certain embodiments, the peptide linker domain comprises the amino acid sequence of SEQ ID NO: 6.

In certain embodiments of the dimeric proteins described herein, the first fusion protein comprises the amino acid sequence of SEQ ID NO: 12 and the second fusion protein comprises the amino acid sequence of SEQ ID NO: 13; the first fusion protein comprises the amino acid sequence of SEQ ID NO: 14 and the second fusion protein comprises the amino acid sequence of SEQ ID NO: 15; the first fusion protein comprises the amino acid of SEQ ID NO: 16 and the second fusion protein comprise the amino acid sequence of SEQ ID NO: 15; the first fusion protein comprises the amino acid sequence of SEQ ID NO: 17 and the second fusion protein comprises the amino acid sequence of SEQ ID NO: 15; the first fusion protein comprises the amino acid sequence of SEQ ID NO: 18 and the second fusion protein comprises the amino acid sequence of SEQ ID NO: 12; the first fusion protein and the second fusion protein each comprise the amino acid sequence of SEQ ID NO: 19; the first fusion protein and the second fusion protein each comprise the amino acid sequence of SEQ ID NO: 20; the first fusion protein and the second fusion protein each comprise the amino acid sequence of SEQ ID NO: 22, and the dimeric protein further comprises the amino acid sequence of SEQ ID NO: 29; the first fusion protein and the second fusion protein each comprise the amino acid sequence of SEQ ID NO: 23, and the dimeric protein further comprise the amino acid sequence of SEQ ID NO: 30; the first fusion protein comprises the amino acid sequence of SEQ ID NO: 26, the second fusion protein comprises the amino acid sequence of SEQ ID NO: 24, and the dimeric protein further comprises the amino acid sequence of SEQ ID NO: 29; the first fusion protein comprises the amino acid sequence of SEQ ID NO: 27, the second fusion protein comprises the amino acid sequence of SEQ ID NO: 25, and the dimeric protein further comprises the amino acid sequence of SEQ ID NO: 30; the first fusion protein comprises the amino acid sequence of SEQ ID NO: 26, the second fusion protein comprises the amino acid sequence of SEQ ID NO: 16, and the dimeric protein further comprises the amino acid sequence of SEQ ID NO: 29; the first fusion protein comprises the amino acid sequence of SEQ ID NO: 27, the second fusion protein comprises the amino acid sequence of SEQ ID NO: 16, and the dimeric protein further comprises the amino acid sequence of SEQ ID NO: 30; the first fusion protein comprises the amino acid sequence of SEQ ID NO: 26, the second fusion protein comprises the amino acid sequence of SEQ ID NO: 14, and the dimeric protein further comprises the amino acid sequence of SEQ ID NO: 29; the first fusion protein comprises the amino acid sequence of SEQ ID NO: 27, the second fusion protein comprises the amino acid sequence of SEQ ID NO: 14, and the dimeric protein further comprises the amino acid sequence of SEQ ID NO: 30; the first fusion protein comprises the amino acid sequence of SEQ ID NO: 28, the second fusion protein comprises the amino acid sequence of SEQ ID NO: 24, and the dimeric protein further comprises the amino acid sequence of SEQ ID NO: 29; or the first fusion protein comprises the amino acid sequence of SEQ ID NO: 28, the second fusion protein comprises the amino acid sequence of SEQ ID NO: 25, and the dimeric protein further comprises the amino acid sequence of SEQ ID NO: 30.

In certain embodiments of the dimeric proteins described herein, the IgG Fc protein comprises cysteine residues, and the first fusion protein and the second fusion protein are linked to each other through the cysteine residues of the IgG Fc protein domain. In certain embodiments, the dimeric protein selectively targets $ST2^+$ regulatory T cells relative to $ST2^-$ regulatory T cells. In some embodiments, the present disclosure provides a pharmaceutical composition comprising a fusion protein described herein or a dimeric protein described herein.

In some embodiments, the present disclosure provides a method for treating a condition, the method comprising administering to a subject in need thereof a therapeutically-effective amount of the pharmaceutical composition of claim 28. In certain embodiments, the administering results in a greater increase in levels of $ST2^+$ regulatory T cell in the subject relative to levels of $ST2^-$ regulatory T cells in the subject. In certain embodiments, the administering selectively activates $ST2^+$ regulatory T cells in the subject relative to $ST2^-$ regulatory T cells in the subject. In certain embodiments, the therapeutically-effective amount is from about 1 µg/kg to about 250 µg/kg.

In certain embodiments, the condition is an inflammatory myopathy. In certain embodiments, the inflammatory myopathy is selected from the group consisting of muscular dystrophy, polymyositis, dermatomyositis. In certain embodiments, the condition is selected from the group consisting of an inflammatory condition of adipose tissue, an inflammatory condition of the colon, and an inflammatory condition of the lung. In certain embodiments, the adipose tissue is visceral adipose tissue. In certain embodiments, the condition is an autoimmune disease. In certain embodiments, the autoimmune disease is selected from the group consisting of Graft-vs-Host Disease, Pemphigus Vulgaris, Systemic Lupus Erythematosus, Scleroderma, Ulcerative Colitis, Crohn's Disease, Psoriasis, Type 1 Diabetes, Multiple Sclerosis, Amyotrophic Lateral Sclerosis, Alopecia Areata, Uveitis, Neuromyelitis Optica, and Duchenne Muscular Dystrophy. In certain embodiments, the administration is intravenous. In certain embodiments, the administration is subcutaneous. In certain embodiments, the subject is a human.

In some embodiments, the present disclosure provides a method of selectively activating an $ST2^+$ regulatory T cell relative to an $ST2^-$ regulatory T cell in a subject, the method comprising administering to the subject a therapeutically effective amount of the pharmaceutical composition of claim 28. In certain embodiments, the therapeutically-effective amount is from about 1 µg/kg to about 250 µg/kg. In certain embodiments, the administration is intravenous. In certain embodiments, the administration is subcutaneous. In certain embodiments, the subject is a human.

In some embodiments, the present disclosure provides a compound comprising: a) a first moiety that binds to an IL-2 receptor covalently linked to an immunoglobulin Fc domain; and b) a second moiety that binds to ST2 covalently linked to an immunoglobulin Fc domain.

In some embodiments, the present disclosure provides a compound comprising: a) a first moiety that binds to an IL-2 receptor; and b) a second moiety that binds to ST2; wherein the first moiety that binds to an IL-2 receptor comprises a mutation with respect to wild-type IL-2 that increases stability with respect to wild-type IL-2 of the moiety that binds the IL-2 receptor in the subject.

In some embodiments, the present disclosure provides a compound comprising: a) a first moiety that binds to an IL-2 receptor; and b) a second moiety that binds to ST2; wherein the first moiety that binds to an IL-2 receptor selectively binds to the IL2Rαβγ receptor relative to the IL2Rβγ receptor.

In some embodiments, the present disclosure provides a compound comprising: a) a first moiety that binds to an IL-2 receptor; and b) a second moiety that binds to ST2; wherein the first moiety that binds to an IL-2 receptor differs from wild-type IL-2 in a substitution that is N88R with respect to the wild-type IL-2.

In some embodiments of the compounds described herein, the first moiety comprises a polypeptide. In some embodiments, the first moiety that binds to the IL-2 receptor comprises a peptide sequence that has at least 90% identity to wild-type IL-2. In some embodiments, the mutation that increases stability with respect to wild-type IL-2 of the moiety that binds the IL-2 receptor in the subject is a substitution that is C125S with respect to the wild-type IL-2. In some embodiments, the first moiety that binds to the IL-2 receptor differs from wild-type IL-2 in a substitution that is T3A with respect to the wild-type IL-2. In some embodiments, the first moiety that binds to the IL-2 receptor has at least 90% identity to SEQ ID NO: 1. In some embodiments, the first moiety that binds to the IL-2 receptor comprises SEQ ID NO: 1. In some embodiments, the first moiety that binds to the IL-2 receptor is SEQ ID NO: 1.

In some embodiments, the second moiety that binds to ST2 comprises a polypeptide. In some embodiments, the second moiety that binds to ST2 comprises a peptide sequence that has at least 90% identity to wild-type IL-33. In some embodiments, the second moiety that binds to ST2 has at least 90% identity to SEQ ID NO: 10. In some embodiments, the second moiety that binds to ST2 is an antibody directed to ST2, or an antigen-binding fragment thereof. In some embodiments, the second moiety that binds to ST2 comprises SEQ ID NO: 10. In some embodiments, the second moiety that binds to ST2 is SEQ ID NO: 10. In some embodiments, the first moiety that binds to the IL-2 receptor and the second moiety that binds to ST2 are covalently linked. In some embodiments, the first moiety that binds to the IL-2 receptor and the second moiety that binds to ST2 are covalently linked by a disulfide bond.

In some embodiments of the compounds described herein, the compound further comprises two multimerization moieties. In some embodiments, a first multimerization moiety is covalently linked to the first moiety that binds to the IL-2 receptor and a second multimerization moiety is covalently linked to the second moiety that binds to ST2. In some embodiments, the two multimerization moieties are covalently linked to each other. In some embodiments, the two multimerization moieties are polypeptide sequences. In some embodiments, the two multimerization moieties are immunoglobulin Fc domains. In some embodiments, the immunoglobulin Fc domains are deficient in effector functions relative to corresponding wild-type immunoglobulin Fc domains. In some embodiments, the immunoglobulin Fc domains are IgG1 immunoglobulin Fc domains. In some embodiments, the IgG1 immunoglobulin Fc domains differ from wild-type IgG1 immunoglobulin Fc domains in a substitution that is N297A with respect to the wild-type IgG1 immunoglobulin Fc domains. In some embodiments, each immunoglobulin Fc domain comprises SEQ ID NO: 7. In some embodiments, each immunoglobulin Fc domain is SEQ ID NO: 7.

In some embodiments of the compounds described herein, the compound comprises a linker peptide covalently linked to the first moiety that binds to the IL-2 receptor and covalently linked to the first multimerization moiety. In some embodiments, the compound comprises a linker peptide covalently linked to the second moiety that binds to ST2 and covalently linked to the second multimerization moiety. In some embodiments, the compound comprises a first linker peptide covalently linked to the first moiety that binds to the IL-2 receptor and is covalently linked to the first multimerization moiety, and a second linker peptide covalently linked to the second moiety that binds to ST2 and is covalently linked to the second multimerization moiety. In some embodiments, the first moiety that binds to the IL-2 receptor is N-terminal to the first linker peptide, and the first multimerization moiety is C-terminal to the first linker peptide, and the second moiety that binds to ST2 is N-terminal to the second linker peptide, and the second multimerization moiety is C-terminal to the second linker peptide. In some embodiments, the first linker peptide and the second linker peptide are each from 6 to 20 amino acid residues. In some embodiments, the first linker peptide and the second linker peptide are each from 12 to 17 amino acid residues. In some embodiments, the first linker peptide and the second linker peptide are each sequences of amino acid residues that are each independently serine or glycine. In some embodiments, the first linker peptide and the second linker peptide are each 15 amino acid residues. In some embodiments, the first linker peptide and the second linker peptide are each GGGGSGGGGSGGGGS (SEQ ID NO: 6). In some embodiments, the compound selectively targets ST2+ regulatory T cells relative to ST2− regulatory T cells.

In certain aspects, the present disclosure relates to a method for treating a condition, the method comprising administering to a subject in need thereof a therapeutically-effective amount of a compound of any one of claims 1-40. In some embodiments, the administration increases an ST2+ regulatory T cell count in the subject relative to an ST2− regulatory T cell count in the subject. In some embodiments, the administration selectively activates ST2+ regulatory T cells in the subject relative to ST2− regulatory T cells in the subject. In some embodiments, the therapeutically-effective amount is from about 1 µg/kg to about 250 µg/kg. In some embodiments, the condition is an inflammatory myopathy. In some embodiments, the inflammatory myopathy is muscular dystrophy. In some embodiments, the inflammatory myopathy is polymyositis. In some embodiments, the inflammatory myopathy is dermatomyositis. In some embodiments, the condition is an inflammatory condition of adipose tissue. In some embodiments, the adipose tissue is visceral adipose tissue. In some embodiments, the condition is an inflammatory condition of the colon. In some embodiments, the condition is an inflammatory condition of the lung. In some embodiments, the administration is intravenous. In some embodiments, the administration is subcutaneous. In some embodiments, the subject is a human.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
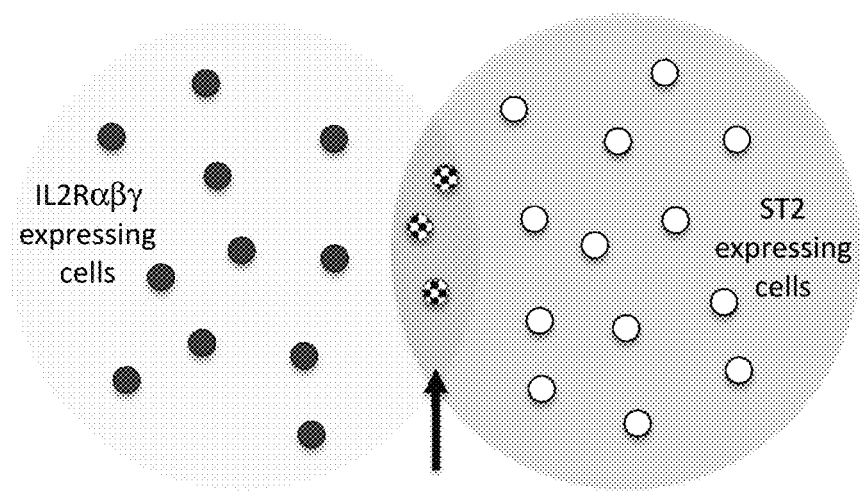
FIG. 1 shows a diagram illustrating the overlap of cells expressing IL-2Rαβγ and ST2.

Regulatory T cells (Tregs) are a class of CD4+CD25+ T cells that suppress the activity of other immune cells, such as CD4+ conventional T cells (Tconv) and CD8+ cells. Tregs are central to immune system homeostasis, maintain tolerance to self-antigens, and modulate the immune response to foreign antigens. Tregs can be robustly activated by Interleukin 2 (IL-2), but IL-2 also activates many other cell types, which can result in significant toxicity. It has become clear that there are subsets of Tregs that can be defined by expression of specific molecular markers and by their roles in different immunological responses. One Treg subset is the ST2+ Treg subset. The defining cell surface marker for ST2+ Tregs is ST2, a component of a cytokine receptor also known interleukin 1 receptor-like 1 protein (IL1RL1), and which is a subunit of the IL-33 receptor. IL-33 is categorized as an "alarmin", an inflammatory cytokine associated with acute inflammatory responses. ST2+ Tregs are found in tissues such as muscle, visceral adipose, colon, and lung, and possess immunoregulatory and tissue repair functions.

Skeletal muscle is normally devoid of T cells, but following acute muscle injury, large numbers of ST2+ Tregs rapidly migrate into muscle tissue in large numbers. The recruitment of these Tregs into muscle tissue, and production of the growth factor amphiregulin (AREG) has been associated with activation of muscle satellite cells and with tissue repair. Treg deficiency impairs muscle repair after injury, and expansion of Tregs in muscle using IL-2-IL-2R complexes leads to improved outcomes in an animal model of dystrophin-deficient muscular dystrophy. A significant fraction of Tregs that produce AREG are ST2+. ST2+ Tregs also have also been associated with inflamed lung tissue following influenza virus infection, and are associated with lung tissue repair following infection. Treatment of ST2+ Treg with the ligand for the ST2 receptor, IL-33, increases AREG production and tissue repair. Therefore, enhancing the number of ST2+ Tregs or the activity of ST2+ Tregs can treat, or prevent, autoimmune and inflammatory diseases such as inflammatory myopathies, inflammatory muscle diseases, and improve tissue healing after injury or stress.

For example, the role of ST2+ Tregs has been established in animal models of muscle inflammation. One of those animal models is acute muscle injury (Burzyn et al., 2013, Cell 155(6): 1282-1295) in wild type mice, and a second model is the mdx mouse muscular dystrophy model, a model of chronic muscle inflammation caused by genetic deficiency in dystrophin (mdx mice; Villalta et al., 2014, Sci Transl Med 5(258): 258ra142). A role for ST2+ Treg has also been established in a mouse model of inflammatory bowel disease (Schiering et al., 2014, Nature 513(7519):564-568).

By providing compounds and methods that are able to selectively expand ST2+ Tregs numbers and/or enhance ST2+ Treg activity, the present disclosure makes possible new treatments of inflammatory and degenerative diseases. For example, the present disclosure provides a compound with a first moiety that binds to the IL-2 receptor (IL-2R or IL2R) and a second moiety that binds to ST2. IL-2R is a heterotrimeric protein expressed on a variety of different immune cell types, including T cells, NK cells, eosinophils, and monocytes. This broad expression pattern provides a pleiotropic effect on the immune system and a high systemic toxicity of IL-2 treatments, and can make targeting IL-2R+ cells challenging.

IL2-R has three forms, generated by different combinations of three different IL-2R proteins: α (alpha), β (beta), and γ (gamma). These receptor chains assemble to generate the three different receptor forms: (1) the low affinity receptor, IL2Rα, which does not signal; (2) the intermediate affinity receptor (IL2Rβγ), composed of IL2Rβ and IL2Rγ, which is broadly expressed on CD4+ conventional T cells (Tconv), NK cells, eosinophils, and monocytes; and (3) the high affinity receptor (IL2Rαβγ), composed of IL2Rα, IL2Rβ, and IL2Rγ, which is expressed transiently on activated T cells and constitutively on Treg cells. Conventional T cells (Tconv) are those which are activated by antigens and participate in the immune attack. Conventional T cells include helper T cells, cytotoxic T cells, and memory T cells. Mutations in IL-2 can change the binding affinity of IL-2 to different IL-2R receptor forms. Thus, the present disclosure provides compounds that selectively activate and expand Tregs, for example ST2+ Tregs, by comprising a moiety that selectively binds to the high affinity receptor (IL2Rαβγ). An exemplary moiety includes, but is not limited to, an IL-2 variant comprising one or more mutations that modifies the binding relative to wild-type IL-2 so that the IL-2 variant selectively binds to the high affinity receptor (IL2Rαβγ) relative to the intermediate affinity receptor and the low affinity receptor.

Figure 2:
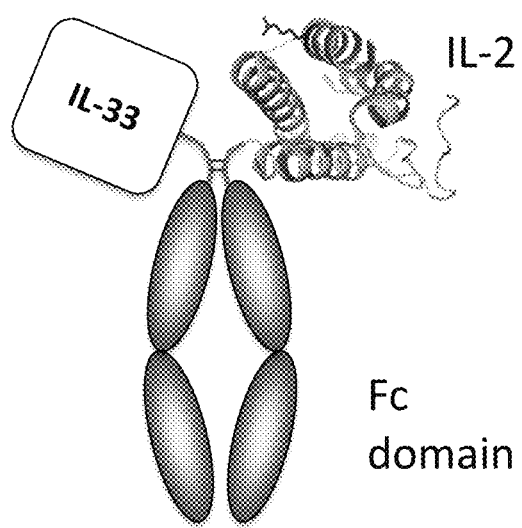
FIG. 2 shows a schematic depiction of an exemplary compound of this disclosure.
Figure 3A:
FIG. 3A shows a schematic diagram of a compound having an IL2R-binding moiety, an ST2-binding moiety, and a linker between them.
Figure 3B:
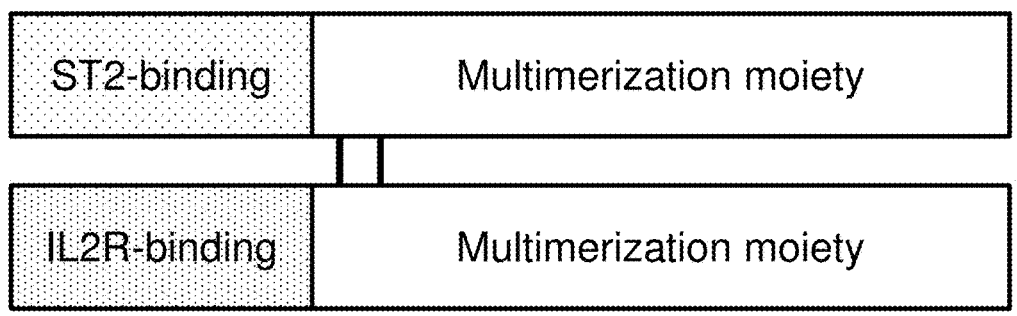
FIG. 3B shows a schematic diagram of an exemplary compound having an IL2R-binding moiety covalently linked to a multimerization moiety, an ST2-binding moiety covalently linked to a multimerization moiety, and covalent bonds between the multimerization moieties.
Figure 3C:
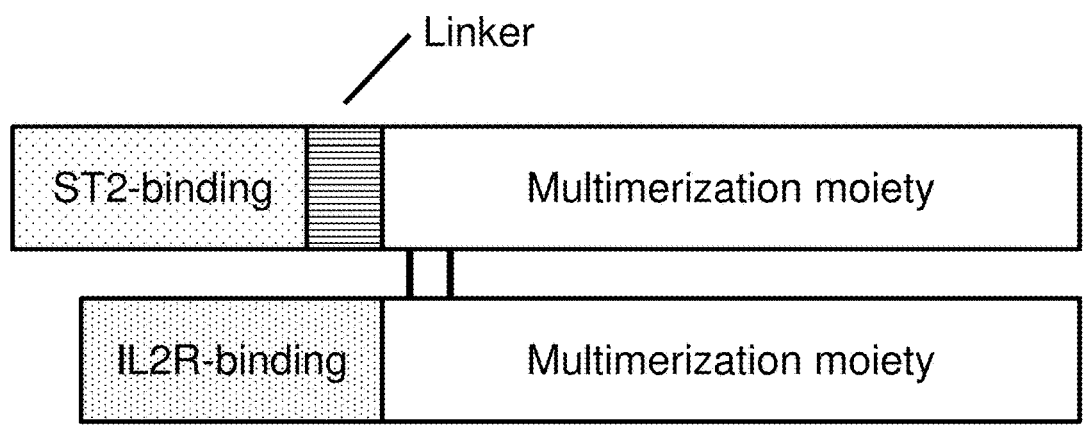
FIG. 3C shows a schematic diagram of an exemplary compound having an IL2R-binding moiety covalently linked to a multimerization moiety, an ST2-binding moiety covalently linked to a linker covalently linked to a multimerization moiety, and covalent bonds between the multimerization moieties.
Figure 3D:
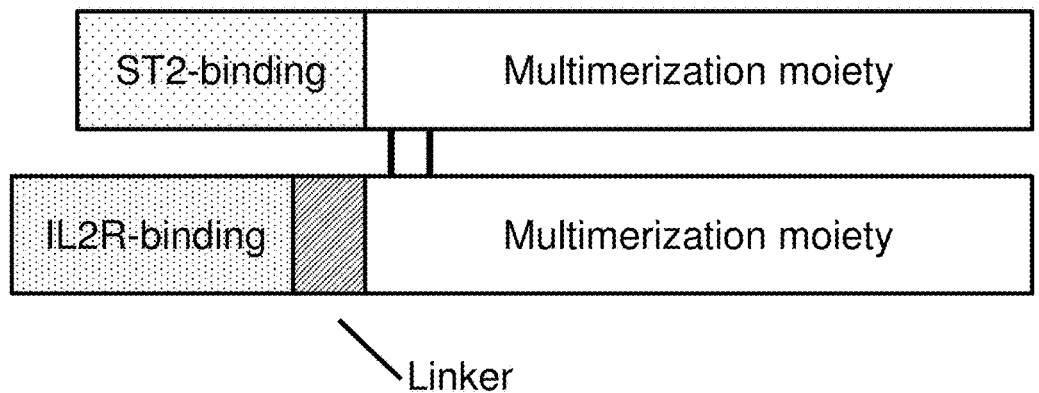
FIG. 3D shows a schematic diagram of an exemplary compound having an IL2R-binding moiety covalently linked to a linker covalently linked to a multimerization moiety, an ST2-binding moiety covalently linked to a multimerization moiety, and covalent bonds between the multimerization moieties.
Figure 3E:
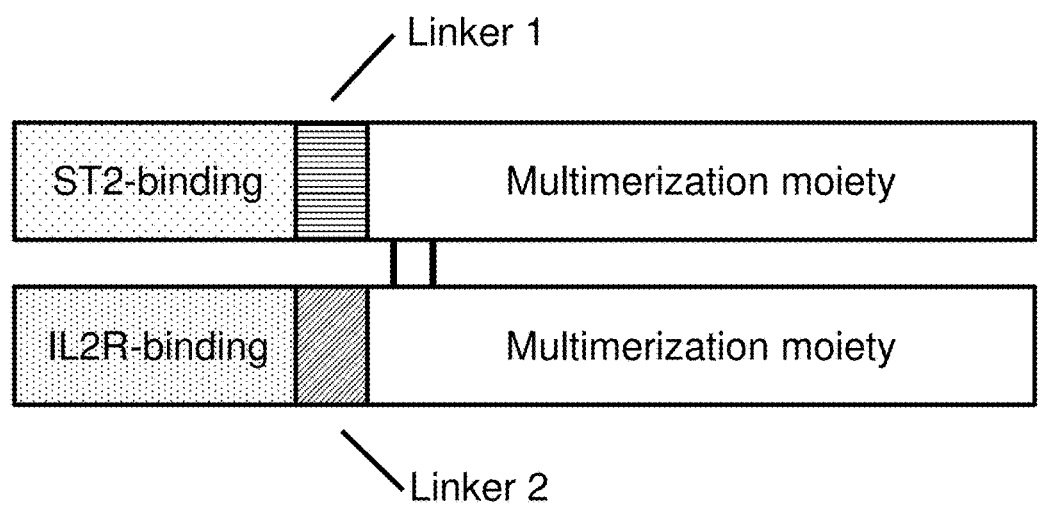
FIG. 3E shows a schematic diagram of an exemplary compound having an IL2R-binding moiety covalently linked to a linker covalently linked to a multimerization moiety, an ST2-binding moiety covalently linked to a linker covalently linked to a multimerization moiety, and covalent bonds between the multimerization moieties.
Figure 3F:
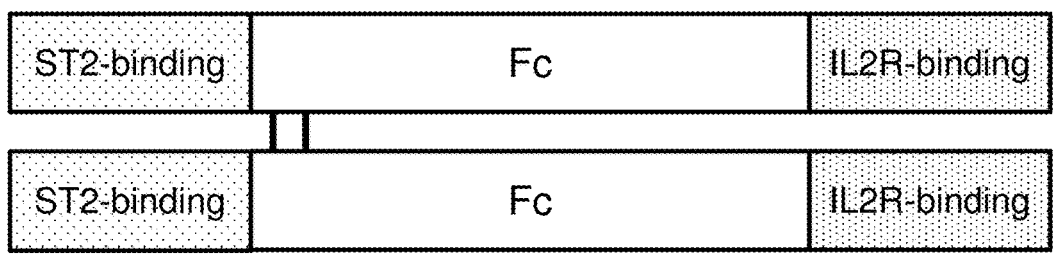
FIG. 3F shows a schematic diagram of an exemplary compound having a) an IL2R-binding moiety covalently linked to a multimerization moiety covalently linked to an ST2-binding moiety, b) an ST2-binding moiety covalently linked to a multimerization moiety covalently linked to an IL2R-binding moiety, and c) covalent bonds between the multimerization moieties.

Methods and compositions of the present disclosure relate to a compound comprising a first moiety that binds to the IL-2 receptor and a second moiety that binds to ST2, enabling the compound to be much more selective and potent in its ability to activate and expand ST2+ Tregs. In some embodiments, these compounds target cells that express both the IL-2 receptor or a specific isoform thereof, and ST2. For example, a compound that specifically binds to the IL2Rαβγ isoform can bind to Treg cells expressing ST2. FIG. 1 shows expression domains of IL-2Rαβγ and ST2 in a mixed population of Tregs and an example of an area of overlap where a compound of this disclosure can bind. In some embodiments, the first and second moieties are covalently linked, for example, by an immunoglobulin Fc domain. In some embodiments, the compound also comprises a linker joining the IL-2 receptor-binding moiety and the immunoglobulin Fc domain and/or a linker joining the ST2-binding moiety and the immunoglobulin Fc domain. In some embodiments, the compound can regulate the activities of white blood cells, for example, leukocytes or lymphocytes, that are responsible for immunity. The immunoglobulin Fc domain can increase the in vivo stability of the molecule, and the linker covalently joins a moiety and an Fc domain. By providing moieties that bind to the IL2 receptor and to ST2, the compounds described herein can target cells (for example, T regulatory cells) that express both the IL2 receptor and ST2. In some embodiments, an Fc domain is deficient in its effector functions. An exemplary compound comprises a first moiety that binds to the IL-2 receptor and a second moiety that binds to ST2, wherein the first moiety that binds to the IL-2 receptor is covalently linked to a first effector-deficient Fc domain via a linker and the second moiety that binds to ST2 is covalently linked to a second effector-deficient Fc domain via a linker, and wherein the first effector-deficient Fc domain and the second effector-deficient Fc domain are covalently linked via a disulfide bond. An example of such a compound is shown in FIG. 2. Further exemplary compounds are shown in FIGS. 3A-3E, which depict compounds comprising ST2-binding and IL2R-binding moieties, in various combinations with linkers and multimerization domains (which can be, for example, Fc domains). Another example of such a compound is shown in FIG. 3F, wherein an IL2 moiety and an ST2-binding moiety are at the N-terminus and the C-terminus, respectively, of an IgG Fc protein. Such a protein may be in reversed orientation, wherein the ST2-binding moiety is at the N-terminus and the IL2 moiety is at the C-terminus, and may incorporate peptide linkers between one or both of the ST-2 binding moieties and their respective Fc domains, or between one or both of the IL2R binding moieties and their respective Fc domains. An exemplary method for treating a condition, for example, an inflammatory condition such as an inflammatory myopathy, comprises administering to a subject in need thereof a therapeutically-effective amount of a compound as described herein. Exemplary conditions include, but are not limited to, muscular dystrophy and dermatomyositis.

Moieties that Bind the IL-2 Receptor

As described above, the present disclosure provides a compound comprising a first moiety that binds an IL-2 receptor and a second moiety that binds ST2. A moiety that binds an IL-2 receptor can be a polypeptide comprising the full length of wild-type IL-2, shorter, or longer. The IL-2 receptor-binding moiety can have a wild-type IL-2 sequence, as shown in SEQ ID NO: 2: (APTSSSTKK-TQLQLEHLLLDLQMILNGINNYKNPKLTRMLTFKFY-MPKKATELKHLQCLEE ELKPLEEVLNLAQSKNFHL-RPRDLISNINVIVLELKGSETTFMCEYADETATIVEFL-NRWITFX QSIISTLT) or a variant of IL-2. IL-2 variants can contain one or more substitutions, deletions, or insertions that deviate from the wild-type IL-2 amino acid sequence. Residues are designated herein by the one letter amino acid code followed by the IL-2 amino acid position, e.g., K35 is the lysine residue at position 35 of the wild-type IL-2 sequence. Substitutions are designated herein by the one letter amino acid code followed by the IL-2 amino acid position followed by the substituting one letter amino acid code, e.g., K35A is a substitution of the lysine residue at position 35 of SEQ ID NO: 2 with an alanine residue.

Compounds herein can exhibit specificity for different IL-2 receptor classes that is similar or dissimilar to the specificity of wild-type IL-2. Compounds herein can exhibit increased stability or biological effect in comparison to wild-type IL-2. For example, a mutation can provide a compound with increased specificity for certain IL-2 receptors in comparison to wild-type IL-2. In some embodiments, a compound selectively binds to the IL2Rαβγ receptor relative to the IL2Rβγ receptor, for example, through its IL-2 binding moiety. In some embodiments, this selective binding is due to one or more mutations in an IL-2 sequence as compared to a wild-type IL-2 sequence. For example, IL-2 N88R is selective for binding to the IL2Rαβγ receptor over the IL2Rβγ receptor. IL-2 can stimulate the proliferation of IL2Rαβγ-expressing PHA-activated T cells as effectively as wildtype IL-2, while exhibiting a 3,000-fold reduced stimulation of the proliferation of IL2Rβγ-expressing NK cells. Other mutations that exhibit increased selectivity for IL2Rαβγ include the substitutions D20H, N88I, N88G, Q126L, and Q126F.

In some embodiments, an IL-2 receptor-binding moiety comprises a mutation that enhances the stability of a compound of the present disclosure. For example, an IL-2 C125S mutation promotes stability by eliminating an unpaired cysteine residue, thereby preventing misfolding of the IL-2 polypeptide. Misfolding can lead to protein aggregation and increase clearance of the polypeptide in vivo. In some embodiments, an IL-2 polypeptide comprises a mutation that creates or removes a glycosylation site. For example the IL-2 mutation T3A removes an O-linked glycosylation site. In some embodiments, an IL-2 variant with the T3A mutation also comprises an N88R mutation and/or a C125S mutation. In some embodiments, an IL-2 variant comprises T3A, N88R, and C125S mutations, as in SEQ ID NO: 3.

In some embodiments, substitutions occur at one or more of positions 3, 20, 88, 125, and 126. In some embodiments, substitutions occur at one, two, three, four, or five of the positions. In some embodiments, an IL-2 variant comprises mutations at positions 88 and 125, for example, N88R and C125S. In some embodiments, an IL-2 receptor-binding moiety comprises the amino acid sequence set forth in SEQ ID NO: 1: APTSSSTKKTQLQLEHLLLDLQMILNGINN-YKNPKLTRMLTFKFYMPKKATELKHLQCLEEELKP-LEEVLNLAQSKNFHLRPRDLISRINVIVLELKGSETTF-MCEYADETATIVEFLNRWITFSQ SIISTLT. In some embodiments, an IL-2 variant comprises mutations at positions 3, 88 and 125, for example, T3A, N88R and C125S, as in SEQ ID NO: 3: APASSSTKKTQLQLEHLLLDLQMILNG-INNYKNPKLTRMLTFKFYMPKKATELKHLQCLEE EL-KPLEEVLNLAQSKNFHLRPRDLISRINVIVLELKGSE-TTFMCEYADETATIVEFLNRWITFS QSIISTLT. In some embodiments, an IL-2 variant comprises 1, 2, 3, 4, 5, 6, 7, 8, 9, 10, 11, 12, 13, 14, 15, 16, 17, 18, 19, or 20 mutations (e.g., substitutions) in comparison to a wild-type IL-2 sequence.

Compounds herein include IL-2 variants comprising an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the wild-type IL-2 amino acid sequence (SEQ ID NO: 2). Compounds herein include IL-2 variants comprising an amino acid sequence that is 60%-99% identical to the wild-type IL-2 amino acid sequence, for example, an amino acid sequence that is 80%-99% identical to the wild-type IL-2 amino acid sequence, an amino acid sequence that is 85%-99% identical to the wild-type IL-2 amino acid sequence, an amino acid sequence that is 90%-99% identical to the wild-type IL-2 amino acid sequence, or an amino acid sequence that is 95%-99% identical to the wild-type IL-2 amino acid sequence (SEQ ID NO: 2). Compounds herein include IL-2 variants that comprise an amino acid sequence having an N88R mutation that is at least 60%, at least 610%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the wild-type IL-2 amino acid sequence (SEQ ID NO: 2). Compounds herein include IL-2 variants comprising an amino acid sequence having an N88R mutation that is 60%-99% identical to the wild-type IL-2 amino acid sequence, for example, an amino acid sequence that is 80%-99% identical to the wild-type IL-2 amino acid sequence (SEQ ID NO: 2), an amino acid sequence that is 85%-99% identical to the wild-type IL-2 amino acid sequence (SEQ ID NO: 2), an amino acid sequence that is 90%-99% identical to the wild-type IL-2 amino acid sequence (SEQ ID NO: 2), or an amino acid sequence that is 95%-99% identical to the wild-type IL-2 amino acid sequence (SEQ ID NO: 2).

Embodiments also include IL-2 variants that selectively stimulate Treg cells and comprise an amino acid sequence having N88R and C125S mutations that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the wild-type IL-2 amino acid sequence (SEQ ID NO: 2). Compounds herein include IL-2 variants comprising an amino acid sequence having N88R and C125S mutations that is 60%-99% identical to the wild-type IL-2 amino acid sequence (SEQ ID NO: 2), for example, an amino acid sequence that is 80%-99% identical to the wild-type IL-2 amino acid sequence (SEQ ID NO: 2), an amino acid sequence that is 85%-99% identical to the wild-type IL-2 amino acid sequence (SEQ ID NO: 2), an amino acid sequence that is 90%-99% identical to the wild-type IL-2 amino acid sequence (SEQ ID NO: 2), or an amino acid sequence that is 95%-99% identical to the wild-type IL-2 amino acid sequence (SEQ ID NO: 2).

Compounds also include IL-2 variants that selectively stimulate Treg cells and comprise an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the wild-type IL-2 amino acid sequence (SEQ ID NO: 2). Compounds also include IL-2 variants that selectively stimulate Treg cells and comprise an amino acid sequence that is 60%-99% identical to the wild-type IL-2 amino acid sequence (SEQ ID NO: 2), for example, an amino acid sequence that is 80%-99% identical to the wild-type IL-2 amino acid sequence (SEQ ID NO: 2), an amino acid sequence that is 85%-99% identical to the wild-type IL-2 amino acid sequence (SEQ ID NO: 2), an amino acid sequence that is 90%-99% identical to the wild-type IL-2 amino acid sequence (SEQ ID NO: 2), or an amino acid sequence that is 95%-99% identical to the wild-type IL-2 amino acid sequence (SEQ ID NO: 2).

Various methods and software programs can be used to determine the homology between two or more peptides or nucleic acids, such as NCBI BLAST, Clustal W, MAFFT, Clustal Omega, AlignMe, Praline, or another suitable method or algorithm. In some embodiments, percent identity is calculated by FastDB based upon the following parameters: mismatch penalty of 1; gap penalty of 1; gap size penalty of 0.33; and joining penalty of 30.

An example of a useful algorithm is PILEUP. PILEUP creates a multiple sequence alignment from a group of related sequences using progressive, pairwise alignments. The algorithm can also plot a tree showing the clustering relationships used to create the alignment. A non-limiting example of PILEUP parameters includes a default gap weight of 3.00, a default gap length weight of 0.10, and weighted end gaps.

Another example of a useful algorithm is the BLAST algorithm. A non-limiting example of a BLAST program is the WU-BLAST-2 program. WU-BLAST-2 uses several search parameters, most of which are set, for example, to the default values. The adjustable parameters are set, for example, with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. The values can be adjusted to increase sensitivity.

An additional useful algorithm is gapped BLAST. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to, for example, about 22 bits.

An additional useful tool is Clustal, a series of commonly used computer programs for multiple sequence alignment. Recent versions of Clustal include ClustalW, ClustalX and Clustal Omega. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Mutations can be installed at chosen sites or at random. For example, random mutagenesis at a target codon or region can provide mutants to be screened for an activity. Techniques for making substitution mutations at predetermined sites in DNA having a known sequence include, for example, M13 primer mutagenesis and PCR mutagenesis. Screening of the mutants can be accomplished, for example, using assays described herein.

Amino acid substitutions can be of single or multiple residues. Insertions can be, for example, from about 1 to about 20 amino acid residues, or more. Deletions can be, for example, from about 1 to about 20 amino acid residues, or more. Substitutions, deletions, insertions, or any combination thereof can occur in the sample compound.

Moieties that Bind ST2

ST2 (Interleukin 1 receptor-like 1) is a membrane-bound cytokine receptor and a member of the IL-1 receptor family. Human ST2 consists of a 310 amino acid (aa) extracellular domain (ECD) with three Ig-like domains, a 21 aa transmembrane segment, and a 207 aa cytoplasmic domain with an intracellular TIR domain (Tominaga, S. et al., 1992, Biochim. Biophys. Acta 1171:215; and Li, H. et al., 2000, Genomics 67:284.). ST2 binds IL-33 and heterodimerizes with the IL-1 receptor accessory protein (1RAcP). In some embodiments, a compound of the present disclosure comprises a binding moiety that binds ST2. A moiety that binds ST2 can be a polypeptide comprising the full length of wild-type IL-33, shorter, or longer. The ST2-binding moiety can have a wild-type IL-33 sequence, as shown in SEQ ID NO: 10 (SITGISPITEYLASLSTYNDQSITFALEDESYEI-YVEDLKKDEKKDKVLLSYYESQHPSNESGD GVDG-KMLMVTLSPTKDFWLHANNKEHSVELHKCEKPLP-DQAFFVLHNMHSNCVSFECKT DPGVFIGVKDNHLALIKVDSSENLCTENILFKLSET) or it can be a variant of IL-33. IL-33 variants can contain one or more substitutions, deletions, or insertions that deviate from the wild-type IL-33 amino acid sequence. Residues are designated herein by the one letter amino acid code followed by the IL-33 amino acid position. Substitutions are designated herein by the one letter amino acid code followed by the IL-33 amino acid position followed by the substituting one letter amino acid code. In some embodiments, an IL-33 sequence is a human IL-33 sequence, for example, of residues 112-170 of the wild-type sequence.

Compounds herein can have increased or decreased affinity for ST2 or for the ST2-1RAcP receptor complex. Some compounds may have enhanced affinity for ST2. Other compounds may have reduced affinity for 1RAcP, which would lead to reduced ability to activate the IL-33 receptor. Compounds herein can exhibit increased stability or biological effect in comparison to wild-type IL-33.

IL-33 variants can be generated with altered affinity for the IL-33 receptor subunits ST2 or IL1RAcP. In some embodiments, an IL-33 amino acid sequence can be mutated at one or more of the following positions relative to the wild-type IL-33 sequence: E119, Y122, D131, E144, Y146, D149, Y163, H246, N222 and N226. In some embodiments, amino acid substitutions at one or more of those can modulate the affinity of IL-33 for ST2. In some embodiments, an IL-33 amino acid sequence can be mutated to alter contacts with IL1RAcP: H168, N171, E200, H201, H224, D244, K 251 and E261 (all with respect to the wild-type IL-33 sequence). In some embodiments, amino acid substitutions at one or more of those can modulate the affinity of IL-33 for IL1RAcP, and thus modulate the ability to activate the receptor.

In some embodiments, an ST2-binding moiety comprises a variant of IL-33 comprising, for example, an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the wild-type IL-33 amino acid sequence (SEQ ID NO: 10). Compounds herein include IL-33 variants comprising an amino acid sequence that is 60%-99% identical to the wild-type IL-33 amino acid sequence (SEQ ID NO: 10), for example, an amino acid sequence that is 80%-99% identical to the wild-type IL-33 amino acid sequence (SEQ ID NO: 10), an amino acid sequence that is 85%-99% identical to the wild-type IL-33 amino acid sequence (SEQ ID NO: 10), an amino acid sequence that is 90%-99% identical to the wild-type IL-33 amino acid sequence (SEQ ID NO: 10), or an amino acid sequence that is 95%-99% identical to the wild-type IL-33 amino acid sequence (SEQ ID NO: 10). In some embodiments, an ST2-binding moiety is 100% identical to the wild-type IL-33 amino acid sequence (SEQ ID NO: 10).

ST2-binding ligands may include antibodies and antigen-binding antibody fragments with binding affinity toward ST2. As used herein, an "antibody" is a protein that includes at least one complementary determining region that binds to a specific target antigen, e.g. ST2. An antibody frequently includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The light chains of the immunoglobulin can be of types kappa or lambda. For example, an antibody can be a monoclonal antibody, a modified antibody, a chimeric antibody, a reshaped antibody, or a humanized antibody. The term "monoclonal antibody", as used herein, refers to a population of antibody molecules that contain only one species of an antigen binding site capable of immunoreacting with a particular epitope. Antibodies can be obtained from commercial sources or produced using known methods. The antibody can be any immunoglobulin type, e.g., IgG, IgM, IgY, IgA1, IgA2, IgD, or IgE. In an embodiment, the antibody can be a human antibody.

Antigen-binding antibody fragments suitable for use in the invention include, but are not limited to, a Fab fragment, a F(ab')2 fragment, a Fd fragment, a Fv fragment, a dAb fragment, single chain Fv, a dimerized variable region (V region) fragment (diabody), a disulfide-stabilized V region fragment (dsFv), affibodies, antibody mimetics, and one or more isolated complementarity determining regions (CDR) that retain specific binding to the payload, e.g. ST2. As used herein, an "isolated" CDR is a CDR not in the context of a naturally occurring antibody.

Polyclonal antibodies can be prepared by immunizing a suitable subject with a protein of the invention as an immunogen. The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest (i.e. ST2), e.g., using a standard ELISA assay.

Alternative to preparing monoclonal antibody-secreting hybridomas, a monoclonal antibody directed against ST2 can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Recombinant antibodies that specifically bind ST2 can also be prepared. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptide. They can be produced by techniques known in the art, for example using methods described in Ladner et. al U.S. Pat. No. 4,946,778 (which is incorporated herein by reference in its entirety); Bird et al., (1988) *Science* 242:423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad Sci. USA* 84:3439-3443; Liu et al. (1987) *J. Immunol.* 139:3521-3526; Sun et al. (1987) *Proc. Natl. Acad Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., ST2. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; 5,633,425; 5,569,825; 5,661,016; and 5,545,806. In addition, companies can be engaged to provide human antibodies directed against a selected antigen (e.g. ST2) using technology similar to that described above.

Completely human antibodies which recognize ST2 can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

The ST2 antibodies can be isolated after production (e.g., from the blood or serum of the subject) or synthesis and further purified by well-known techniques. For example, IgG antibodies can be purified using protein A chromatography. Antibodies specific for ST2 can be selected or (e.g., partially purified) or purified by, e.g., affinity chromatography. For example, a recombinantly expressed and purified (or partially purified) ST2 protein is produced, and covalently or non-covalently coupled to a solid support such as, for example, a chromatography column. The column can then be used to affinity purify antibodies specific for ST2 from a sample containing antibodies directed against a large number of different epitopes, thereby generating a substantially purified antibody composition, i.e., one that is substantially free of contaminating antibodies.

Antibodies that bind ST2 are well known in the art. For example, US2017/0002079 describes a range of ST2-binding antibodies (e.g. Ab1, Ab2, Ab3, Ab4 and Ab12-Ab36) directed against human ST2 that were prepared using XENOMOUSE® technology (U.S. Pat. Nos. 6,114,598; 6,162,963; 6,833,268; 7,049,426; 7,064,244, which are incorporated herein by reference in their entirety; Green et al., 1994, Nature Genetics 7:13-21; Mendez et al., 1997, Nature Genetics 15:146-156; Green and Jakobovitis, 1998, J. Ex. Med. 188:483-495, Kellermann and Green, 2002, Current Opinion in Biotechnology, 13:593-597). See, in particular, Example 2 of US2017/0002079, which is incorporated by reference herein in its entirety. Anti-ST2 antibodies directed against human ST2 are also described in WO2012/113813 (e.g. monoclonal antibody ra170) and U.S. Pat. No. 7,087,396 (e.g. monoclonal antibodies 2A5, FB9 and HB12), each of which is incorporated by reference herein in its entirety. For example, U.S. Pat. No. 7,087,396 describes preparation of monoclonal antibodies directed to human ST2 in Example 1. ST2-binding antibodies are also commercially available (e.g. R&D Systems, Inc., Minneapolis, Minn., Cat. Nos. MAB523 and AF523). MAB523 is a monoclonal mouse IgG1 antibody that detects human ST2. AF523 is an antigen affinity-purified polyclonal goat IgG1 that detects human ST2.

Linkage Between an IL-2R-Binding Moiety and an ST2-Binding Moiety

The IL-2R and ST2 binding moieties are linked. A first moiety that binds to the IL-2 receptor and a second moiety that binds to ST2 are linked covalently or non-covalently. In some embodiments, the first moiety that binds to the IL-2 receptor and the second moiety that binds to ST2 are covalently linked. For example, the first moiety that binds to the IL-2 receptor and the second moiety that binds to ST2 can be covalently linked by a sulfide bond or a disulfide bond. In some embodiments, a compound comprising a first moiety that binds to the IL-2 receptor and a second moiety that binds to ST2 comprises a multimerization moiety or two multimerization moieties, for example, Fc domains. For example, a first multimerization moiety can be covalently linked to the first moiety that binds to the IL-2 receptor and a second multimerization moiety can be covalently linked to the second moiety that binds to ST2. The two multimerization moieties also can be covalently linked to each other. In some embodiments, the two multimerization moieties are polypeptide sequences. For example, in some embodiments, a disulfide bond covalently links a first Fc domain that is covalently linked to the IL-2R-binding moiety and a second Fc domain that is covalently linked to the ST2-binding moiety.

Immunoglobulin Fc Domains

In some embodiments, a multimerization moiety is an immunoglobulin Fc domain, for example, an immunoglobulin Fc domain that is deficient in effector functions relative to a corresponding wild-type immunoglobulin Fc domain. Non-limiting examples of immunoglobulin Fc domains are IgG, IgA, IgD, IgM, and IgE immunoglobulin Fc domains. In some embodiments, an immunoglobulin Fc domains is an IgG1 immunoglobulin Fc domain.

Immunoglobulin Fc domains have a number of therapeutic benefits when incorporated into fusion proteins. For example, immunoglobulin Fc domains can increase the circulating half-life of the fusion partner protein.

In some embodiments, the increased circulating half-life is due to the Fc domain preventing aggregation of the fusion protein, thereby increasing its stability and slowing clearance.

The four human IgG subclasses differ in effector functions (CDC, ADCC), circulating half-life, and stability. IgG1 possesses Fc effector functions, and is the most abundant IgG subclass. IgG2 is deficient in Fc effector functions, but is subject to both dimerization with other IgG2 molecules, and instability due to scrambling of disulfide bonds in the hinge region. IgG3 possesses Fc effector functions, and has a long, rigid hinge region. IgG4 is deficient in Fc effector functions, and has a shorter circulating half-life than the other subclasses. The IgG4 dimer is biochemically unstable due to having only a single disulfide bond in the hinge region leading to the exchange of H chains between different IgG4 molecules. Fc sequence modifications can be made to the hinge region of an IgG2 Fc to prevent aggregation, or to the hinge region of an IgG4 Fc to stabilize dimers.

Effector function-deficient variants of IgG1 can be generated. For example, an amino acid substitution can be made at position N297, the location of an N-linked glycosylation site. In some embodiments, the substitution is N297A. Substitution of this asparagine residue removes the glycosylation site and significantly reduces antibody-dependent cell-mediated cytotoxicity (ADCC) and complement-dependent cytotoxicity (CDC) activity, thereby preventing unwanted cell lysis.

Various other effector function-deficient IgG1 variants can also be appreciated by the skilled worker. One non-limiting example of such a variant is IgG1(L234F/L235E/P331S), which mutates amino acids in the Clq and FcγR binding sites. These (or similar) Fc variants can be used to generate effector-deficient and stable IL-2 selective agonist-Fc fusion proteins (IL2SA-Fc). Forms of Fc protein moieties also can be engineered to create stable monomers rather than dimers. These modified Fc protein moieties also can be combined with an IL-2 compound of the present disclosure. Additionally, a functionally monomeric heterodimer comprising an IL-2-Fc H chain polypeptide can be combined with an Fc H chain polypeptide and assembled using bispecific antibody technology with an IL-2 selective agonist. IL-2 Fc fusion proteins also can be made with intact IgG antibody molecules, either with or without antigen specificity in the IgG moiety. Moreover, Fc variants that lack some of the hinge region can be used with the compounds and methods described herein.

In some embodiments, the sequence of an immunoglobulin Fc moiety is an IgG1 Fc moiety comprising an N297A mutation, for example, the sequence shown below:

DIKTHTCPPCPAPELLGGPSVFLFPPKPKDTLMISRTPEVTCVVVDVSHE

DPEVKFNWYVDGVEVHNAKTKPREEQYASTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHHEALHNHYTQKSLSLSPG (SEQ ID NO: 7; N297A mutation is shown in bold and underlined).

In some embodiments, the IgG1 Fc moiety has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 7.

The compound of the present disclosure can be produced under conditions that allow two Ig polypeptides to form an Fc domain. The two Ig polypeptides can be conjugated with different moieties. In some cases one IgG polypeptide is conjugated to an IL-2 moiety and the second Ig polypeptide is bound to a moiety that binds a cell surface protein other than the IL2 receptor. In some embodiments the cell surface protein bound by the binding moiety is ST2.

Linker

The linkage at the junction between an Fc domain and an IL2 receptor-binding moiety or an ST2-binding moiety can be: (1) a direct fusion of the two protein sequences; (2) a fusion with an intervening linker peptide; or (3) a fusion by a non-peptide moiety. In some embodiments, a linker directly links an IL2R-binding moiety and an ST2-binding moiety. Linker peptides can be included as spacers between two protein moieties. Linker peptides can promote proper protein folding, stability, expression, and bioactivity of the component protein moieties. Long flexible linker peptides can be composed of glycine, serine, or threonine, with multiple glycine residues providing a highly flexible conformation. Serine or threonine residues provide polar surface area to limit hydrophobic interaction within the peptide or with the component fusion protein moieties. In some embodiments, peptide linkers are rich in glycine and serine, such as repeats of the sequence GGGGS (SEQ ID NO: 31). In some embodiments, a peptide linker has a sequence of (GGGGS)$_n$ (SEQ ID NO: 31), wherein n is 1, 2, 3, 4, 5, 6, 7, 8, 9, or 10. In some embodiments, n is 3; i.e., a peptide linker has a sequence of GGGGSGGGGSGGGGS (SEQ ID NO: 6). In some embodiments, the IL-2 receptor-binding moiety is N-terminal to the linker peptide, and the immunoglobulin Fc domain is C-terminal to the linker peptide. In some embodiments, the IL-2 receptor-binding moiety is C-terminal to the linker peptide, and the immunoglobulin Fc domain is N-terminal to the linker peptide.

In some embodiments, the peptide linker has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 6.

Pharmaceutical Compositions

A pharmaceutical composition of the invention can comprise any compound described herein. In some embodiments, a pharmaceutical composition comprises a compound of the present disclosure with other chemical components, such as carriers, stabilizers, diluents, dispersing agents, suspending agents, thickening agents, and/or excipients. The pharmaceutical composition facilitates administration of a compound of the present disclosure to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining a compound of the present disclosure with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of cosolvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a compound of the present disclosure in water-soluble form. Suspensions of a compound of the present disclosure can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

A compound of the present disclosure can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

A compound of the present disclosure can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of a compound of the present disclosure into preparations that can be used pharmaceutically. Formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman. L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of dosage forms suitable for use in the disclosure include liquid, elixir, nanosuspension, aqueous or oily suspensions, drops, syrups, and any combination thereof: Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Diseases

The compounds of the present disclosure can be applied to various autoimmune or immune-related diseases or conditions, for example to treat such diseases or conditions. For example, the present disclosure provides a method for treating a condition, the method comprising administering to a subject in need thereof a therapeutically-effective amount of a compound of the present disclosure. In some embodiments, the compound administered to the subject in need thereof comprises a first moiety that binds IL-2R and a second moiety that binds ST2, wherein the first moiety is covalently linked via a linker to a first Fc domain and the second moiety is covalently linked via a linker to a second Fc domain, and the first and second Fc domains are covalently linked, and further wherein the first and second Fc domains are deficient in effector functions.

Autoimmune diseases include diseases that affect organs such as the heart, kidney, liver, lung, reproductive organs, digestive system, or skin. Autoimmune diseases include diseases that affect glands, including the endocrine, adrenal, thyroid, salivary and exocrine glands, and the pancreas. Autoimmune diseases can also be multi-glandular. Autoimmune diseases can target one or more tissues, for example connective tissue, muscle, or blood. Autoimmune diseases can target the nervous system or eyes, ears or vascular system. Autoimmune diseases can also be systemic, affecting multiple organs, tissues and/or systems. In some embodiments, an immune-related disease or condition is an inflammatory disease or condition. In some embodiments, an inflammatory disease or condition is one which involves inflamed muscle, visceral adipose, colon, and/or lung tissue.

In certain embodiments, the autoimmune disease is selected from the group consisting of Graft-vs-Host Disease, Pemphigus Vulgaris, Systemic Lupus Erythematosus, Scleroderma, Ulcerative Colitis, Crohn's Disease, Psoriasis, Type 1 Diabetes, Multiple Sclerosis, Amyotrophic Lateral Sclerosis, Alopecia Areata, Uveitis, Neuromyelitis Optica, and Duchenne Muscular Dystrophy.

In some embodiments, the compounds of the present disclosure treat diseases affecting muscle tissue, for example, inflammatory myopathies, muscular dystrophies, muscle diseases with immune system involvement, and muscle diseases involving inflammation.

Inflammatory myopathies are diseases that typically involve inflammation of the muscles and associated symptoms, such as muscle weakness. The muscle weakness can be progressive. Symptoms associated with inflammatory myopathies (e.g., dermatomyositis) can include, for example, muscle weakness (e.g. proximal muscle weakness), skin rash, fatigue after walking or standing, tripping or falling, dysphagia, dysphonia, difficulty breathing, muscle pain, tender muscles, weight loss, low-grade fever, inflamed lungs, light sensitivity, calcium deposits (calcinosis) under the skin or in the muscle, and biological concomitants of inflammatory myopathies.

Inflammatory myopathies can be caused by allergic reactions, other diseases, exposure to a drug or toxin, or exposure to an infectious agent, or can be idiopathic (no known cause). The inflammatory myopathy can be an acute inflammatory myopathy or a chronic inflammatory myopathy. Inflammatory myopathies can affect both adults and children (e.g., juvenile dermatomyositis). Inflammatory myopathies can include symptoms that affect other organs or systems of the body, such as the skin, lungs, heart, eyes, and gastrointestinal system. In some embodiments, the inflammatory myopathy is a chronic inflammatory myopathy (e.g., dermatomyositis, polymyositis, or inclusion body myositis).

In some embodiments, the inflammatory myopathy can be caused by an allergic reaction, another disease (e.g., cancer or a connective tissue disease), exposure to a toxic substance, a medicine, or an infectious agent (e.g., a virus). In some embodiments, the inflammatory myopathy is associated with lupus, rheumatoid arthritis, or systemic sclerosis. In some embodiments, the inflammatory myopathy is idiopathic. In some embodiments, the inflammatory myopathy is selected from polymyositis, dermatomyositis, inclusion body myositis, and immune-mediated necrotizing myopathy. In some embodiments, the inflammatory myopathy is dermatomyositis.

Biological concomitants of inflammatory myopathies (e.g., dermatomyositis) include, for example, altered (for example, increased) levels of cytokines (for example, Type I interferons (such as IFN-α and/or IFN-β), interleukins (such as IL-6, IL-10, IL-15, IL-17 and IL-18), and TNF-α), TGF-β, B-cell activating factor (BAFF), and overexpression of IFN inducible genes (for example, Type I IFN inducible genes). Other biological concomitants of inflammatory myopathies can include, for example, an increased erythrocyte sedimentation rate (ESR) and/or elevated level of creatine kinase. Further biological concomitants of inflammatory myopathies can include autoantibodies, for example, anti-synthetase autoantibodies (for example, anti-Jo1 antibodies), anti-signal recognition particle antibodies (anti-SRP), anti-Mi-2 antibodies, anti-p155 antibodies, anti-PM/Sci antibodies, and anti-RNP antibodies.

The muscular dystrophies are a group of diverse, heritable neuromuscular disorders that represent a group of devastating neuromuscular diseases characterized by primary or secondary skeletal muscle involvement. Examples of muscular dystrophies include, but are not limited to, Duchenne muscular dystrophy, Beckers muscular dystrophy, Limb-Girdle muscular dystrophy, Facioscapulohumeral muscular dystrophy, Fukuyama congenital muscular dystrophy, and merosin-deficient congenital muscular dystrophy. The most common form of muscular dystrophy is Duchenne Muscular Dystrophy, (DMD). DMD is an X-linked recessive disorder characterized by a mutation in the gene that codes for dystrophin. Most patients die before the age 30 due to respiratory or cardiac failure. Beckers muscular dystrophy (also known as benign pseudohypertrophic muscular dystrophy) is related to DMD in that both result from a mutation in the dystrophin gene. An organism suffering from DMD does not produce functional dystrophin. Thus, DMD is much more severe than BMD.

Subjects

The compounds of the present disclosure are administered to a subject in need thereof, such as a vertebrate. In some embodiments the subject is a mouse, rat, rabbit, dog, cat, horse, sheep, cow, monkey, cynomolgus monkey, or human. Subjects can be, for example, elderly adults, adults, adolescents, pre-adolescents, children, toddlers, and infants. In some embodiments, the subject is an animal model of an inflammatory myopathy. In some embodiments, the subject is a human with an inflammatory myopathy, or a human at risk of developing an inflammatory myopathy. In some embodiments, the subject has a family history of inflammatory myopathy. In some embodiments the subject carries a gene associated with an inflammatory myopathy. In some embodiments the subject is positive for a biomarker associated with an inflammatory myopathy. In some embodiments, the subject has been diagnosed with an inflammatory myopathy. In some embodiments, the subject has one or more signs or symptoms associated with an inflammatory myopathy, e.g., one or more of the symptoms described herein.

In some embodiments the subject is an animal model of a muscular dystrophy. In some embodiments the subject is a human with a muscular dystrophy, or a human at risk of developing a muscular dystrophy. In some embodiments, the subject has a family history of muscular dystrophy. In some embodiments the subject carries a gene associated with a muscular dystrophy. In some embodiments the subject is positive for a biomarker associated with a muscular dystrophy. In some embodiments, the subject has been diagnosed with a muscular dystrophy. In some embodiments, the subject has one or more signs or symptoms associated with a muscular dystrophy, e.g., one or more of the symptoms described herein.

Dosing

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi dose containers with a preservative.

A compound described herein can be present in a composition in a range of from about 0.5 µg to about 7000 µg, from about 1 µg to about 1000 µg, from about 1 µg to about 250 µg, from about 1 µg to about 25 µg, from about 5 µg to about 50 µg, from about 0.5 µg to about 15 µg, or from about 0.5 µg to about 10 µg per dose.

A compound described herein can be present in a composition in an amount of about 0.5 µg, about 1 µg, about 2 µg, about 3 µg, about 4 µg, about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, about 40 µg, about 41 µg, about 42 µg, about 43 µg, about 44 µg, about 45 µg, about 46 µg, about 47 µg, about 48 µg, about 49 µg, about 50 µg, about 55 µg, about 60 µg, about 65 µg, about 70 µg, about 75 µg, about 80 µg, about 85 µg, about 90 µg, about 95 µg, about 100 µg, about 125 µg, about 150 µg, about 175 µg, about 200 µg, about 250 µg, about 300 µg, about 350 µg, about 400 µg, about 450 µg, about 500 µg, about 550 µg, about 600 µg, about 650 µg, about 700 µg, about 750 µg, about 800 µg, about 850 µg, about 900 µg, about 950 µg, about 1000 µg, about 1050 µg, about 1100 µg, about 1150 µg, about 1200 µg, about 1250 µg, about 1300 µg, about 1350 µg, about 1400 µg, about 1450 µg, about 1500 µg, about 1550 µg, about 1600 µg, about 1650 µg, about 1700 µg, about 1750 µg, about 1800 µg, about 1850 µg, about 1900 µg, about 1950 µg, about 2000 µg, about 2500 µg, about 3000 µg, about 3500 µg, about 4000 µg, about 4500 µg, about 5000 µg, about 5500 gig, about 6000 µg, about 6500 µg, about 7000 µg, about 7500 µg, about 8000 µg, about 9000 µg, about 10,000 µg (10 mg), about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 mg. Any of these values may be used to define a range for the amount of the compound in the composition. For example, the compound may be present in a composition in the range of from about 0.5 µg to about 40 mg, from about 500 µg to about 10 mg, or from about 50 µg to about 5 mg.

In some embodiments, a dose can be expressed in terms of an amount of the drug divided by the mass of the subject, for example, micrograms or milligrams of drug per kilograms of subject body mass. In some embodiments, the compound is administered at a dose of about 0.5 µg/kg, about 1 µg/kg, about 2 µg/kg, about 3 µg/kg, about 4 µg/kg, about 5 µg/kg, about 6 µg/kg, about 7 µg/kg, about 8 µg/kg, about 9 µg/kg, about 10 µg/kg, about 11 µg/kg, about 12 µg/kg, about 13 µg, about 14 µg/kg, about 15 µg/kg, about 16 µg/kg, about 17 µg/kg, about 18 µg/kg, about 19 µg/kg, about 20 µg/kg, about 25 µg/kg, about 30 µg/kg, about 35 µg/kg, about 40 µg/kg, about 45 µg/kg, about 50 µg/kg, about 55 µg/kg, about 60 µg/kg, about 65 µg/kg, about 70 µg/kg, about 75 µg/kg, about 80 µg/kg, about 85 µg/kg, about 90 µg/kg, about 95 µg/kg, about 100 µg/kg, about 125 µg/kg, about 150 µg/kg, about 175 µg/kg, about 200 µg/kg, about 250 µg/kg, about 300 µg/kg, about 350 µg/kg, about 400 µg/kg, about 450 µg/kg, about 500 µg/kg, about 550 1µg/kg, about 600 µg/kg, about 650 µg/kg, about 700 µg/kg, about 750 µg/kg, about 800 µg/kg, about 850 µg/kg, about 900 µg/kg, about 950 µg/kg, about 1000 µg/kg, about 1050 µg/kg, about 1100 µg/kg, about 1150 µg/kg, about 1200 µg/kg, about 1250 µg/kg, about 1300 µg/kg, about 1350 µg/kg, about 1400 µg/kg, about 1450 µg/kg, about 1500 µg/kg, about 1550 µg/kg, about 1600 µg/kg, about 1650 µg/kg, about 1700 µg/kg, about 1750 µg/kg, about 1800 µg/kg, about 1850 µg/kg, about 1900 µg/kg, about 1950 µg/kg, about 2000 µg/kg, about 2500 µg/kg, about 3000 µg/kg, about 3500 µg/kg, about 4000 µg/kg, about 4500 µg/kg, or about 5000 µg/kg. Any of these values may be used to define a range for the dose of the compound. For example, in some embodiments, a compound is administered at a dose ranging from about 0.5 µg/kg to about 250 µg/kg, 1 µg/kg to about 200 µg/kg, 5 µg/kg to about 150 µg/kg, about 10 µg/kg to about 100 µg/kg, about 10 µg/kg to about 50 µg/kg, about 15 µg/kg to about 35 µg/kg, or about 0.5 µg/kg to about 5000 µg/kg.

The disclosed compounds can be administered at any interval desired. For example, the compound can be administered once a week, 2 times a week, 3 times a week, 4 times a week, 5 times a week, 6 times a week, 7 times a week, 8 times a week, 9 times a week, or 10 times a week. The interval between daily dosing can be any hourly interval, for example, every hour, every 2 hours, every 3 hours, every 4 hours, every 5 hours, every 6 hours, every 7 hours, every 8 hours, every 9 hours, every 10 hours, every 11 hours, or every 12 hours. The compound can be administered once every week, once every 2 weeks, once every 3 weeks, once every 4 weeks, once every 5 weeks, once every 6 weeks, once every 7 weeks, or once every 8 weeks. The administration of the compound can have irregular dosing schedules to accommodate either the person administering the compound or the subject receiving the compound. As such, the compound can be administered, for example, once a day, twice a day, or three times a day.

The amount administered can be the same amount in each dose or the dosage can vary. For example, a first amount can be dosed in the morning and a second amount can be administered in the evening. A subject could receive a high first dose and lower subsequent doses. The dose can be adjusted up or down depending on improvement in symptoms or markers of the disease, or development of adverse reactions.

Non-limiting examples of pharmaceutically-acceptable carriers include saline, Ringer's solution and dextrose solution. Liquid carriers can be used in preparing solutions, suspensions, and emulsions. A compound described herein can be dissolved or suspended in a pharmaceutically-acceptable liquid carrier such as water, an organic solvent, or a mixture of both, or pharmaceutically-acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for parenteral administration include water, alcohols (including monohydric alcohols and polyhydric alcohols, e.g., glycols) and derivatives thereof, and oils (e.g., fractionated coconut oil and arachis oil). For parenteral administration, the carrier can be an oily ester such as ethyl oleate or isopropyl myristate. Sterile liquid carriers are used in sterile liquid form compositions for parenteral administration. The pH of the solution is can be from about 5 to about 8, for example, from about 7 to about 7.5.

In some embodiments, treatment with a molecule of the present disclosure is better tolerated than is treatment with a wildtype IL-2 polypeptide. In some embodiments, treatment with a therapeutically-effective dose of a molecule of the present disclosure causes fewer incidents of diarrhea relative to treatment with IL2(C125S). In some embodiments, treatment with a therapeutically-effective amount of a molecule of the present disclosure does not cause capillary leak syndrome. In some embodiments, treatment with a therapeutically-effective amount of a molecule of the present disclosure does not cause decreased neutrophil activity or increased risk of infection.

The compounds of the present disclosure have high, moderate, or low affinity for the IL-2 receptor. The compounds of the present disclosure have high, moderate, or low affinity for ST2. A compound that has moderate or low affinity for IL2R and ST2 individually can have high avidity when both receptors are present on a cell. A compound of the present disclosure has a dissociation constant (Kd) of, for example, from about 1 pmol to about 1 mmol, from about 10 pmol to about 1 mmol, from about 100 pmol to about 1 mmol, from about 1 µmol to about 1 mmol, from about 10 µmol to about 1 mmol, from about 1 µmol to about 100 µmol, from about 1 µmol to about 500 µmol, from about 200 µmol to about 800 µmol, from about 10 µmol to about 100 µmole, or from about 500 µmole to about 1 mmol for binding to either ST2 or IL2R individually. A compound of the present disclosure can have a lower apparent Kd when binding to both ST2 and IL-2R, for example, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 4%, less than 3%, less than 2%, or less than 1% of an individual Kd.

Pharmacokinetics

A dose can be modulated to achieve a desired pharmacokinetic (PK) or pharmacodynamics profile, such as a desired or effective blood profile, as described herein.

Pharmacokinetic and pharmacodynamic data can be obtained by various experimental techniques. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined, for example, by calculating the average of all subject's measurements for each parameter measured. A dose can be modulated to achieve a desired pharmacokinetic or pharmacodynamics profile, such as a desired or effective blood profile, as described herein.

The pharmacodynamic parameters can be any parameters suitable for describing compositions of the invention. For example, the pharmacodynamic profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, about 24 hours, about 2 days, about 3 days, about 4 days, about 5 days, about 6 days, about 7 days, about 8 days, about 9 days, about 10 days, about 11 days, about 12 days, about 13 days, or about 14 days.

The pharmacokinetic parameters can be any parameters suitable for describing a compound. The $C_{max}$ can be, for example, not less than about 1 ng/mL; not less than about 5 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; not less than about 2500 ng/mL; or any other $C_{max}$ appropriate for describing a pharmacokinetic profile of a compound described herein. The $C_{max}$ can be, for example, about 5 to about 10,000 ng/mL, about 50 to about 10,000 ng/mL, about 500 to about 10,000 ng/mL, about 5000 to about 10,000 ng/mL, about 1000 to about 5,000 ng/mL, about 1000 to about 3,000 ng/mL, about 5,000 to about 8,000 ng/mL or about 500 to about 1000 ng/mL in blood when administered by intravenous injection, for example, at 50 µg/kg. The $C_{max}$ can be, for example, about 5 to about 50 ng/mL, about 50 to about 500 ng/mL, about 100 to about 250 ng/mL, about 1000 to about 5000 ng/mL, about 1000 to about 2000 ng/mL, about 2000 to about 5000 ng/mL, about 5000 to about 10000 ng/mL or about 5000 to about 7000 ng/mL in blood when administered by subcutaneous injection, for example, at 50 µg/kg. The Cmax can depend on the dose of compound received. The dose received can be 50 µg/kg, 100 µg/kg, 200 µg/kg, 250 µg/kg, 300 µg/kg, 400 µg/kg, 500 µg/kg, 600 µg/kg, 700 µg/kg, 800 µg/kg, 900 µg/kg, or 1000 µg/kg.

The $T_{max}$ of a compound described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, not greater than about 5.5 hours, not greater than about 6 hours, not greater than about 6.5 hours, not greater than about 7 hours, not greater than about 7.5 hours, not greater than about 8 hours, not greater than about 8.5 hours, not greater than about 9 hours, not greater than about 9.5 hours, not greater than about 10 hours, not greater than about 10.5 hours, not greater than about 11 hours, not greater than about 11.5 hours, not greater than about 12 hours, not greater than about 12.5 hours, not greater than about 13 hours, not greater than about 13.5 hours, not greater than about 14 hours, not greater than about 14.5 hours, not greater than about 15 hours, not greater than about 15.5 hours, not greater than about 16 hours, not greater than about 16.5 hours, not greater than about 17 hours, not greater than about 17.5 hours, not greater than about 18 hours, not greater than about 18.5 hours, not greater than about 19 hours, not greater than about 19.5 hours, not greater than about 20 hours, or any other $T_{max}$ appropriate for describing a pharmacokinetic profile of a compound described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0-inf)}$ (also called $AUC_{(0-\infty)}$) or $AUC_{(last)}$ of a compound described herein can be, for example, not less than about 1 ng·hr/mL, not less than about 5 ng·hr/mL, not less than about 10 ng·hr/mL, not less than about 20 ng·hr/mL, not less than about 30 ng·hr/mL, not less than about 40 ng·hr/mL, not less than about 50 ng·hr/mL, not less than about 100 ng·hr/mL, not less than about 150 ng·hr/mL, not less than about 200 ng·hr/mL, not less than about 250 ng·hr/mL, not less than about 300 ng·hr/mL, not less than about 350 ng·hr/mL, not less than about 400 ng·hr/mL, not less than about 450 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 1250 ng·hr/mL, not less than about 1500 ng·hr/mL, not less than about 1750 ng·hr/mL, not less than about 2000 ng·hr/mL, not less than about 2500 ng·hr/mL, not less than about 3000 ng·hr/mL, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, not less than about 10,000 ng·hr/mL, not less than about 11,000 ng·hr/mL, not less than about 12,000 ng·hr/mL, not less than about 13,000 ng·hr/mL, not less than about 14,000 ng·hr/mL, not less than about 15,000 ng·hr/mL, not less than about 16,000 ng·hr/mL, not less than about 17,000 ng·hr/mL, not less than about 18,000 ng·hr/mL, not less than about 19,000 ng·hr/mL, not less than about 20,000 ng·hr/mL, or any other $AUC_{(0-inf)}$ appropriate for describing a pharmacokinetic profile of a compound described herein. The $AUC_{(0-inf)}$ of a compound can be, for example, about 1 ng·hr/mL to about 10,000 ng·hr/mL; about 1 ng·hr/mL to about 10 ng·hr/mL; about 10 ng·hr/mL to about 25 ng·hr/mL; about 25 ng·hr/mL to about 50 ng·hr/mL; about 50 ng·hr/mL to about 100 ng·hr/mL; about 100 ng·hr/mL to about 200 ng·hr/mL; about 200 ng·hr/mL to about 300 ng·hr/mL; about 300 ng·hr/mL to about 400 ng·hr/mL; about 400 ng·hr/mL to about 500 ng·hr/mL; about 500 ng·hr/mL to about 600 ng·hr/mL; about 600 ng·hr/mL to about 700 ng·hr/mL; about 700 ng-hr/mL, to about 800 ng·hr/mL; about 800 ng·hr/mL to about 900 ng·hr/mL; about 900 ng·hr/mL to about 1,000 ng·hr/mL; about 1,000 ng·hr/mL to about 1,250 ng·hr/mL; about 1,250 ng·hr/mL to about 1,500 ng·hr/mL; about 1,500 ng·hr/mL to about 1,750 ng·hr/mL; about 1,750 ng·hr/mL to about 2,000 ng·hr/mL; about 2,000 ng·hr/mL to about 2,500 ng·hr/mL; about 2,500 ng·hr/mL to about 3,000 ng·hr/mL; about 3,000 ng·hr/mL to about 3,500 ng·hr/mL; about 3,500 ng·hr/mL to about 4,000 ng·hr/mL; about 4,000 ng·hr/mL to about 4,500 ng·hr/mL; about 4,500 ng·hr/mL to about 5,000 ng·hr/mL; about 5,000 ng·hr/mL to about 5,500 ng·hr/mL; about 5,500 ng·hr/mL to about 6,000 ng·hr/mL; about 6,000 ng·hr/mL to about 6,500 ng·hr/mL; about 6,500 ng·hr/mL to about 7,000 ng·hr/mL; about 7,000 ng·hr/mL to about 7,500 ng·hr/mL; about 7,500 ng·hr/mL to about 8,000 ng·hr/mL; about 8,000 ng·hr/mL to about 8,500 ng·hr/mL; about 8,500 ng·hr/mL to about 9,000 ng·hr/mL; about 9,000 ng·hr/mL to about 9,500 ng·hr/mL; about 9,500 ng·hr/mL to about 10,000 ng·hr/mL; about 10,000 ng·hr/mL to about 10,500 ng·hr/mL; about 10,500 ng·hr/mL to about 11,000 ng·hr/mL; about 11,000 ng·hr/mL to about 11,500 ng·hr/mL; about 11,500 ng·hr/mL to about 12,000 ng·hr/mL; about 12,000 ng·hr/mL to about 12,500 ng·hr/mL; about 12,500 ng·hr/mL to about 13,000 ng·hr/mL; about 13,000 ng·hr/mL to about 13,500 ng·hr/mL; about 13,500 ng·hr/mL to about 14,000 ng·hr/mL; about 14,000 ng·hr/mL to about 14,500 ng·hr/mL; about 14,500 ng·hr/mL to about 15,000 ng·hr/mL; about 15,000 ng·hr/mL to about 15,500 ng·hr/mL; about 15,500 ng·hr/mL to about 16,000 ng·hr/mL; about 16,000 ng·hr/mL to about 16,500 ng·hr/mL; about 16,500 ng·hr/mL to about 17,000 ng·hr/mL; about 17,000 ng·hr/mL to about 17,500 ng·hr/mL; about 17,500 ng·hr/mL to about 18,000 ng·hr/mL; about 18,000 ng·hr/mL to about 18,500 ng·hr/mL; about 18,500 ng·hr/mL to about 19,000 ng·hr/mL; about 19,000 ng·hr/mL to about 19,500 ng·hr/mL; or about 19,500 ng·hr/mL to about 20,000 ng·hr/mL. For example, the $AUC_{(0-inf)}$ of a compound can be about 8500 ng·hr/mL when administered intravenously at 50 µg/kg or about 4000 ng·hr/mL when administered subcutaneously at 50 µg/kg.

The plasma concentration of a compound described herein can be, for example, not less than about 1 ng/mL, not less than about 5 ng/mL, not less than about 10 ng/mL, not less than about 15 ng/mL, not less than about 20 ng/mL, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a compound described herein. The plasma concentration can be, for example, about 1 ng/mL to about 2,000 ng/mL; about 1 ng/mL to about 5 ng/mL; about 5 ng/mL to about 10 ng/mL; about 10 ng/mL to about 25 ng/mL; about 25 ng/mL to about 50 ng/mL; about 50 ng/mL to about 75 ng/mL; about 75 ng/mL to about 100 ng/mL; about 100 ng/mL to about 150 ng/mL; about 150 ng/mL to about 200 ng/mL; about 200 ng/mL to about 250 ng/mL; about 250 ng/mL to about 300 ng/mL; about 300 ng/mL to about 350 ng/mL; about 350 ng/m, to about 400 ng/mL; about 400 ng/mL to about 450 ng/mL; about 450 ng/mL to about 500 ng/mL; about 500 ng/mL to about 600 ng/mL; about 600 ng/mL to about 700 ng/mL; about 700 ng/mL to about 800 ng/mL; about 800 ng/mL to about 900 ng/mL; about 900 ng/mL to about 1,000 ng/mL; about 1,000 ng/mL to about 1,100 ng/mL; about 1,100 ng/mL to about 1,200 ng/mL; about 1,200 ng/mL to about 1,300 ng/mL; about 1,300 ng/mL to about 1,400 ng/mL; about 1,400 ng/mL to about 1.500 ng/mL; about 1,500 ng/mL to about 1,600 ng/mL; about 1,600 ng/mL to about 1,700 ng/mL; about 1,700 ng/mL to about 1,800 ng/mL; about 1,800 ng/mL to about 1,900 ng/mL; or about 1,900 ng/mL to about 2,000 ng/mL.

The pharmacodynamic parameters can be any parameters suitable for describing compositions of the disclosure. For example, the pharmacodynamic profile can exhibit increased Treg cell counts for, for example, about 24 hours, about 48 hours, about 72 hours, or 1 week.

Non-limiting examples of pharmacodynamic and pharmacokinetic parameters that can be calculated for a compound that is administered with the methods of the invention include: a) the amount of drug administered, which can be represented as a dose D; b) the dosing interval, which can be represented as r; c) the apparent volume in which a drug is distributed, which can be represented as a volume of distribution $V_d$, where $V_d=D/C_0$; d) the amount of drug in a given volume of plasma, which can be represented as concentration $C_0$ or $C_{ss}$, where $C_0$ or $C_{ss}=D/Vd$ and can be represented as a mean plasma concentration over a plurality of samples; e) the half-life of a drug $t_{1/2}$, where $t_{1/2}=\ln(2)/k_e$; f) the rate at which a drug is removed from the body $k_e$, where $k_e=\ln(2)/t_{1/2}=CL/V_d$; g) the rate of infusion required to balance the equation $K_{in}$, where $K_{in}=C_{ss}\cdot CL$; h) the integral of the concentration-time curve after administration of a single dose, which can be represented as $AUC_{0-\infty}$, wherein $\int_0^\infty C\,dt$, or in steady-state, which can be represented as $AUC\tau,_{ss}$, wherein $\int_t^{t+\tau} C\,dt$; i) the volume of plasma cleared of the drug per unit time, which can be represented as CL (clearance), wherein $CL=V_d\cdot k_e=D/AUC$; j) the systemically available fraction of a drug, which can be represented as f, where $$f = \frac{AUCpo.Div}{AUCiv.Dpo}; k)$$

the peak plasma concentration of a drug after administration $C_{max}$; l) the time taken by a drug to reach $C_{max}$, $t_{max}$; m) the lowest concentration that a drug reaches before the next dose is administered $C_{min}$; and n) the peak trough fluctuation within one dosing interval at steady state, which can be represented as % PTF=100.

$$\frac{(Cmax, ss - Cmin, ss)}{Cav, ss} \text{ where } C_{av,ss} = \frac{AUC\tau, ss}{\tau}.$$

The compounds of the present disclosure can have high stability when administered to a subject. The administered compound can have a physiological half-life of greater than about 6 hrs, greater than about 7 hrs, greater than about 8 hrs, greater than about 9 hrs, greater than about 10 hrs, greater than about 11 hrs, greater than about 12 hrs, greater than about 13 hrs, greater than about 14 hrs, greater than about 15 hrs, greater than about 16 hrs, greater than about 17 hrs, greater than about 18 hrs, greater than about 19 hrs, greater than about 20 hrs, greater than about 21 hrs, greater than about 22 hrs, greater than about 23 hrs, greater than about 24 hrs, greater than about 25 hrs, greater than about 26 hrs, greater than about 27 hrs, greater than about 28 hrs, greater than about 29 hrs, greater than about 30 hrs, greater than about 31 hrs, greater than about 32 hrs, greater than about 33 hrs, greater than about 34 hrs, greater than about 35 hrs, greater than about 36 hrs, greater than about 37 hrs, greater than about 38 hrs, greater than about 39 hrs, greater than about 40 hrs, greater than about 41 hrs, greater than about 42 hrs, greater than about 43 hrs, greater than about 44 hrs, greater than about 45 hrs, greater than about 46 hrs, greater than about 47 hrs, greater than about 48 hrs, greater than about 49 hrs, greater than about 50 hrs, greater than about 51 hrs, greater than about 52 hrs, greater than about 53 hrs, greater than about 54 hrs, greater than about 55 hrs, greater than about 56 hrs, greater than about 57 hrs, greater than about 58 hrs, greater than about 59 hrs, greater than about 60 hrs, greater than about 61 hrs, greater than about 62 hrs, greater than about 63 hrs, or greater than about 64 hrs.

The half-life of a compound of the present disclosure can vary based on the dose administered. For example, the half-life of the compound when administered in a dose of 50 μg/kg can be shorter than the half-life of the same compound when administered at a dose of 100 μg/kg or 250 μg/kg. The half-life of the compound can vary based on the administration route used. The half-life of the compound can be longer if the compound is administered subcutaneously rather than intravenously. For example the half-life of a compound delivered subcutaneously can be between about 15 hrs and about 25 hrs, while the half-life of the compound delivered intravenously can be between about 5 and about 15 hrs. In some embodiments, the half-life of a compound when administered intravenously at 50 μg/kg is about 6 hrs to about 14 hrs, about 7 hrs to about 13 hours, about 8 hrs to about 12 hrs, or about 9 hrs to about 11 hrs. In some embodiments, the half-life of a compound when administered intravenously at 50 μg/kg is about 5 hrs, about 6 hrs, about 7 hrs, about 8 hrs, about 9 hrs, about 10 hrs, about 11 hrs, about 12 hrs, about 13 hrs, about 14 hrs, or about 15 hrs. In some embodiments, the half-life of a compound when administered subcutaneously at 50 μg/kg is about 15 hrs to about 27 hrs, about 16 hrs to about 26 hours, about 17 hrs to about 25 hrs, about 18 hrs to about 24 hrs, about 19 hrs to about 23 hrs, or about 20 hrs to about 22 hrs. In some embodiments, the half-life of a compound when administered subcutaneously at 50 μg/kg is about 10 hrs, about 11 hrs, about 12 hrs, about 13 hrs, about 14 hrs, about 15 hrs, about 16 hrs, about 17 hrs, about 18 hrs, about 19 hrs, about 21 hrs, about 22 hrs, about 23 hrs, about 24 hrs, about 25 hrs, about 26 hrs, about 27 hrs, about 28 hrs, about 29 hrs, or about 30 hrs. The clearance of the compound from the blood can be faster for a compound delivered intravenously than for a compound delivered subcutaneously.

Production of Dimeric Proteins: Heterodimers and Homodimers

In some embodiments, a compound of the present disclosure is a heterodimer, for example, a heterodimer comprising an IL2R-binding moiety (e.g. IL-2 or an IL-2 variant) that is part of a first fusion protein and an ST2-binding moiety (e.g. IL-33, an IL-33 variant, an antibody that binds ST2, or an antigen-binding fragment thereof) that is part of a second fusion protein. In some embodiments, each of the first and second fusion proteins comprises an IgG Fc domain, for example an IgG1 Fc domain or variant thereof. Heterodimers can be produced by expressing the two constituent recombinant proteins individually, purifying them, and combining them in vitro to form disulfide-linked heterodimers. Heterodimeric Fc fusion proteins can also be made in a single cell transfected with two constituent cDNA constructs using the "knobs into holes" approach. By this strategy, mutations are introduced into the CH2-CH3 interface between the two Fc polypeptide chains that prevent the formation of homodimers, yet form complementary interfaces that promote the formation of heterodimers. In this manner, heterodimeric Fc fusion proteins can be formed within host cells expressing the recombinant proteins and secreted as heterodimeric proteins. Below are two examples such Fc constructs on a human IgG1 background. The mutated residues T366Y and Y407T are shown in bold and underlined, and the N297A residue is underlined.

```
(A) IgG1 Fc (N297A; T366-Y):
                                         (SEQ ID NO: 8)
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNGKEYK

CKVSNKALPAPIEKTISKAKGQPREPQVYTLPPSRDELTKNQVSLYCLVK

GFYPSDIAVEWESNGQPENNYKTTPPVLDSDGSFFLYSKLTVDKSRWQQG

NVFSCSVMHEALHNHYTQKSLSLSPG (B) IgG1 Fc (N-297A; Y407T):
                                         (SEQ ID NO: 9)
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLTSKLTVDKSRWQQG

NVFSCSVMHEALHNHYTQKSLSLSPG
```

The two different binding moieties, for instance, IL-2 and IL-33, can be appended to the Fc sequences (A) and (B), respectively, to construct a heterodimeric protein.

In some embodiments, the first fusion protein comprises an IgG1 Fc domain comprising the mutations T350V, L351Y, F405A and Y407V (e.g. SEQ ID NO: 4); and the second fusion protein comprises the mutations T350V, T366L, K392L and T394W (e.g. SEQ ID NO: 5). Such mutations have been reported to improve proper pairing and stability (Von Kreudenstein et al., 2013, mAbs 5: 646-654; WO 2014082179 A1). Exemplary human IgG1 Fc domain sequences are shown below with the N297A mutation underlined, and the T350V, L351Y, F405A, Y407V, T350V, T366L, K392L and T394W mutations shown in bold and underlined.

```
IgG1 Fc (N297A, T350V, L351Y, F405A and Y407V)
                                         (SEQ ID NO: 4)
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNGKEYK

CKVSNKALPAPIEKTISKAKGQPREPQVYVYPPSRDELTKNQVSLTCLVK

GFYPSDIAVEWESNGQPENNYKTTPPVLDSDGSFALVSKLTVDKSRWQQG

NVFSCSVMHEALHNHYTQKSLSLSPG (B) IgG1 Fc (N297A, T350V, T366L, K392L and
T7394W)
                                         (SEQ ID NO: 5)
DKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNGKEYK
```

-continued

```
CKVSNKALPAPIEKTISKAKGQPREPQVYVLPPSRDELTKNQVSLLCLVK

GFYPSDIAVEWESNGQPENNYLTWPPVLDSDGSFFLYSKLTVDKSRWQQG

NVFSCSVMHEALHNHYTQKSLSLSPG
```

Exemplary heterodimers are shown in FIGS. 4A, 4B, 4C, 4D and 4E.

In some embodiments, a compound of the present disclosure is a homodimer, for example, a homodimer comprising two identical fusion proteins, each containing an IL2R-binding moiety (e.g. IL-2 or an IL-2 variant) and an ST2-binding moiety (e.g. IL-33, an IL-33 variant, an antibody that binds ST2, or an antigen-binding fragment thereof). In some embodiments, each of the two identical fusion proteins comprises an IgG Fc domain, for example an IgG1 Fc domain or variant thereof. In a particular embodiment, the IgG1 Fc domain is a human IgG1 Fc domain comprising the N297A mutation (e.g. SEQ ID NO: 7). Exemplary homodimers are shown in FIGS. 1F and 1G.

The IL2R-binding moiety (e.g. IL-2 or an IL-2 variant) and the ST2-binding moiety (e.g. IL-33, an IL-33 variant, an antibody that binds ST2, or an antigen-binding fragment thereof) may be attached to the N-terminus or the C-terminus of the IgG Fc domain, either directly or through a peptide linker (e.g. a $G_4S$ linker). Various combinations of an IL2R-binding moiety and an ST2-binding moiety may be used. In some embodiments, the dimeric protein comprises a first fusion protein comprising an IL2R-binding moiety N-terminal to the IgG Fc domain, and a second fusion protein comprising an ST2-binding moiety C-terminal to the IgG Fc domain (see, for example, FIG. 4A). In some embodiments, the first fusion protein comprises an IL2R-binding moiety N-terminal to the IgG Fc domain, and the second fusion protein comprises an ST2-binding moiety N-terminal to the IgG Fc domain (see, for example, FIGS. 4B and 5D). In some embodiments, the first fusion protein comprises an IL2R-binding moiety C-terminal to the IgG Fc domain, and the second fusion protein comprises an ST2-binding moiety N-terminal to the IgG Fc domain (see, for example, FIGS. 4C and 5C). In some embodiments, the first fusion protein comprises an IL2R-binding moiety C-terminal to the IgG Fc domain, and the second fusion protein comprises an ST2-binding moiety C-terminal to the IgG Fc domain. In some embodiments, the first fusion protein comprises an ST2-binding moiety N terminal to the IgG Fc domain and an IL2R-binding moiety C-terminal to the IgG Fc domain, and the second fusion protein comprises an ST2-binding moiety N-terminal to the IgG Fc domain (see, for example, FIGS. 4D and 5B). In some embodiments, the first fusion protein comprises an ST2-binding moiety N terminal to the IgG Fc domain and an IL2R-binding moiety C-terminal to the IgG Fc domain, and the second fusion protein comprises an IL2R-binding moiety N-terminal to the IgG Fc domain (see, for example, FIG. 4E). In some embodiments, both the first fusion protein and the second fusion protein comprise an ST2-binding moiety N terminal to the IgG Fc domain and an IL2R-binding moiety C-terminal to the IgG Fc domain (see, for example, FIG. 4F and FIG. 5A). In some embodiments, both the first fusion protein and the second fusion protein comprise an IL2R-binding moiety N terminal to the IgG Fc domain and an ST2-binding moiety C-terminal to the IgG Fc domain (see, for example, FIG. 4G). In some embodiments, the first fusion protein comprises an IL2R-binding moiety C-terminal to the IgG Fc domain, and the second fusion protein comprises an ST2- binding moiety N-terminal to the IgG Fc domain and an IL2R-binding moiety C-terminal to the IgG Fc domain (see, for example, FIG. 5E).

In some embodiments, the dimeric protein comprises at least one IL2R-binding moiety (e.g. IL-2 or an IL-2 variant) and at least one ST2-binding moiety (e.g. IL-33, an IL-33 variant, an antibody that binds ST2, or an antigen-binding fragment thereof). In some embodiments, the dimeric protein comprises only one IL2R-binding moiety. In some embodiments, the dimeric protein comprises only one ST2-binding moiety.

In some embodiments, the dimeric protein comprises at least two IL2R-binding moieties. For example, in some embodiments, the first and second fusion protein each contain at least one IL2R-binding moiety. See, for example, FIGS. 4E, 4F and 4G. In some embodiments, the dimeric protein comprises at least two ST2-binding moieties. For example, in some embodiments, the first and second fusion protein each contain at least one ST2-binding moiety. See, for example, FIGS. 4D, 4F, and 4G.

In any of the embodiments described herein, the IL2R-binding moiety and the ST2-binding moiety may be attached to the IgG Fc domain via a peptide linker (e.g. a $G_4S$ linker). The dimeric protein may contain, 1, 2, 3, 4 or more peptide linkers. In some embodiments, the dimeric protein comprises at least 1, 2, 3 or 4 peptide linkers.

In some embodiments, the IL2R-binding moiety and/or the ST2-binding moiety is fused directly to the IgG Fc domain through a peptide bond, i.e. without the addition of a peptide linker between the binding moiety and the IgG Fc domain. In some embodiment, the dimeric protein does not comprise a peptide linker.

In some embodiments, the first fusion protein of the dimeric protein is configured so that the C-terminus of the IL-2 binding moiety (e.g. a human IL-2 protein domain or a variant thereof) is fused through a peptide bond to the N-terminus of a first peptide linker domain; and the N-terminus of the first IgG Fc protein domain is fused through a peptide bond to the C-terminus of the first peptide linker domain. In some embodiments, the second fusion protein of the dimeric protein is configured so that the C-terminus of a second IgG Fc protein domain is fused through a peptide bond to the N-terminus of a second peptide linker domain; and the N-terminus of a protein domain that binds to ST2 is fused through a peptide bond to the C-terminus of the second peptide linker domain. See, for example, FIG. 4A. In some embodiments, the second fusion protein of the dimeric protein is configured so that the C-terminus of the ST2 binding moiety is fused through a peptide bond to the N-terminus of a second peptide linker domain; and the N-terminus of the second IgG Fc protein domain is fused through a peptide bond to the C-terminus of the second peptide linker domain. See, for example, FIG. 4B.

In some embodiments, the dimeric protein comprises a fusion protein having at least 90%, at least 95%, at least 96%, at least 97%, at least 98%, or at least 99% sequence identity to the amino acid sequence of SEQ ID NO: 12. In some embodiments, the dimeric protein comprises a fusion protein having at least 90%, at least 95%, at least 96%, at least 97%, at least 98%, or at least 99% sequence identity to the amino acid sequence of SEQ ID NO: 13. In some embodiments, the dimeric protein comprises a fusion protein having at least 90%, at least 95%, at least 96%, at least 97%, at least 98%, or at least 99% sequence identity to the amino acid sequence of SEQ ID NO: 14. In some embodiments, the dimeric protein comprises a fusion protein having at least 90%, at least 95%, at least 96%, at least 97%, at least 98%, or at least 99% sequence identity to the amino acid sequence of SEQ ID NO: 15. In some embodiments, the dimeric protein comprises a fusion protein having at least 90%, at least 95%, at least 96%, at least 97%, at least 98%, or at least 99% sequence identity to the amino acid sequence of SEQ ID NO: 16. In some embodiments, the dimeric protein comprises a fusion protein having at least 90%, at least 95%, at least 96%, at least 97%, at least 98%, or at least 99% sequence identity to the amino acid sequence of SEQ ID NO: 17. In some embodiments, the dimeric protein comprises a fusion protein having at least 90%, at least 95%, at least 96%, at least 97%, at least 98%, or at least 99% sequence identity to the amino acid sequence of SEQ ID NO: 18. In some embodiments, the dimeric protein comprises a fusion protein having at least 90%, at least 95%, at least 96%, at least 97%, at least 98%, or at least 99% sequence identity to the amino acid sequence of SEQ ID NO: 19. In some embodiments, the dimeric protein comprises a fusion protein having at least 90%, at least 95%, at least 96%, at least 97%, at least 98%, or at least 99% sequence identity to the amino acid sequence of SEQ ID NO: 20. In some embodiments, the dimeric protein comprises a fusion protein having at least 90%, at least 95%, at least 96%, at least 97%, at least 98%, or at least 99% sequence identity to the amino acid sequence of SEQ ID NO: 21. In some embodiments, the dimeric protein comprises a fusion protein having at least 90%, at least 95%, at least 96%, at least 97%, at least 98%, or at least 99% sequence identity to the amino acid sequence of SEQ ID NO: 22. In some embodiments, the dimeric protein comprises a fusion protein having at least 90%, at least 95%, at least 96%, at least 97%, at least 98%, or at least 99% sequence identity to the amino acid sequence of SEQ ID NO: 23. In some embodiments, the dimeric protein comprises a fusion protein having at least 90%, at least 95%, at least 96%, at least 97%, at least 98%, or at least 99% sequence identity to the amino acid sequence of SEQ ID NO: 24. In some embodiments, the dimeric protein comprises a fusion protein having at least 90%, at least 95%, at least 96%, at least 97%, at least 98%, or at least 99% sequence identity to the amino acid sequence of SEQ ID NO: 25. In some embodiments, the dimeric protein comprises a fusion protein having at least 90%, at least 95%, at least 96%, at least 97%, at least 98%, or at least 99% sequence identity to the amino acid sequence of SEQ ID NO: 26. In some embodiments, the dimeric protein comprises a fusion protein having at least 90%, at least 95%, at least 96%, at least 97%, at least 98%, or at least 99% sequence identity to the amino acid sequence of SEQ ID NO: 27. In some embodiments, the dimeric protein comprises a fusion protein having at least 90%, at least 95%, at least 96%, at least 97%, at least 98%, or at least 99% sequence identity to the amino acid sequence of SEQ ID NO: 28. In some embodiments, the dimeric protein comprises a fusion protein having at least 90%, at least 95%, at least 96%, at least 97%, at least 98%, or at least 99% sequence identity to the amino acid sequence of SEQ ID NO: 29. In some embodiments, the dimeric protein comprises a fusion protein having at least 90%, at least 95%, at least 96%, at least 97%, at least 98%, or at least 99% sequence identity to the amino acid sequence of SEQ ID NO: 30.

Description of Sequences in Sequence Listing

Figure 4A:
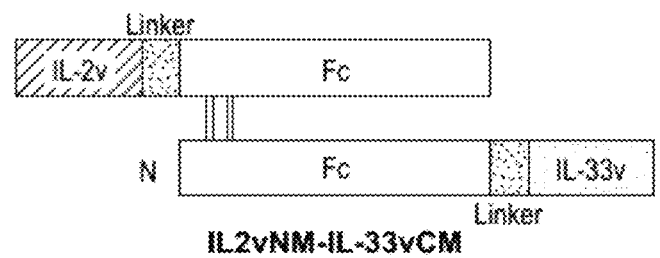
FIG. 4A-4J show schematic diagrams of dimeric proteins comprising IgG1 Fc regions. The dimeric proteins comprise an IL-33 variant (C208S, C227S, C232S, C259S), or various combinations of the IL-33 variant and an IL-2 variant (N88R, C125S). In the protein names, "N" indicates N-terminal, "C" indicates C-terminal, "v" indicates variant, "B" indicates bivalent, and "M" indicates monovalent.
Figure 4B:
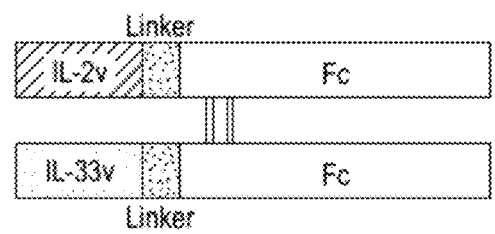
Figure 4C:
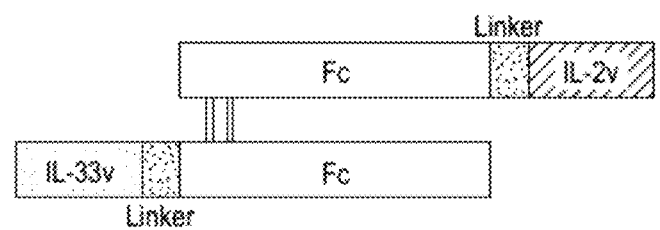
Figure 4D:
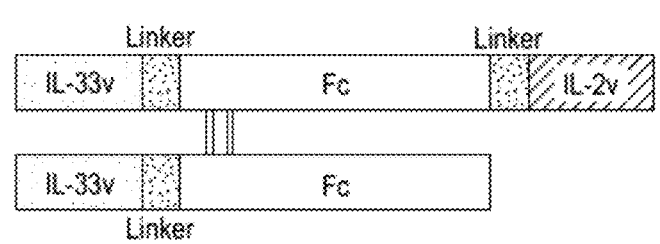
Figure 4E:
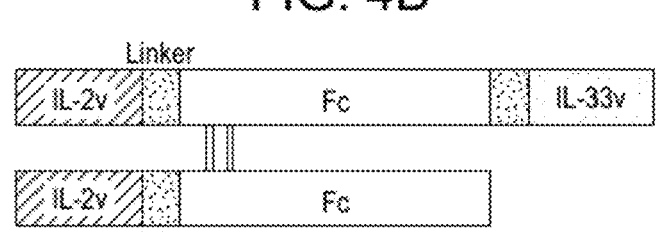
Figure 4F:
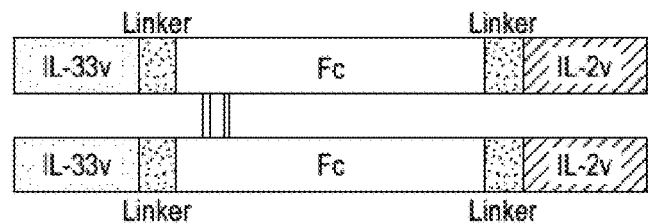
Figure 4G:
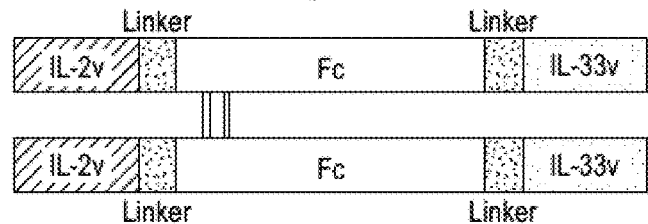
Figure 4H:
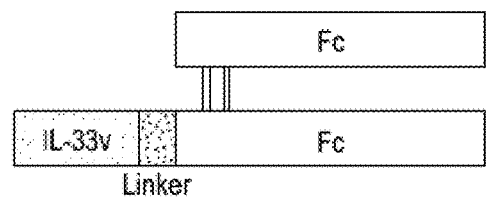
Figure 4I:
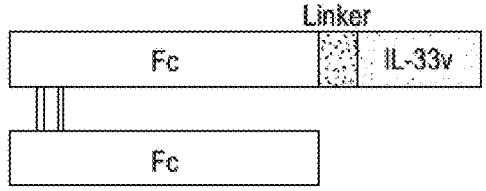
Figure 4J:
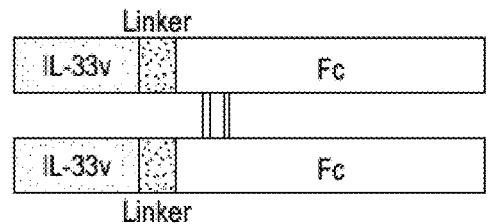
Figure 5A:
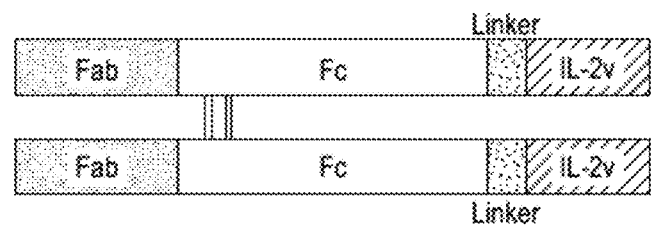
FIG. 5A-5E show schematic diagrams of dimeric proteins comprising IgG1 Fc regions. The dimeric proteins comprise an IL-2 variant (N88R, C125S) and an antigen-binding fragment (Fab) that binds to ST2 (Ab2 or Ab4). Each diagram represents two different dimeric proteins, one containing Ab2 as the Fab region, and the other containing Ab4 as the Fab region. In the protein names, "N" indicates N-terminal, "C" indicates C-terminal, "v" indicates variant, "B" indicates bivalent, and "M" indicates monovalent.
Figure 5B:
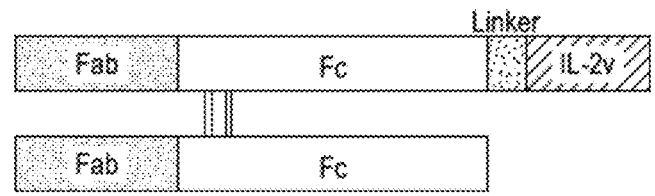
Figure 5C:
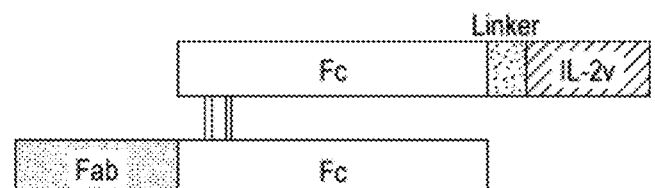
Figure 5D:
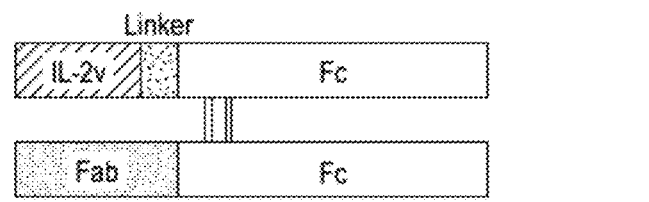
Figure 5E:
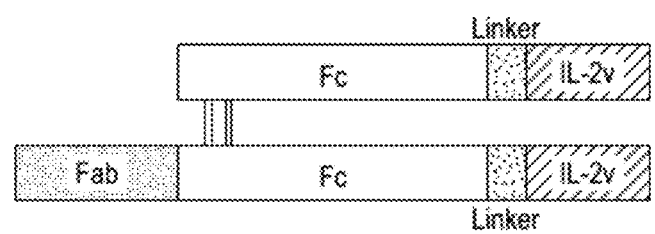
Figure 6A:
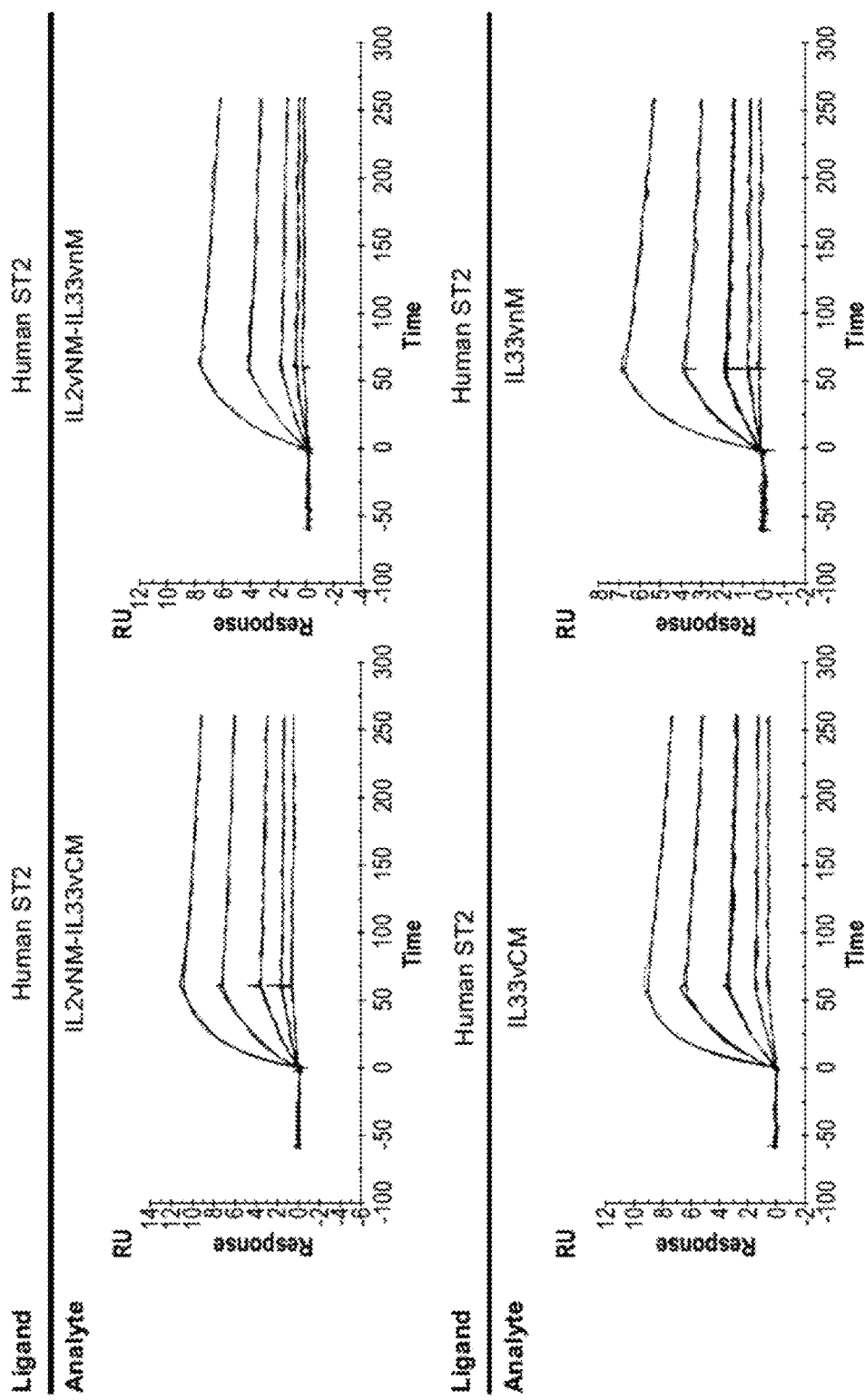
FIG. 6A shows Biacore sensorgrams showing binding between human ST2 and IL-2v/IL-33v bispecific and monovalent IL-33 molecules.
Figure 6A:
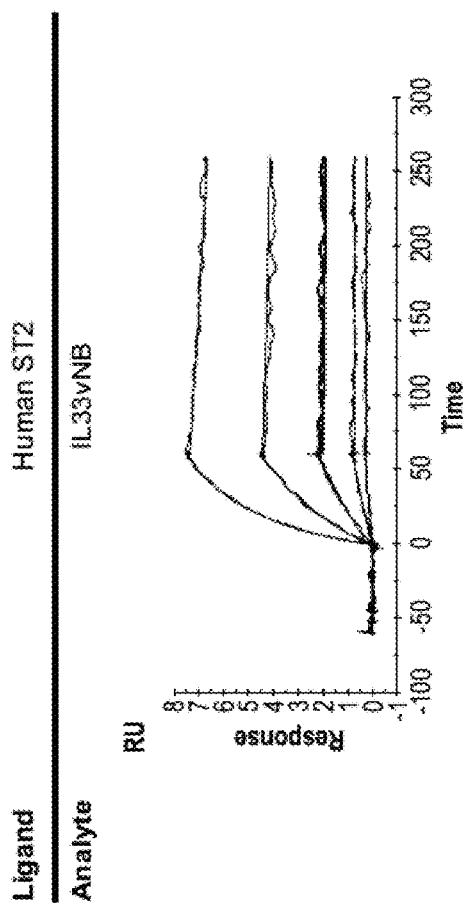
Figure 6B:
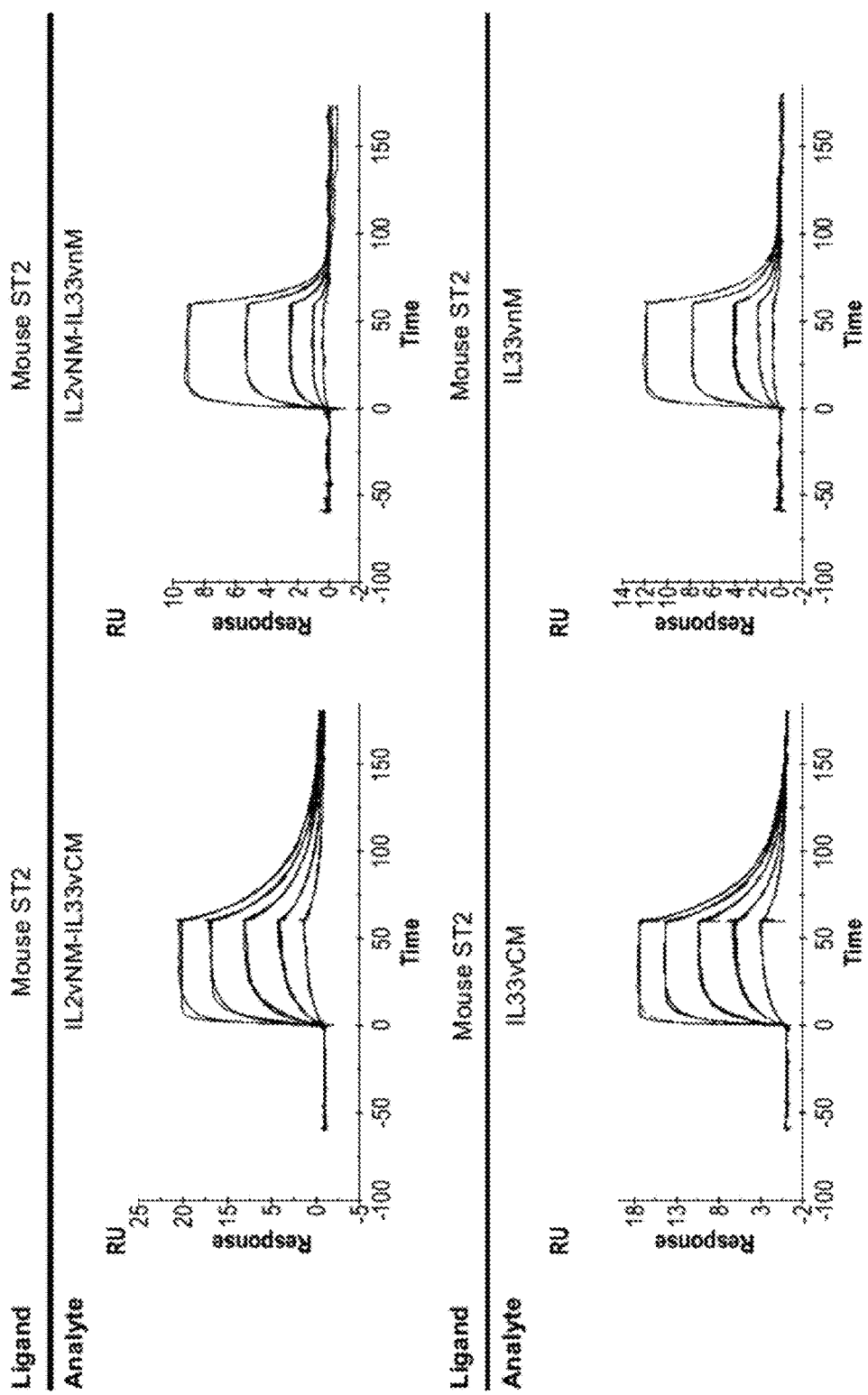
FIG. 6B shows Biacore sensorgrams showing binding between mouse ST2 and IL-2v/IL-33v bispecific & monovalent IL-33 molecules.
Figure 6B:
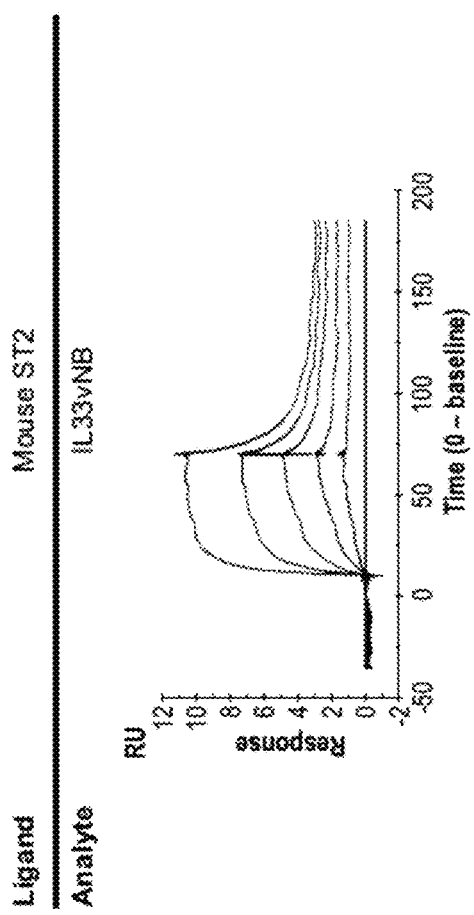
Figure 7:
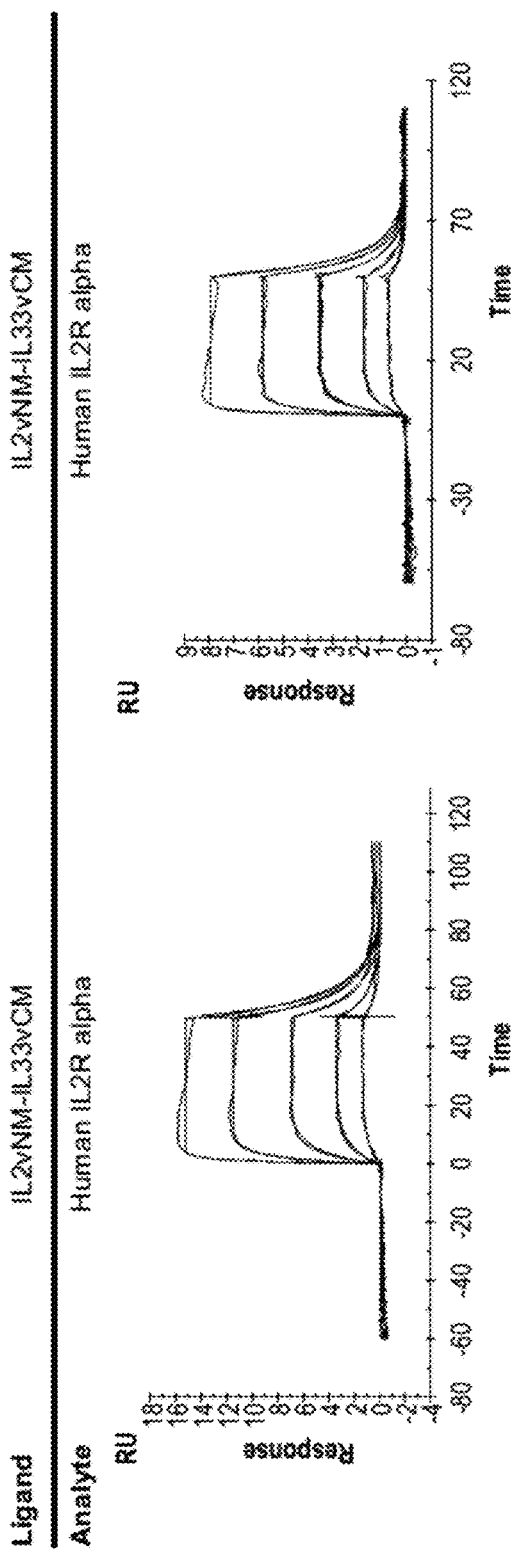
FIG. 7 shows Biacore sensorgrams showing binding between human IL2R alpha and IL-2v/IL-33v bispecific & monovalent IL-33 molecules.

| SEQ ID NO: | Description |
|---|---|
| 1 | Human IL-2 comprising the N88R and C125S mutations |
| 2 | Wildtype human IL-2 |
| 3 | Human IL-2 comprising the T3A, N88R, and C125S mutations |
| 4 | Human IgG1 Fc (N297A, T350V, L351Y, F405A, Y407V) |
| 5 | Human IgG1 Fc (N297A, T350V, T366L, K392L, T394W) |
| 6 | peptide linker GGGGSGGGGSGGGGS (G4S)₃ |
| 7 | Human IgG1 Fc moiety (N297A) |
| 8 | Human IgG1 Fc (T366Y) |
| 9 | Human IgG1 Fc (Y407T) |
| 10 | Residues 112-170 of wildtype human IL-33 |
| 11 | Residues 112-170 of human IL-33 comprising the C208S, C227S, C232S and C259S mutations |
| 12 | IL-2 (N88R, C125)/(G4S)₃ linker/IgG1 Fc (N297A, T350V, L351Y, F405A, Y407V) fusion protein FIG. 4A |
| 13 | IgG1 Fc (N297A, T350V, T366L, K392L, T394W)/(G4S)₃ linker/IL-33 (C208S, C227S, C232S, C259S) fusion protein FIG. 4A |
| 14 | IL-2 (N88R, C125)/(G4S)₃ linker/IgG1 Fc (N297A, T350V, T366L, K392L, T394W) fusion protein FIG. 4B |
| 15 | IL-33 (C208S, C227S, C232S, C259S)/(G4S)₃ linker/IgG1 Fc (N297A, T350V, L351Y, F405A, Y407V) fusion protein FIG. 4B |
| 16 | IgG1 Fc (N297A, T350V, T366L, K392L, T394W)/(G4S)₃ linker/IL-2 (N88R, C125) fusion protein FIG. 4C |
| 17 | IL-33 (C208S, C227S, C232S, C259S)/(G4S)₃ linker/IgG1 Fc (N297A, T350V, T366L, K392L, T394W)/(G4S)₃ linker/IL-2 (N88R, C125) fusion protein FIG. 4D |
| 18 | IL-2 (N88R, C125)/(G4S)₃ linker/IgG1 Fc (N297A, T350V, T366L, K392L, T394W)(G4S)₃ linker/IL-33 (C208S, C227S, C232S, C259S) fusion protein FIG. 4E |
| 19 | IL-33 (C208S, C227S, C232S, C259S)/(G4S)₃ linker/IgG1 Fc (N297A)/(G4S)₃ linker/IL-2 (N88R, C125) fusion protein FIG. 4F |
| 20 | IL-2 (N88R, C125) fusion protein/(G4S)₃ linker/IgG1 Fc (N297A)/(G4S)₃ linker/IL-33 (C208S, C227S, C232S, C259S) fusion protein FIG. 4G |
| 21 | IL-33 (C208S, C227S, C232S, C259S)/(G4S)₃ linker/IgG1 Fc (N297A) fusion protein FIG. 4J |
| 22 | Ab2HeavyIL2vC |
| 23 | Ab4HeavyIL2vC |
| 24 | Ab2HeavyIL2vC(W) |
| 25 | Ab4HeavyIL2vC(W) |
| 26 | Ab2Heavy(V) |
| 27 | Ab4Heavy(V) |
| 28 | IL2vCFc(V) |
| 29 | Ab2Kappa |
| 30 | Ab4Kappa |
| 31 | GGGGS peptide linker |

EXAMPLES

Example 1. Construction of ST2 and IL2R Targeting Bispecific Molecules

Bispecific molecules targeting ST2 (IL-33 receptor), and IL-2 high affinity receptor were constructed. All constructed molecules are listed in Tables 1 and 2 below. Their schematic diagrams are shown in FIGS. 4 and 5.

Bispecific molecules in Table 1 and FIG. 4 are Fc fusion proteins, comprised of receptor targeting moieties that are an IL-2 high affinity receptor agonist (i.e. an IL-2 variant) and an IL-33 variant. Each molecule contains either monovalent or bivalent receptor targeting moieties at the N or C terminus. A peptide linker, (G₄S)₃, connects the human IgG1 Fc domain and the receptor targeting moieties. The Fc domain contains the substitution N297A to reduced FcgR and C1q binding and thus reduce Fc effector functions. The IL-33 moiety comprises the Ser112-Thr270 fragment of human IL-33, which is a bioactive form of the IL-33 protein. In addition, the IL-33 moiety contains the substitutions C208S, C227S, C232S and C259S. The cysteine to serine substitutions have been reported to prevent inactivation of IL-33 by oxidation (Cohen et al., 2015, Nature Commun 6: 8327; WO2016/156440). This variant was selected to facilitate production of active IL-33 variant containing proteins in HEK293 cells. The IL-2 receptor agonist is a 133 amino acid human IL-2 variant containing the substitutions N88R and C125S relative to the wildtype human IL-2 sequence (SEQ ID NO: 2).

Bispecific molecules in Table 2 and FIG. 5 are comprised of the human IL-2 variant (N88R, C125S) and an antigen-binding fragment (Fab) of an anti-ST2 antibody. As a proof of concept, two anti-ST2 mAbs, Ab2 and Ab4, were selected from a published patent application (US2017/0002079 A1). Each bispecific molecule is either monovalent or bivalent with respect to the anti-ST2 antigen binding fragment and is covalently connected to the IL-2 receptor agonist at the N or C terminus through the peptide linker, (G₄S)₃.

Production of heterodimeric Fc proteins can be challenging due to potential homodimer contamination. All heterodimeric molecules in this example have mutations on the Fc domain to reduce unwanted homodimer pairing. The mutations include T350V, L351Y, F405A & Y407V on one chain; and T350V, T366L, K392L & T394W on the other chain. Such mutations have been reported to improve proper pairing and stability (Von Kreudenstein et al., 2013, mAbs 5: 646-654; WO 2014082179 A1).

TABLE 1

Dimeric proteins comprising human IgG1 Fc regions and a human IL-33 variant (C208S, C227S, C232S, C259S), or combinations of a human IL-2 variant (N88R, C125S) and the human IL-33 variant. Diagrams of the proteins are provided in FIG. 4A-4J. In the dimeric protein names, "N" indicates an N-terminal fusion to the Fc domain, "C" indicates a C-terminal fusion, "M" indicates monovalent, "B" indicates bivalent, and "v" indicates variant.

| Dimeric Protein (FIG.) | Fusion Proteins | SEQ ID NO: |
|---|---|---|
| IL2vNM-IL33vCM (4A) | IL-2 (N88R, C125)/(G4S)₃ linker/IgG1 Fc (N297A, T350V, L351Y, F405A, Y407V) | 12 |
| | IgG1 Fc (N297A, T350V, T366L, K392L, T394W)/(G4S)3 linker/IL-33 (C208S, C227S, C232S, C259S) | 13 |
| IL2vNM-IL33vNM (4B) | IL-2 (N88R, C125)/(G4S)₃ linker/IgG1 Fc (N297A, T350V, T366L, K392L, T394W) | 14 |

TABLE 1-continued

Dimeric proteins comprising human IgG1 Fc regions and a human IL-33 variant (C208S, C227S, C232S, C259S), or combinations of a human IL-2 variant (N88R, C125S) and the human IL-33 variant. Diagrams of the proteins are provided in FIG. 4A-4J. In the dimeric protein names, "N" indicates an N-terminal fusion to the Fc domain, "C" indicates a C-terminal fusion, "M" indicates monovalent, "B" indicates bivalent, and "v" indicates variant.

| Dimeric Protein (FIG.) | Fusion Proteins | SEQ ID NO: |
|---|---|---|
| | IL-33 (C208S, C227S, C232S, C259S)/(G4S)₃ linker/IgG1 Fc (N297A, T350V, L351Y, F405A, Y407V) | 15 |
| IL33vNM-IL2vCM (4C) | IgG1 Fc (N297A, T350V, T366L, K392L, T394W)/(G4S)₃ linker/IL-2 (N88R, C125) | 16 |
| | IL-33 (C208S, C227S, C232S, C259S)/(G4S)₃ linker/IgG1 Fc (N297A, T350V, L351Y, F405A, Y407V) | 15 |
| IL33vNB-IL2vCM (4D) | IL-33 (C208S, C227S, C232S, C259S)/(G4S)3 linker/IgG1 Fc (N297A, T350V, T366L, K392L, T394W)/(G4S)3 linker/IL-2 (N88R, C125) | 17 |
| | IL-33 (C208S, C227S, C232S, C259S)/(G4S)₃ linker/IgG1 Fc (N297A, T350V, L351Y, F405A, Y407V) | 15 |
| IL2vNB-IL33vCM (4E) | IL-2 (N88R, C125)/(G4S)3 linker/IgG1 Fc (N297A, T350V, T366L, K392L, T394W)(G4S)3 linker/IL-33 (C208S, C227S, C232S, C259S) | 18 |
| | IL-2 (N88R, C125)/(G4S)₃ linker/IgG1 Fc (N297A, T350V, L351Y, F405A, Y407V) | 12 |
| IL33vNB-IL2vCB (4F) | IL-33 (C208S, C227S, C232S, C259S)/(G4S)3 linker/IgG1 Fc (N297A)/(G4S)3 linker/IL-2 (N88R, C125) | 19 |
| | IL-33 (C208S, C227S, C232S, C259S)/(G4S)3 linker/IgG1 Fc (N297A)/(G4S)3 linker/IL-2 (N88R, C125) | 19 |
| IL2vNB-IL33vCB (4G) | IL-2 (N88R, C125)/(G4S)3 linker/IgG1 Fc (N297A)/(G4S)3 linker/IL-33 (C208S, C227S, C232S, C259S) | 20 |
| | IL-2 (N88R, C125)/(G4S)₃ linker/IgG1 Fc (N297A)/(G4S)₃ linker/IL-33 (C208S, C227S, C232S, C259S) | 20 |
| IL33vNM (4H) | IgG1 Fc (N297A, T350V, T366L, K392L, T394W) | 5 |
| | IL-33 (C208S, C227S, C232S, C259S)/(G4S)3 linker/IgG1 Fc (N297A, T350V, L351Y, F405A, Y407V) | 15 |
| IL33vCM (4I) | IgG1 Fc (N297A, T350V, T366L, K392L, T394W)/(G4S)3 linker/IL-33 (C208S, C227S, C232S, C259S) | 13 |
| | IgG1 Fc (N297A, T350V, L351Y, F405A, Y407V) | 4 |
| IL33vNB (4J) | IL-33 (C208S, C227S, C232S, C259S)/(G4S)3 linker/IgG1 Fc (N297A) | 21 |
| | IL-33 (C208S, C227S, C232S, C259S)/(G4S)₃ linker/IgG1 Fc (N297A) | 21 |

TABLE 2

Dimeric proteins comprising Fc regions, an antigen-binding fragment of an anti-ST2 antibody, and an IL-2 variant (N88R, C125S). Diagrams of the proteins are provided in FIG. 5A-5E.

| FIG. | Dimeric Protein | Heavy Chain 1 (Fusion Protein) | Heavy Chain 2 (Fusion Protein) | Light Chains |
|---|---|---|---|---|
| 5A | Ab2-IL2vCB | Ab2Heavy-IL2vC (SEQ ID NO: 22) | (same as Heavy Chain 1, homodimer) | Ab2Kappa (SEQ ID NO: 29) |
| | Ab4-IL2vCB | Ab4Heavy-IL2vC (SEQ ID NO: 23) | (same as Heavy Chain 1, homodimer) | Ab4Kappa (SEQ ID NO: 30) |
| 5B | Ab2-IL2vCM | Ab2Heavy(V) (SEQ ID NO: 26) | Ab2HeavyIL2vC(W) (SEQ ID NO: 24) | Ab2Kappa (SEQ ID NO: 29) |
| | Ab4-IL2vCM | Ab4Heavy(V) (SEQ ID NO: 27) | Ab4HeavyIL2vC(W) (SEQ ID NO: 25) | Ab4Kappa (SEQ ID NO: 30) |
| 5C | Ab2M-IL2vCM | Ab2Heavy(V) (SEQ ID NO: 26) | IL2vCFc(W) (SEQ ID NO: 16) | Ab2Kappa (SEQ ID NO: 29) |
| | AB4M-IL2vCM | Ab4Heavy(V) (SEQ ID NO: 27) | IL2vCFc(W) (SEQ ID NO: 16) | Ab4Kappa (SEQ ID NO: 30) |
| 5D | Ab2M-IL2vNM | Ab2Heavy(V) (SEQ ID NO: 26) | IL2vNFc(W) (SEQ ID NO: 14) | Ab2Kappa (SEQ ID NO: 29) |
| | Ab4M-IL2vNM | Ab4Heavy(V) (SEQ ID NO: 27) | IL2vNFc(W) (SEQ ID NO: 14) | Ab4Kappa (SEQ ID NO: 30) |
| 5E | Ab2M-IL2vCB | IL2vCFc(V) (SEQ ID NO: 28) | Ab2HeavyIL2vC(W) (SEQ ID NO: 24) | Ab2Kappa (SEQ ID NO: 29) |
| | Ab4M-IL2vCB | IL2vCFc(V) (SEQ ID NO: 28) | Ab4HeavyIL2C(W) (SEQ ID NO: 25) | Ab4Kappa (SEQ ID NO: 30) |

All molecules were produced in transiently-transfected HEK293 cells and purified by Protein A affinity chromatography followed by size exclusion chromatography. Due to significantly reduced proteins expression levels relative to IL2vNM-IL33vCM (FIG. 4A), the following molecules were not included in binding characterization: IL33vNM-IL2vCM (FIG. 4C), IL33vNB-IL2vCM (FIG. 4D), IL2vNB-IL33vCM (FIG. 4E), IL33vNB-IL2vCB (FIG. 4F), and IL2vNB-IL33vCB (FIG. 4G).

Example 2. Binding Characterization of IL33-IL2v Bispecific Molecules

Binding of the bispecific proteins to the extracellular domains (ECD) of ST2 (Sino Biological) and IL2Ra (Lake Pharma, Inc.) was evaluated by surface plasmon resonance (SPR) using the Biacore T200 instrument (GE). Anti-His Tag antibody (GenScript) was immobilized on CM4 chips (GE) by NHS-EDS coupling, and binding reactions were carried out in HBS-EP+ buffer (GE) at 25° C. His-tagged ST2 ECD protein was captured by anti-His Tag antibody coated chips.

For ST2 binding, histidine-tagged human or mouse ST2 ECD protein was captured on the chip as ligands. Bispecific molecules were injected as analytes at a flow rate of 50 μl/min for 60 sec and allowed to dissociate for 200 sec for human ST2 and 120 sec for mouse ST2. Bispecific molecules were prepared at various concentrations (0.12 nM-10 nM by 3-fold dilution for human ST2 interaction; and 2.5 nM-200 nM by 3-fold dilution for mouse ST2 interaction). The chip surface was regenerated with 10 mM glycine pH 1.7. Association and dissociation signals were fitted to 1:1 binding, using Biacore Evaluation Software Version 2.0 to yield kinetic constants ($k_a$& $k_d$) and to calculate the dissociation constants ($K_d$).

Sensorgrams are shown in FIGS. 6A and 6B; and kinetic constants and dissociation constants are summarized in Table 3. IL2vNM-IL33vCM and IL2vNM-IL33vNM bound to human ST2 at $K_d$ values ranging from 0.17-0.3 nM, which were slightly lower than that of previously reported wt IL-33 and ST2 interaction ($K_d$=0.4-0.7 nM) (Lingel et al., 2009, Structure 17(10): 1398-1410; Liu et al., 2013, PNAS 110 (37): 14918-14923). These proteins bound to mouse ST2, but with reduced affinity. All bispecific molecules and monovalent IL-33 molecules showed comparable affinity for human ST2. However, IL2vNM-IL33vCM showed higher affinity (>10 fold) for mouse ST2 than IL2vNM-IL33NM. In addition, IL33vCM showed higher affinity for mouse ST2 than IL33vNM. This shows that the C terminal IL-33 orientation has higher affinity for mouse ST2 than N terminal IL-33.

In addition, the IL2vNM-IL33vNM sample contained IL2v homodimer contamination detectable by SDS PAGE, while homodimers were not detectable in the IL2vNM-IL33vCM sample. In conclusion, the C terminal IL-33 bispecific protein, IL2vNM-IL33vCM exhibited higher affinity for mouse ST2 and was expressed as a more homogeneous heterodimeric protein. Therefore, it was selected for bioactivity assays with mouse T cells in Example 4.

TABLE 3

Analysis of binding to human and mouse ST2 ECD proteins.

| Analyte | ST2 | $k_a$ (1/Ms) | $k_d$ (1/s) | $K_d$ (M) |
|---|---|---|---|---|
| IL2vNM-IL33vCM | Human | 5.15E6 | 8.69E−4 | 1.69E−10 |
| | Mouse | 3.61E6 | 0.0492 | 1.36E−8 |
| IL2vNM-IL33vNM | Human | 3.41E6 | 0.0010 | 3.02E−10 |
| | Mouse | 1.17E6 | 0.1395 | 1.19E−7 |

TABLE 3-continued

Analysis of binding to human and mouse ST2 ECD proteins.

| Analyte | ST2 | $k_a$ (1/Ms) | $k_d$ (1/s) | $K_d$ (M) |
|---|---|---|---|---|
| IL33vNM | Human | 4.35E6 | 0.0012 | 2.74E−10 |
| | Mouse | 2.33E6 | 0.1163 | 4.99E−8 |
| IL33vCM | Human | 6.11E6 | 0.0011 | 1.74E−10 |
| | Mouse | 3.85E6 | 0.0452 | 1.18E−8 |

TABLE 4

Simultaneous binding of proteins to both ST2 ECD and IL2Ra ECD

| ST2 Captured Ligand | Analyte | $k_a$ (1/Ms) | $k_d$ (1/s) | $K_d$ (M) |
|---|---|---|---|---|
| IL2vNM-IL33vCM | IL2R alpha | 4.72E6 | 0.1236 | 2.62E−8 |
| IL2vNM-IL33vNM | IL2R alpha | 5.04E6 | 0.1575 | 3.25E−8 |

To test if the bispecific molecules bind to both ST2 and IL-2R alpha simultaneously, the bispecific molecules were captured by histidine tagged human ST2, which was immobilized on the chip. Subsequently, human IL2R alpha was injected as analyte at a flow rate of 50 μl/min for 50 sec and allowed to dissociated for 60 sec. IL2R alpha was prepared at various concentrations (2.5 nM-200 nM by 3 fold dilution). The chip surface was regenerated with 10 mM glycine pH 1.7. Association and dissociation signals were fitted to 1:1 binding, using Biacore Evaluation Software Version 2.0 to yield kinetic constants ($k_a$ & $k_d$) and to calculate the dissociation constants ($K_d$).

Sensorgrams are shown in FIG. 7, and kinetic constants and dissociation constants are summarized in Table 4 above. IL2vNM-IL33vCM and IL2vNM-IL33vNM bound to human IL2R alpha at $K_d$ values (26-32 nM) comparable to previously reported values (Landgraf B E, et al., 1992, J Biol Chem. 267(26):18511-9; Myszka D G, et al., 1996, Protein Sci. 5(12):2468-78; Shanafelt A B, et al., 2000, Nat Biotechnol. (11): 1197-202). These data show that the IL-2v moiety retains IL2Ra binding; and the bispecific molecules are able to bind to both ST2 and IL2Ra simultaneously because they bound to IL2Ra while being bound to ST2 protein.

Example 3. Binding Characterization of Anti-ST2/IL2v Bispecific Molecules

Binding of anti-ST2/IL2v bispecific proteins to human ST2 and IL2Ra was evaluated by surface plasmon resonance (SPR) in a manner similar to that described in Example 2.

For ST2 binding, histidine tagged human ST2 ECD protein was captured on the chip as ligand. Ab2-IL2v bispecific molecules, which are comprised of the Fab of anti-ST2 mAb (Ab2) and IL-2v, were injected as analytes at a flow rate of 50 μl/min for 400 sec and allowed to dissociated for 600 sec. Ab2-IL2v bispecific molecules were prepared at various concentrations (0.012 nM-1 nM by 3-fold dilution). Ab4-IL2v bispecific molecules, which are comprised of the Fab of anti-ST2 mAb, Ab4 and IL-2v, were injected as analyte at a flow rate of 50 μl/min for 200 sec and allowed to dissociated for 400 sec. Ab4-IL2v bispecific molecules were prepared at various concentrations (0.062 nM-5 nM by 3-fold dilution). The chip surface was regenerated with 10 mM glycine pH 1.7. Association and dissociation signals of monovalent anti-ST2 bispecific molecules were fitted to 1:1 binding, using Biacore Evaluation Software Version 2.0 to yield kinetic constants ($k_a$ & $k_d$) and to calculate the dissociation constants ($K_d$).

Figure 8A:
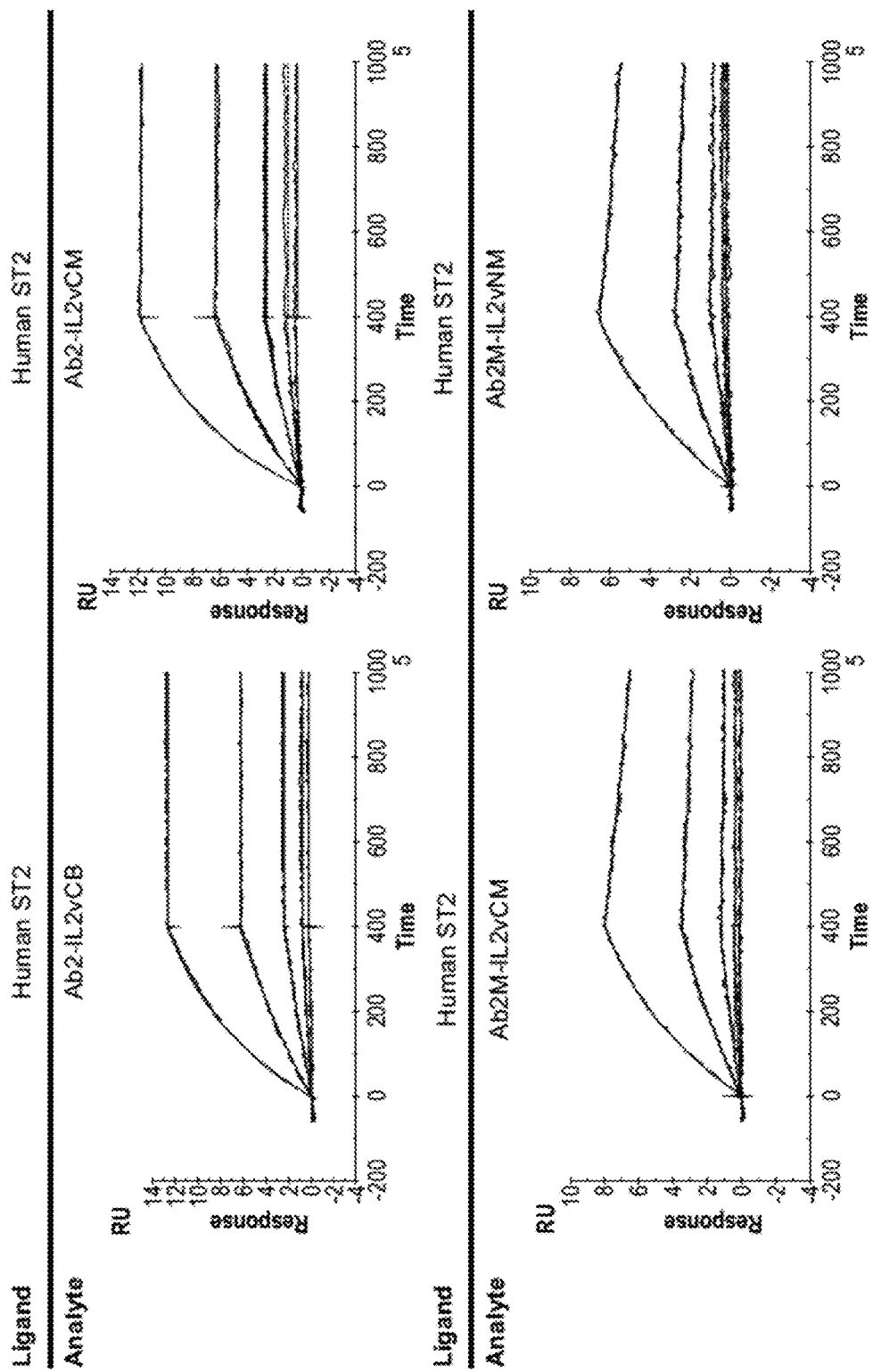
FIG. 8A shows Biacore sensorgrams showing binding between human ST2 and Ab2/IL-2v bispecific molecules.
Figure 8A:
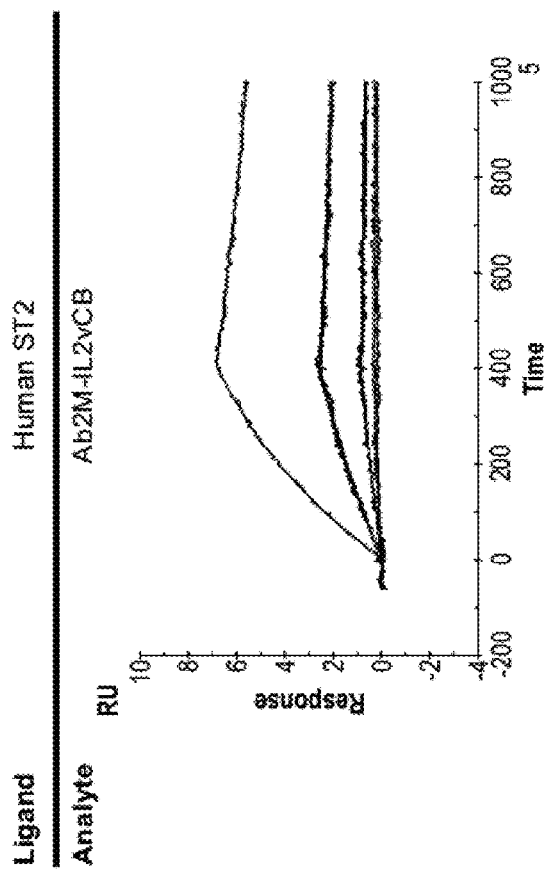
Figure 8B:
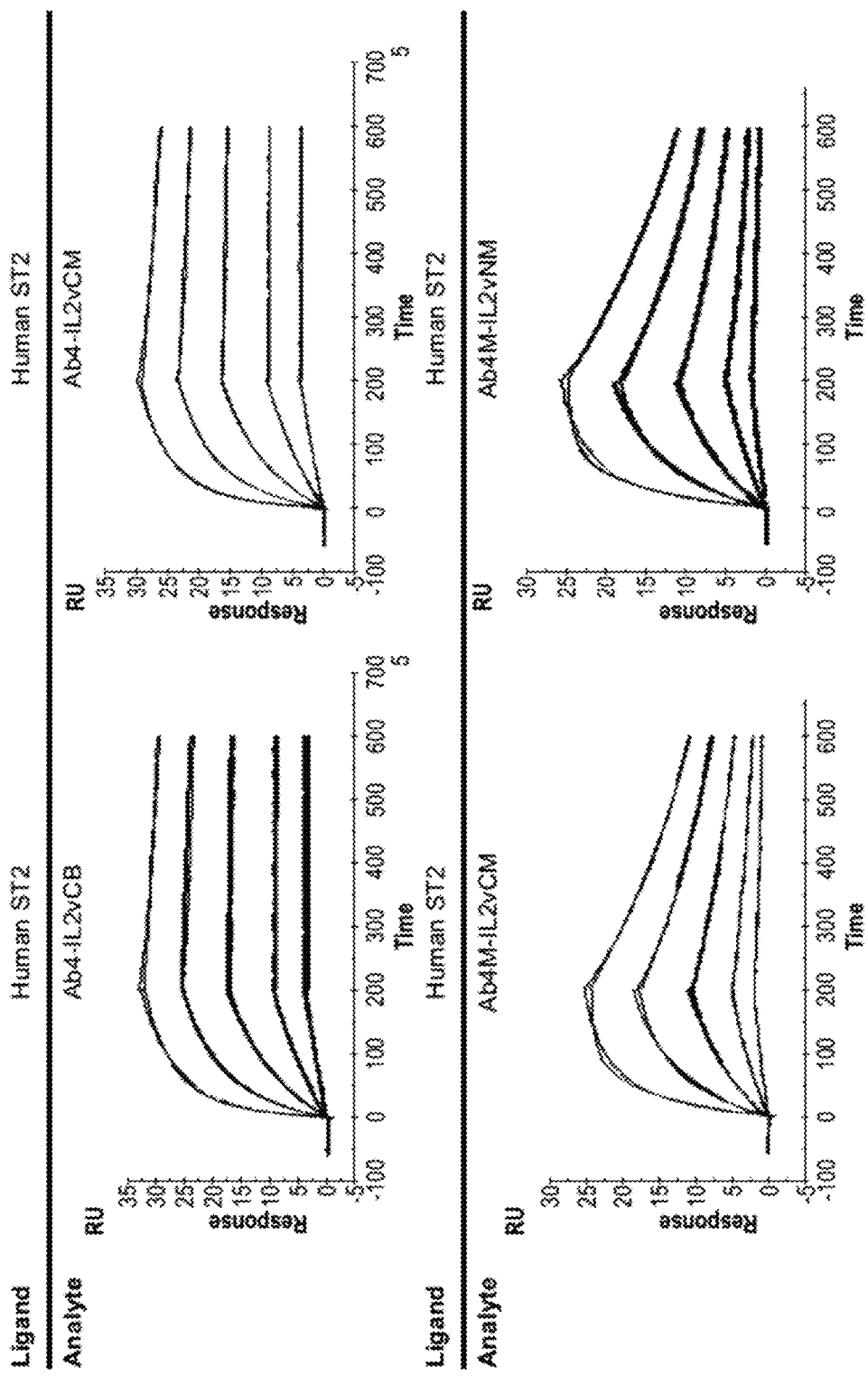
FIG. 8B shows Biacore sensorgrams showing binding between human ST2 and Ab4/IL-2v bispecific molecules.
Figure 8B:
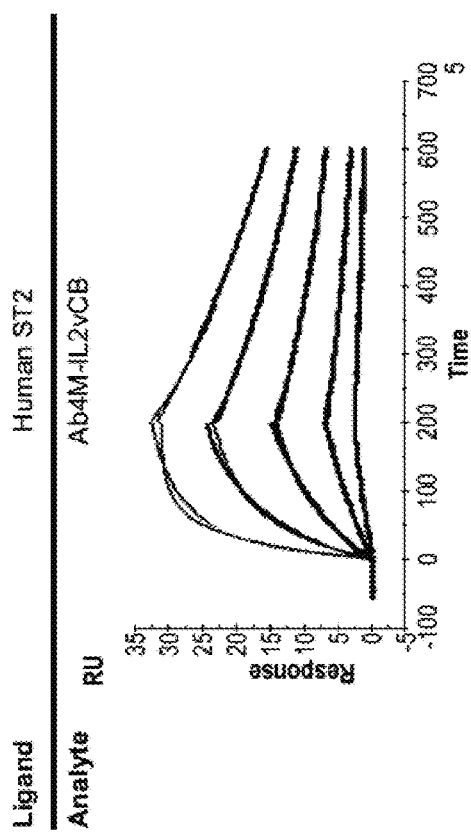

Sensorgrams are shown in FIGS. 8A and 8B; and kinetic constants and dissociation constants are summarized in Table 5 below. All bispecific molecules exhibited clear binding to ST2 protein. $K_d$ values of monovalent Ab2-IL2v bispecific molecules ranged from 94 pM to 137 pM in comparison to the reported value, 34 pM in patent US2017/0002079 A1. $K_d$ values of monovalent Ab4/IL2v bispecific molecules ranged from 289 pM to 378 pM in comparison to the reported value, 301 pM in patent US2017/0002079 A1.

TABLE 5

Analysis of binding to human ST2 ECD protein

| Analyte | Ligand | $k_a$ (1/Ms) | $k_d$ (1/s) | $K_d$ (M) |
|---|---|---|---|---|
| Ab2M-IL2vCM | Human ST2 | 3.28E6 | 3.47E−4 | 1.06E−10 |
| Ab2M-IL2vNM | Human ST2 | 3.34E6 | 3.17E−4 | 9.43E−11 |
| Ab2M-IL2vCB | Human ST2 | 2.50E6 | 3.44E−4 | 1.37E−10 |
| Ab4M-IL2vCM | Human ST2 | 5.57E6 | 0.0020 | 3.68E−10 |
| Ab4M-IL2vNM | Human ST2 | 5.44E6 | 0.0021 | 3.78E−10 |
| Ab4M-IL2vCB | Human ST2 | 6.16E6 | 0.0018 | 2.89E−10 |

To test if the bispecific molecules bind to both ST2 and IL2Ra simultaneously, the bispecific molecules were captured by histidine tagged human ST2, which was immobilized on the chip. Subsequently, IL2R alpha was injected as analyte at a flow rate of 50 μl/min for 50 sec and allowed to dissociated for 60 sec. IL2Ra was prepared at various concentrations (2.5 nM-200 nM by 3 fold dilution). The chip surface was regenerated with 10 mM glycine pH 1.7. Association and dissociation signals were fitted to 1:1 binding, using Biacore Evaluation Software Version 2.0 to yield kinetic constants ($k_a$ & $k_d$) and to calculate the dissociation constants ($K_d$).

Figure 9A:
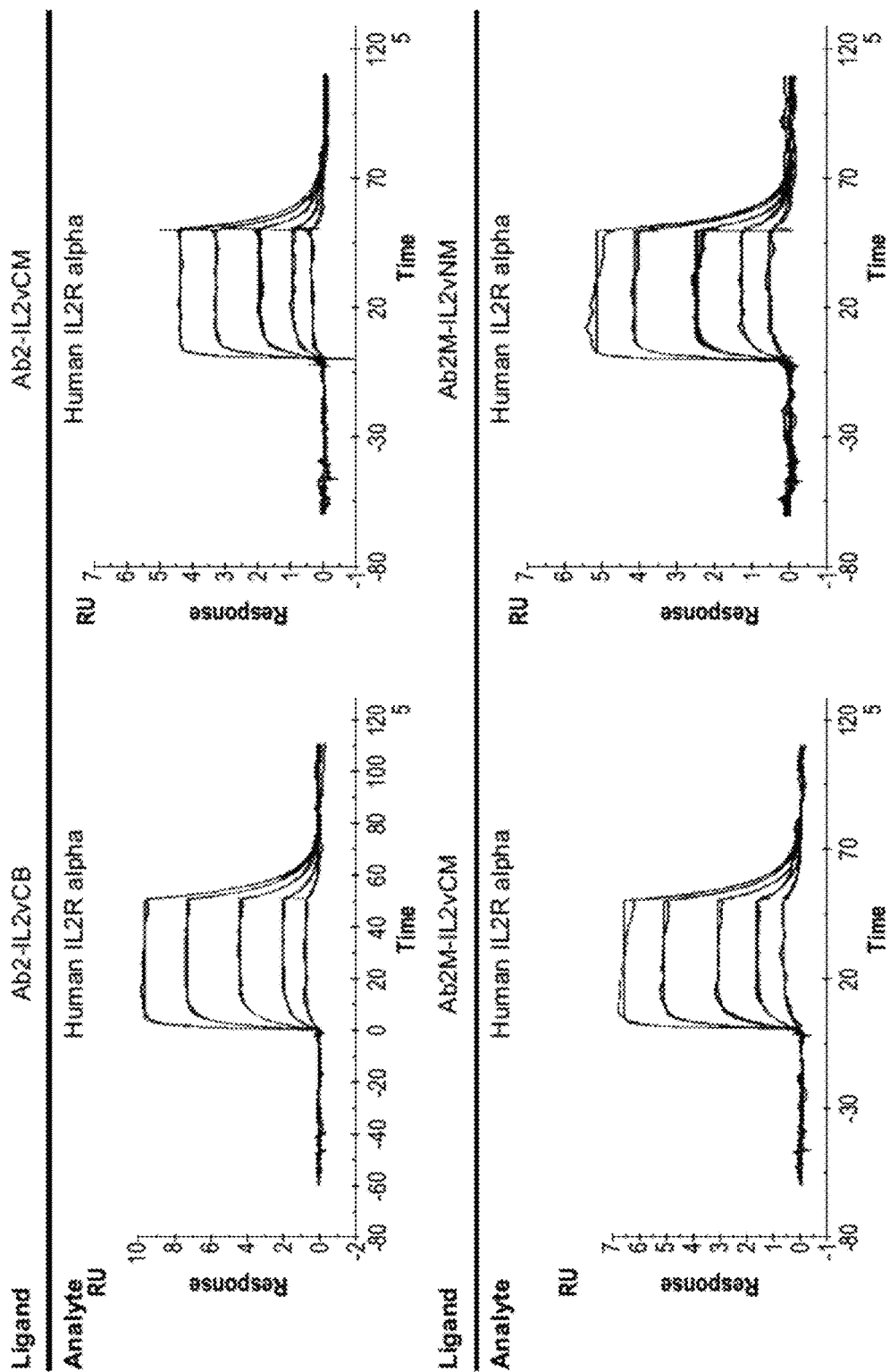
FIG. 9A shows Biacore sensorgrams showing binding between human IL2R alpha and Ab2/IL-2v bispecific molecules.
Figure 9A:
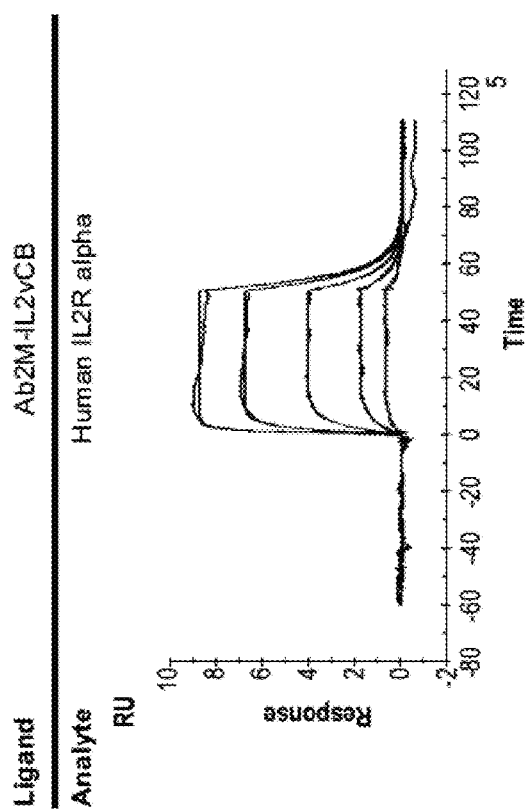
Figure 9B:
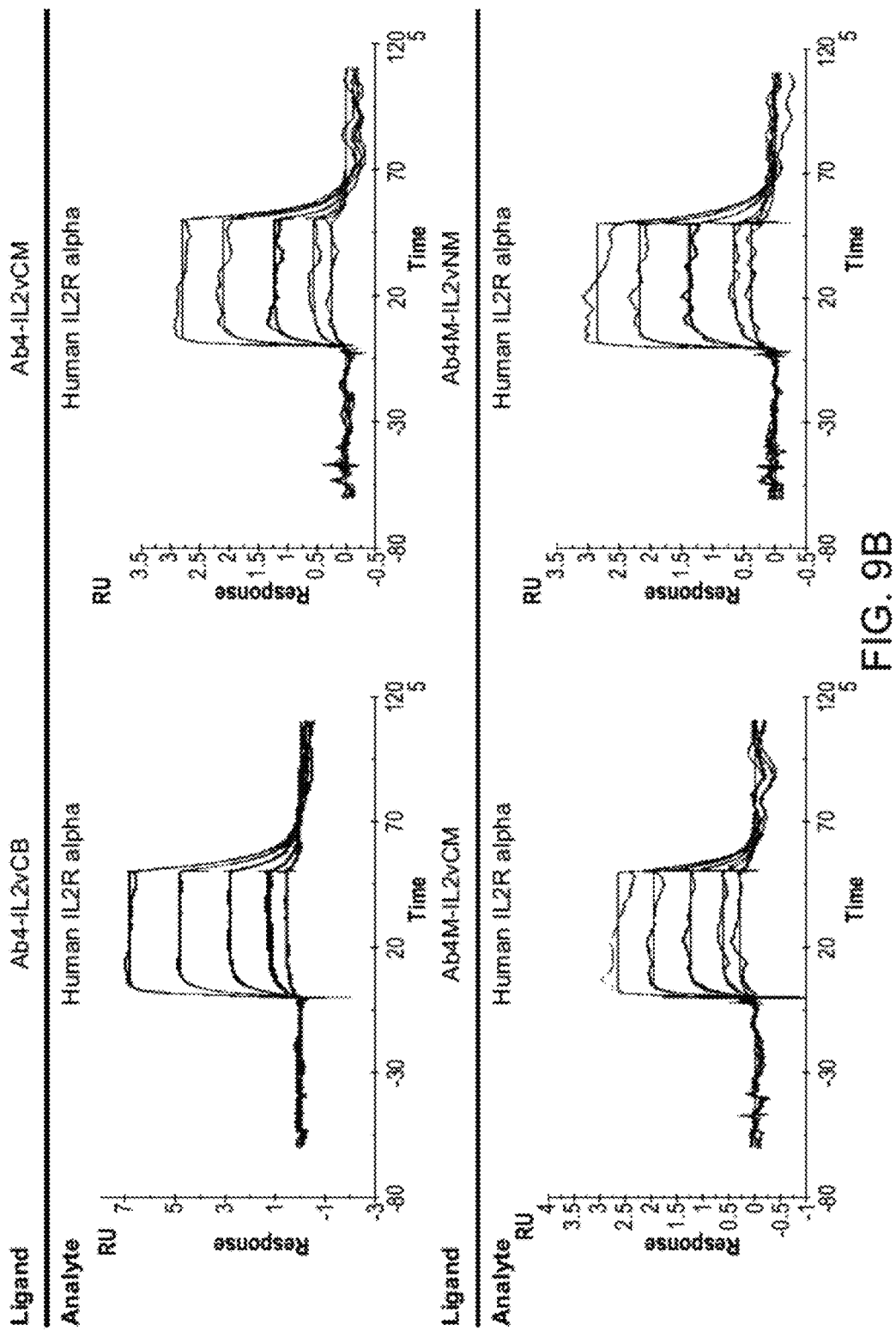
FIG. 9B shows Biacore sensorgrams showing binding between human IL2R alpha and Ab4/IL-2v bispecific molecules.
Figure 9B:
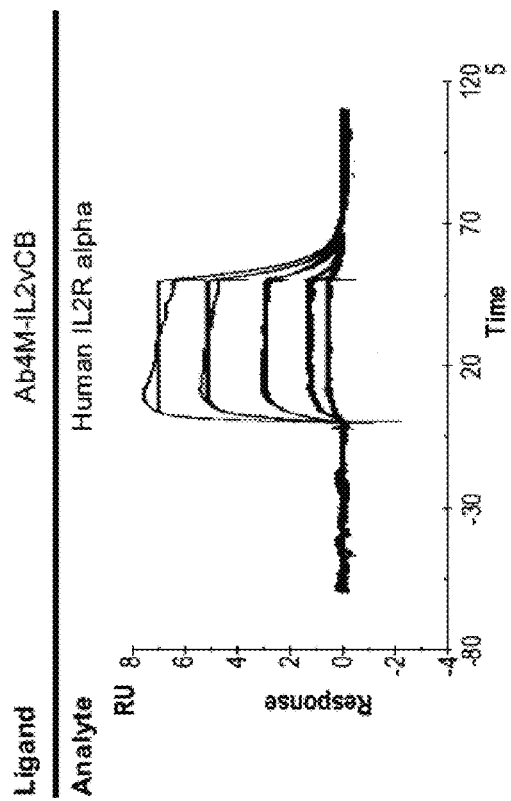

Sensorgrams are shown in FIGS. 9A and 9B; and kinetic constants and dissociation constants are summarized in Table 6 below. They all bound to human IL2R alpha at $K_d$ values (25-43 nM) comparable to the previously reported values. This shows the IL2v moiety retains IL2Ra binding; and the bispecific molecules are able to bind to both ST2 and IL2Ra simultaneously because they showed binding to IL2Ra while being bound to ST2 protein.

TABLE 6

Simultaneous binding of proteins to both ST2 ECD and IL2Ra ECD

| Analyte | ST2-bound Ligand | $k_a$ (1/Ms) | $k_d$ (1/s) | $K_d$ (M) |
|---|---|---|---|---|
| Human IL2R alpha | Ab2M-IL2vCM | 6.73E6 | 0.1819 | 2.70E−8 |
| Human IL2R alpha | Ab2M-IL2vNM | 6.26E6 | 0.1550 | 2.48E−8 |
| Human IL2R alpha | Ab2M-IL2vCB | 5.78E6 | 0.1885 | 3.26E−8 |
| Human IL2R alpha | Ab4M-IL2vCM | 9.84E6 | 0.2513 | 2.55E−8 |
| Human IL2R alpha | Ab4M-IL2vNM | 7.14E6 | 0.1788 | 2.51E−8 |
| Human IL2R alpha | Ab4M-IL2vCB | 5.27E6 | 0.2002 | 3.80E−8 |
| Human IL2R alpha | Ab2-IL2vCB | 4.59E6 | 0.1633 | 3.56E−8 |
| Human IL2R alpha | Ab2-IL2vCM | 5.13E6 | 0.1677 | 3.27E−8 |
| Human IL2R alpha | Ab4-IL2vCB | 4.55E6 | 0.1944 | 4.27E−8 |
| Human IL2R alpha | Ab4-IL2vCM | 6.26E6 | 0.2568 | 4.10E−8 |

Example 4. Activity of IL2vNM-IL33vCM on Mouse ST2+ Tregs

The activation of T cells by IL-2 can be accessed by determining the level of phosphorylated STAT5 (pSTAT5) in cells. pSTAT5 was measured by staining the cells with an anti-pSTAT5 antibody and then separating out various lymphocyte subsets by flow cytometry.

Figure 10A:
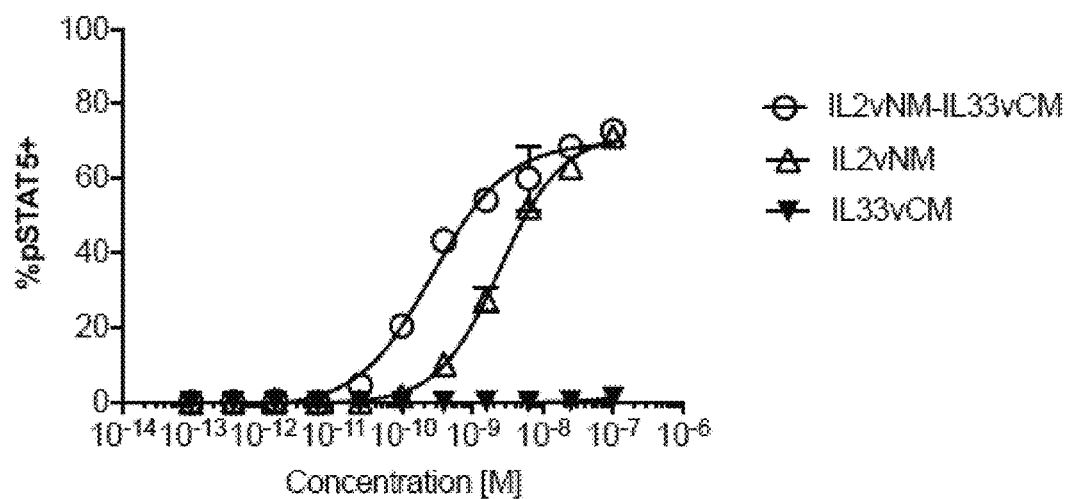
FIG. 10A shows pSTAT5 activity in ST2+ regulatory T cells in mouse spleen cell suspensions stimulated with a range of concentrations of either monovalent N88R-Fc, monovalent IL-33-Fc, or bispecific IL2vNM-IL33vCM.
Figure 10B:
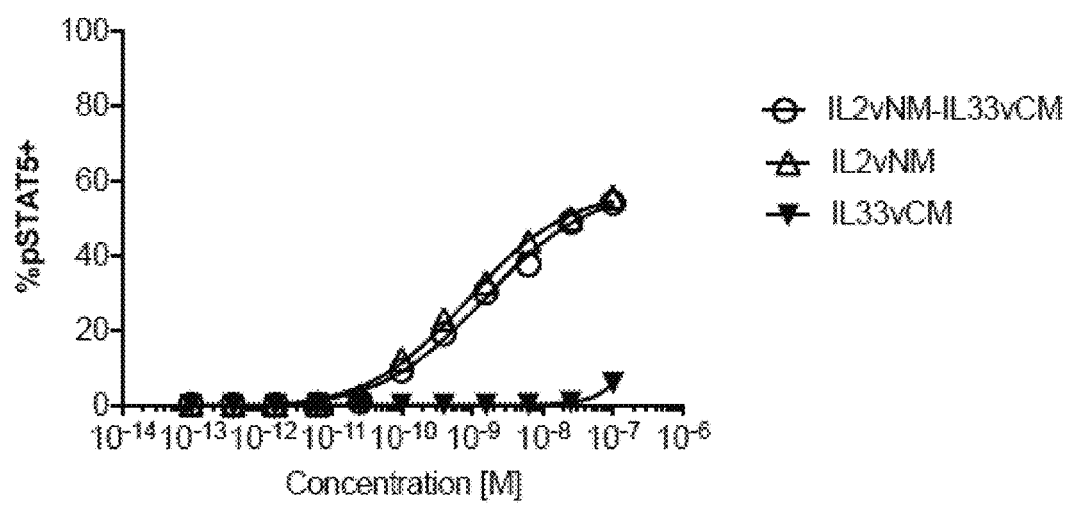
FIG. 10B shows pSTAT5 activity in ST2– regulatory T cells in mouse spleen cell suspensions stimulated with a range of concentrations of either monovalent N88R-Fc, monovalent IL-33-Fc, or bispecific IL2vNM-IL33vCM.

ST2+ Treg are found in several human tissues at high levels, but are found in blood at a very low frequency, <0.01%. Due to the difficulty of obtaining tissues from human donors, the effect of IL2vNM-IL33vCM was first assessed on ST2+ Treg from mouse spleen, which was found to have higher levels of ST2+ Tregs (5-10% of Tregs), more than were found in blood (0.1-1.0% of Tregs). Spleens were isolated from C57Bl/6J mice, and single cell suspensions stimulated with a range of concentrations of either IL2vNM (monovalent IL-2 variant Fc fusion), IL33vCM (monovalent IL-33 variant Fc fusion) or bispecific IL2vNM-IL33vCM (FIG. 10). Treg activation by IL-2 can be measured by determining the level of intracellular phosphorylated STAT5 (pSTAT5) by flow cytometry. IL33vCM induced marginal levels of pSTAT5 at only the high, unphysiological concentrations (10-100 nM, FIG. 8B). In contrast, IL2vNM induced pSTAT5 at much lower concentrations, with an EC50 of 2.4 nM on ST2+ Treg (FIG. 8A) and an EC50 of 0.86 nM on ST2-Treg (FIG. 8B). The IL2vNM-IL33vCM bispecific protein enhanced pSTAT5 induction in ST2+ Treg, above levels seen with either IL33vCM or IL2vNM proteins alone (FIG. 8A), but not in ST2-Treg (FIG. 8B). The EC50 for IL2vNM-IL33vCM in this assay was 0.26 nM, which was approximately 10 fold lower than the EC50 of IL2vNM. In conclusion, IL2vNM-IL33vCM induced greater pSTAT5 in ST2+ Treg than ST2− Treg, demonstrating that the bispecific molecule preferentially activates ST2+ Treg.

Example 5: IL-33 Moieties C-Terminal to the Fc Region are More Active

IL-33 binding to ST2 and the IL1RAcP complex activates signaling through the adaptor MyD88. The mechanisms of IL-33 signaling and downstream effects vary in different cell types. Therefore, a signaling reporter cell line was chosen to measure the bioactivity of proteins containing IL-33 moieties. The reporter cell line HEK-Blue-IL-33™ (InVivoGen Inc) is a HEK293-based cell line overexpressing human IL-33 receptors, that is a sensitive readout of IL-33 activity. The activity of the IL-33-containing molecules listed in Table 1 were tested for their ability to stimulate IL-33 signaling in HEK-Blue-IL-33™ cells according to the manufacturer' protocol.

Figure 11A:
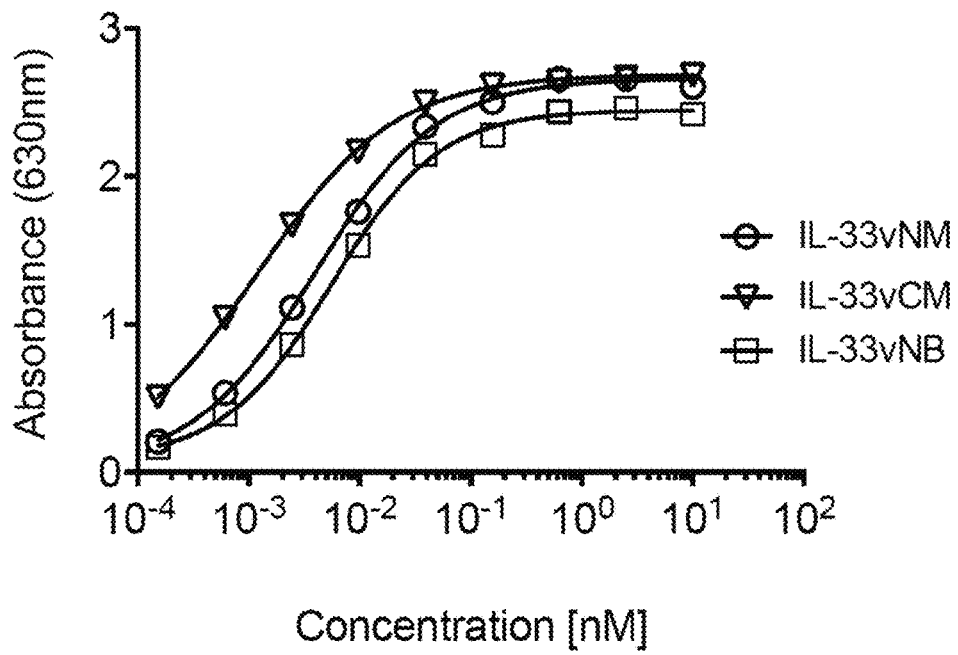
FIGS. 11A and 11B show bioactivity of the IL-33 moiety in IL33-IL2 bispecific proteins.
Figure 11B:
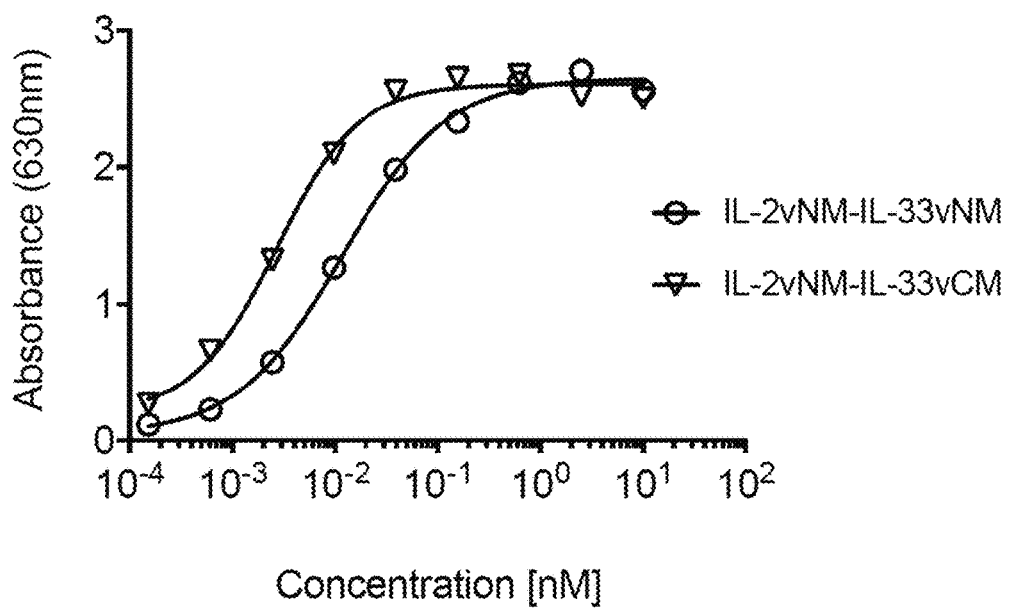

Comparing IL-33v monovalent molecules, the EC50 of the IL-33vCM was three-fold higher than that of IL-33vNM (0.016 pM compared to 0.053 pM, Table 7, FIG. 11A). Adding an additional IL-33 moiety to the N-terminus of the IL-33vNM molecule did not increase the EC50 (0.059 pM for IL-33vNB compared to 0.053 pM for IL-33vNM). Bispecific molecules with both IL-2v and IL-33v fused to the N-terminus of the Fc domain via a peptide linker (IL2vNM-IL33vNM) had appreciably lower IL-33 activity than monovalent IL-33vNM (0.128 pM compared to 0.053 pM, FIG. 11), suggesting a loss of activity due to the presence of both moieties N-terminal to the Fc domain. However, bispecific molecules with IL-2 N-terminal to the Fc domain and IL-33 C-terminal to the Fc domain (IL2vNM-IL33vCM) had better activity than any of the molecules with IL-33 N-terminal to the Fc domain (Table 7, 0.03 pM, FIG. 11B), and had only a two-fold reduction in activity compared to monovalent IL-33 C-terminal to the Fc domain (IL-33vCM).

Consistent with the kinetic analysis in Example 2, these assays established that IL2vNM-IL33vCM, with IL-33 C-terminal to the Fc domain, had superior IL-33 bioactivity activity compared to IL2vNM-IL33vNM (FIG. 11). Therefore, the IL2vNM-IL33vCM molecule was selected for further assays with mouse regulatory T cells as described above in Example 4.

TABLE 7

EC50 of IL-33 bioactivity assay

| Protein | EC50 [pM] |
| --- | --- |
| IL-33vNM | 0.053 |
| IL-33vCM | 0.016 |
| IL-33vNB | 0.059 |
| IL2vNM-IL33vNM | 0.128 |
| IL2vNM-IL33vCM | 0.03 |

Example 6. Activity of IL2/IL-33 Bispecific Molecule in Normal Mice (Prophetic)

To determine their activity on Treg populations in normal mice, BALB/c mice will be injected intravenously with a single dose of 0.001, 0.01, or 0.1 mg/kg of either IL2vNM, IL33vCM, or bispecific IL2vNM-IL33vCM proteins (e.g. FIG. 4A). Spleens and livers will be harvested 2, 4, 6 or 8 days after treatment, and numbers and percentages (as a fraction of CD4 cells) of ST2+ Treg will be determined. In addition, the proliferative index of the ST2+ and ST2− Treg subsets will be determined by intracellular staining of cells with antibody to Ki67.

If bispecific IL2vNM-IL33vCM has greater selectivity for ST2+ Tregs than the IL2vNM and IL33vCM proteins, greater expansion of ST2+ Tregs than ST2− Tregs will be observed upon treatment with the bispecific protein compared to IL2vNM and IL33vCM. An increase in the proliferative index, as reflected by the percent Ki67+ cells, will also result from treatment with the bispecific proteins compared to IL2vNM or IL33vCM. The effects of the proteins on Tregs can be correlated with the pharmacokinetics of the administered proteins. Blood samples taken after administration will be evaluated by a quantitative immunoassay to determine the pharmacokinetics of administered molecules.

Example 7. Activity in Models of Muscle Inflammation (Prophetic)

The role of ST2+ Tregs has been established in animal models of muscle inflammation. One of those animal models is acute muscle injury (Burzyn et al., 2013, Cell 155(6): 1282-1295) in wild type mice, and a second model is the mdx mouse muscular dystrophy model, a model of chronic muscle inflammation caused by genetic deficiency in dystrophin (mdx mice; Villalta et al., 2014, Sci Transl Med 5(258): 258ra142).

Acute muscle injury will be initiated in mice by the injection of cardiotoxin into hind limb muscles of C57Bl/6J mice, as described by Burzyn et al. (cited above). Treatment with 0.1 mg/kg of IL-2-IL-33 bispecific molecules (e.g. FIGS. 4A and 4B) will be initiated on the day of injury, and again on day 7. Mice will be sacrificed on day 1, 4, 7 and 14, and the number of Tregs, Teff and other infiltrating immune cells in the muscle will be determined by flow cytometry. Amphiregulin (AREG) production by Treg is a crucial mediator of muscle repair (Burzyn et al., cited above), and the frequency of AREG+ Treg, and the proliferative index (Ki67+ Treg) will be determined by intracellular flow cytometry. Measures of muscle injury and repair, such as creatine kinase levels in the serum and muscle fiber morphology will also be assessed.

For the mouse mdx muscular dystrophy model, treatment of mdx mice will be initiated at 2 weeks of age. Mice will be treated weekly with 0.1 mg/kg of test proteins and sacrificed at 6 weeks of age. The number and frequency of proliferating Treg (Ki67+) and AREG+ Treg will be measured in muscles of treated mice compared to age-matched untreated controls.

Successful activation of ST2+ Tregs will result in a numerical increase in Treg, a higher proportion of Ki67+ Treg, or a higher proportion of AREG+ Treg in muscle. Additionally, the mice may exhibit a reduction in Teff cells, decreased serum creatine kinase, and improved muscle morphology.

Example 8. Activity in Models of Inflammatory Bowel Disease (Prophetic)

A role for ST2+ Treg has been established in a mouse model of inflammatory bowel disease (Schiering et al., 2014, Nature 513(7519):564-568). The effect of test proteins on ST2+ Treg in colonic tissue will be tested in an acute model of inflammatory bowel disease. C57Bl/6J mice will be fed 3% dextran sodium sulfate (DSS) in the drinking water for 7 days. Mice will be treated IV, IP, or SC with 0.1 or 0.4 mg/kg of IL-2/IL-33 bispecific molecules (e.g. FIGS. 4A and 4B) on day 1 and day 4 of DSS treatment, with DSS treatment starting on day 1. After the 7 day DSS treatment, mice will be sacrificed, and spleens, colons and mesenteric lymph nodes (MLNs) harvested. Colon sections will analyzed by histology for disease severity and colitis scores. ST2+ Treg populations will be measured in spleens, colons and MLNs.

Successful treatment could result in Tre reduced weight loss, improved disease scores or histology in treated mice compared to controls. Disease improvement might be accompanied by a specific increase in Ki67+ proliferating ST2+ Treg in the colons and MLNs of treated mice.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A fusion protein comprising:
   a) a human IL-2 protein domain wherein the human IL-2 protein domain comprises human IL-2 with a substitution selected from the group consisting of: T3A, N88R, N88G, D20H, C125S, Q126L, and Q126F, relative to the amino acid sequence of SEQ ID NO: 2;
   b) an immunoglobulin Fc protein domain; and
   c) an antibody specific for Interleukin 1 receptor-like 1 (ST2), or an antigen-binding fragment thereof.

2. The fusion protein of claim 1, further comprising at least one peptide linker domain.

3. The fusion protein of claim 1, wherein the immunoglobulin Fc protein domain comprises an amino acid sequence selected from the group consisting of the human IgG1 Fc variant of SEQ ID NO: 4, SEQ ID NO: 5, SEQ ID NO: 7, SEQ ID NO: 8 or SEQ ID NO: 9.

4. The fusion protein of claim 2, wherein the peptide linker domain comprises the amino acid sequence of SEQ ID NO: 6.

5. The fusion protein of claim 1, further comprising a first peptide linker domain and a second peptide linker domain.

6. The fusion protein of claim 1, wherein the fusion protein comprises the amino acid sequence of SEQ ID NO: 24.

7. A dimeric protein comprising the fusion protein of claim 1.

8. A dimeric protein comprising a first fusion protein and a second fusion protein, wherein:
   a. each fusion protein comprises an immunoglobulin (IgG) Fc protein domain and at least one additional protein domain selected from the group consisting of
   i. a human IL-2 protein domain, wherein the human IL-2 protein domain comprises human IL-2 with a substitution selected from the group consisting of: T3A, N88R, N88G, D20H, C125S, Q126L, and Q126F, relative to the amino acid sequence of SEQ ID NO: 2; and
   ii. an antibody specific for Interleukin 1 receptor-like 1 (ST2), or an antigen-binding fragment thereof; and
   b. the dimeric protein comprises at least one of the human IL-2 protein domain and at least one of the antibody specific for ST2, or the antigen-binding fragment thereof.

9. The dimeric protein of claim 8, wherein at least one of the fusion proteins further comprises at least one peptide linker domain.

10. The dimeric protein of claim 8, wherein the immunoglobulin Fc protein domain comprises an amino acid sequence selected from the group consisting of the human IgG1 Fc variant of SEQ ID NO: 4, SEQ ID NO: 5, SEQ ID NO: 7, SEQ ID NO: 8 or SEQ ID NO: 9.

11. The dimeric protein of claim 9, wherein the peptide linker domain comprises the amino acid sequence of SEQ ID NO: 6.

12. The dimeric protein of claim 8, wherein
the first fusion protein comprises the amino acid sequence of SEQ ID NO: 28, the second fusion protein comprises the amino acid sequence of SEQ ID NO: 24, and the dimeric protein further comprises the amino acid sequence of SEQ ID NO: 29.

13. A pharmaceutical composition comprising the dimeric protein of claim 8.

* * * * *